United States Patent
Krogh et al.

(10) Patent No.: US 9,896,513 B2
(45) Date of Patent: Feb. 20, 2018

(54) ANTIBODIES CAPABLE OF SPECIFICALLY BINDING TWO EPITOPES ON TISSUE FACTOR PATHWAY INHIBITOR

(71) Applicant: Novo Nordisk A/S, Bagsvaerd (DK)

(72) Inventors: Berit O. Krogh, Roedovre (DK); Mikael Kofod-Hansen, Koebenhavn N (DK); Ida Hilden, Vanloese (DK); Helle H. Petersen, Koebenhavn V (DK); Lars C. Petersen, Hoersholm (DK); Jens Breinholt, Dyssegaard (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/775,108

(22) PCT Filed: Mar. 14, 2014

(86) PCT No.: PCT/EP2014/055055
§ 371 (c)(1),
(2) Date: Sep. 11, 2015

(87) PCT Pub. No.: WO2014/140240
PCT Pub. Date: Sep. 18, 2014

(65) Prior Publication Data
US 2016/0032012 A1    Feb. 4, 2016

Related U.S. Application Data

(60) Provisional application No. 61/789,274, filed on Mar. 15, 2013.

(30) Foreign Application Priority Data

Mar. 15, 2013   (EP) .................................. 13159515

(51) Int. Cl.
| | | |
|---|---|---|
| *A61K 39/00* | (2006.01) | |
| *A61K 39/395* | (2006.01) | |
| *C12P 21/08* | (2006.01) | |
| *C07K 16/00* | (2006.01) | |
| *C07K 16/38* | (2006.01) | |
| *C07K 16/46* | (2006.01) | |

(52) U.S. Cl.
CPC .......... *C07K 16/38* (2013.01); *A61K 39/3955* (2013.01); *C07K 16/468* (2013.01); *A61K 2039/505* (2013.01); *A61K 2039/507* (2013.01); *C07K 2316/96* (2013.01); *C07K 2317/24* (2013.01); *C07K 2317/31* (2013.01); *C07K 2317/34* (2013.01); *C07K 2317/526* (2013.01); *C07K 2317/53* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2011/0318356 A1 | 12/2011 | Hilden et al. | |
| 2014/0294832 A1* | 10/2014 | Wang | C07K 16/38 424/136.1 |

FOREIGN PATENT DOCUMENTS

| | | |
|---|---|---|
| EP | 539975 A1 | 5/1993 |
| WO | 2010072687 A1 | 7/2010 |
| WO | 2010072691 A1 | 7/2010 |
| WO | 2012001087 A1 | 1/2012 |
| WO | 2012135671 A2 | 10/2012 |

OTHER PUBLICATIONS

Konterman. mAbs. 2012: 182-197.*
Nordfang O. et al., The C-terminus of tissue factor pathway inhibitor (TFPI) is essential to its anticoagulant activity, Biochemistry, 1991, vol. 30, No. 43, XP002700789, pp. 10371-10376.
Baugh R. J. et al., Regulation of Extrinsic Pathway Factor Xa Formation by Tissue Factor Pathway Inhibitor*, The Journal of Biological Chemistry, 1998, vol. 273, No. 8, pp. 4378-4386.
Wesselschmidt R et al., Tissue Factor Pathway Inhibitor the Carboxy-Terminus Is Required for Optimal Inhibition of Factor Xa, Blood American Society of Hematology US, 1992, vol. 79, No. 8, XP002425036, pp. 2004-2010.
Cunningham A. C. et al., Structural and functional characterization of tissue factor pathway inhibitor following degradation by matrix metalloproteinase-8, Biochemical Journal, 2002, vol. 367, No. 2, XP002700790, pp. 451-458.
Lockett J. M. et al., Contribution of regions distal to glycine-160 to the anticoagulant activity of tissue factor pathway inhibitor, Biochemistry, 2002, vol. 41, No. 15, XP002700791, pp. 4989-4997.
Peraramelli S. et al., The Kunitz 1 and Kunitz 3 domains of tissue factor pathway inhibitor are required for efficient inhibition of factor Xa, Thrombosis and Haemostasis, 2012, vol. 108, No. 2, XP002700792, pp. 266-276.

(Continued)

*Primary Examiner* — Shulamith H Shafer
(74) *Attorney, Agent, or Firm* — Jianjie Hu

(57) ABSTRACT

The application discloses a combination of two monospecific TFPI antibodies, wherein one antibody is capable of specifically binding TFPI (1-181) and the other antibody is capable of specifically binding TFPI (182-276), as well as bispecific anti-TFPI antibodies derived from two such monospecific antibodies. Both the combination of the two monospecific antibodies and the bispecific antibody strongly enhance thrombin generation by neutralising full length TFPIα, even where the concentration of TFPI is abnormally elevated.

20 Claims, 3 Drawing Sheets

(56) References Cited

OTHER PUBLICATIONS

Stephan F. et al., Tissue factor pathway inhibitor is an inhibitor of factor VII-activating protease, Journal of Thrombosis and Haemostasis, 2012, vol. 10, No. 6, XP002700793, pp. 1165-1171.
Petersen Lars C, Hemostatic properties of a TFPI antibody, Thrombosis Research, 2012, vol. 129, No. Suppl. 2, XPO02700794, pp. S44-S45.
Schanzer J. et al., Development of Tetravalent, Bispecific CCR5 Antibodies with Antiviral Activity against CCR5 Monoclonal Antibody-Resistant HIV-1 Strains, Antimicrobial Agents and Chemotherapy, 2011, vol. 55, No. 5, XPO02700795, pp. 2369-2378.
Winkler K. et al., Changing the antigen binding specificity by single point mutations of an anti-p24 (HIV-1) antibody, The Journal of Immunology, The American Association of Immunologists, US, 2000, vol. 165, No. 8, XPO02579393, pp. 4505-4514.
Wood J. P. et al., Tissue factor pathway inhibitor-alpha inhibits prothrombinase during the initiation of blood coagulation, Proceedings of the National Academy of Sciences, 2013, vol. 110, No. 44, pp. 17838-17843.
Hoppensteadt D. A. et al., TFPI antigen levels in normal human volunteers after intravenous and subcutaneous administration of unfractionated heparin and a low molecular weight heparin, Thrombosis Research, 1995, vol. 77, No. 2, pp. 175-185.
Wong W. Y. et al., Treatment of hemophilia A and B with BAX 499, an aptamer based specific inhibitor of TFPI—Summary data of a clinical phase 1 trial, Haemophilia, 2012, vol. 18, No. 5, p. 831.

* cited by examiner

ANTIBODIES CAPABLE OF SPECIFICALLY BINDING TWO EPITOPES ON TISSUE FACTOR PATHWAY INHIBITOR

This application is a 35 U.S.C. § 371 National Stage application of International Application PCT/EP2014/055055 (WO 2014/140240), filed Mar. 14, 2014, which claims priority to European Patent Application 13159515.9, filed Mar. 15, 2013; this application claims priority under 35U.S.C. § 119 to U.S. Provisional Application 61/789,274; filed Mar. 15, 2013; the contents of which are incorporated herein by reference.

FIELD OF THE INVENTION

The present invention relates to antibodies, and compositions thereof, that are capable of binding to an epitope in the N-terminal region (residues 1-181) present in both tissue factor pathway inhibitor alpha (TFPIα) and TFPI beta (TFPIβ) and to another epitope within the C-terminal part (residues 182-276), present only in full-length TFPIα. The invention also relates to the pharmaceutical and therapeutic uses of such antibodies.

In accordance with 37 C.F.R. §1.52(e)(5), Applicants enclose herewith the Sequence Listing for the above-captioned application entitled "8678US02_SL_ST25", created on Aug. 28, 2015. The Sequence Listing is made up of 114,099 bytes, and the information contained in the attached "8678US02_SL_ST25" is identical to the information in the specification as originally filed. No new matter is added.

BACKGROUND

In the bleeding individual, coagulation is initiated by the Tissue Factor/Factor VIIa (TF/FVIIa) complex when extravascular TF is exposed to FVIIa in the blood. TF/FVIIa complex formation leads to the activation of Factor X (FX) to FXa which, together with activated Factor V (FVa), generates a limited amount of thrombin. Small amounts of thrombin activate platelets which, in turn, results in the surface exposure of platelet phospholipids that supports the assembly and binding of the tenase complex composed of activated Factor VIII (FVIIIa) and Factor IX (IXa). The tenase complex is a very efficient catalyst of FX activation and FXa generated in this second step serves as the active protease in the FVa/FXa pro-thrombinase complex responsible for the final thrombin burst. Thrombin cleaves fibrinogen to generate fibrin monomers, which polymerise to form a fibrin network which seals the leaking vessel and stops the bleeding. The rapid and extensive thrombin burst is a prerequisite for the formation of a solid and stable fibrin clot.

An inadequate propagation of FXa and thrombin generation caused by FVIII or FIX deficiency is the reason underlying the bleeding diathesis in haemophilia A and B patients, respectively. In people with haemophilia, FXa generation is primarily driven by the TF/FVIIa complex because FVIII or FIX deficiency leads to rudimentary FXa generation by the tenase complex. TF/FVIIa-mediated activation of FX to FXa is, however, temporary because tissue factor pathway inhibitor (TFPI) inhibits Factor Xa and the TF/FVIIa complex in an auto-regulatory loop. Feed-back inhibition leads to formation of a TF/FVIIa/FXa/TFPI complex. Neutralizing TFPI inhibition prolongs TF/FVIIa-mediated activation of FX during initiation of coagulation, and thereby it promotes haemostasis in people with haemophilia with an inadequate FXa generation caused by impaired tenase activity due to e.g. FVIII or FIX deficiency.

TFPI is a slow tight-binding competitive inhibitor which regulates FX activation and activity through inhibition of both TF-FVIIa and FXa. TFPI inhibition of FXa occurs in a biphasic reaction that initially leads to a loose TFPI-FXa complex which slowly rearranges to a tight binding TFPI-FXa complex where the second Kunitz-type inhibitor domain of TFPI (KPI-2) binds and blocks the active site of FXa. Following initiation of coagulation, TF/FVIIa-mediated FXa generation is tightly down-regulated by TFPI. TF/FVIIa is inhibited by TFPI in a process which as a rate limiting step involves TFPI inhibition of FXa, either when FXa is bound to the TF/FVIIa complex or bound in its near vicinity on the membrane (Baugh et al., 1998, *JBC*, 273: 4378-4386). The first Kunitz-type inhibitor domain of TFPI (KPI-1) contributes to the formation of the tight TFPI-FXa complex and it directly binds and blocks the active site of TF-bound FVIIa. The C-terminal part of TFPI, consisting of the third Kunitz-type inhibitor domain, KPI-3, and the basic C-terminal tail, does not have any direct inhibitory activity, but it enhances the formation of the TFPI-FXa complex and it binds to Protein S and to heparin-like molecules which are involved in localising TFPIα to the vascular surface.

TFPIα inhibits FXa-mediated thrombin generation by the prothrombinase complex at physiologically relevant TFPIα concentrations. This feed-back inhibition works primarily as a temporal impediment of the initiation phase of clot formation. TFPIα inhibition of FXa in the prothrombinase complex is mediated via a high-affinity interaction between the basic region of TFPIα and an acidic region in FV, which is exposed on platelet FVa and on FVa when initially activated by FXa. The FVa-dependent inhibitory activity of TFPIα is lost upon removal of the acidic region when FVa is further cleaved by thrombin generated by the prothrombinase complex. TFPIβ lacks the C-terminal basic region and is therefore not an inhibitor of prothrombinase activity (Wood et al. 2013, *PNAS*, 110: 17838-843).

Antibodies that are capable of binding TFPI are known in the art. For example, WO2010/072691, WO2012/001087 and WO2012/135671 disclose monoclonal antibodies (mAbs), each of which is capable of binding to one specific epitope of TFPI. The following limitations may apply to such an antibody that targets a single TFPI epitope, e.g. on a KPI domain, typically restricted to the paratope area of an antibody defined by a single variable region. First of all, the final inhibition of the TF/FVIIa/FXa complex is dependent on several interactions between complementary areas scattered over TFPI and the TF/FVIIa/FXa complex. This applies not only to the direct binding of KPI-1 and KPI-2 of TFPI to the active sites of FVIIa and FXa, respectively, but also to interactions with TF/FVIIa/FXa exosites which involve regions of the N- and C-terminal regions of TFPI. A monoclonal antibody that binds, for example, a single KPI may not be capable of completely blocking all inhibitory functions of TFPI, particularly at physiologically elevated concentrations of TFPI. Secondly, targeting TFPI with a monoclonal antibody or fragment thereof may cause TFPI to accumulate in the circulation as a result of a reduced renal clearance of the TFPI-mAb complex, or as a result of other clearance mechanisms which are reduced due to TFPI-mAb complex formation. Dosing of some monoclonal antibodies may also cause release of TFPI from the endothelium and rapidly increasing plasma TFPI levels, similarly to what has been observed after dosing of heparin or an aptamer, which binds to KPI-3 and the C-terminal tail of TFPI (Wong et al. *Haemophilia*, 2012, 18: LB-WE 03.1 p 831, Hoppensteadt et al., *Thromb. Res.*, 77: 175-185). Thirdly, it may be desirable to target a specific pool of TFPI. Full length circulating TFPIα is thought to be of particular importance for the regulation of coagulation at a site of injury. The fact that, of all TFPI pools, only full-length TFPIα possesses an exposed C-terminal region (residues 182-276) makes it possible to selectively target the full-length TFPIα pool. By only targeting the full-length TFPIα pool and not, for example, TFPIβ or lipoprotein associated TFPI, target mediated drug disposition may be reduced, leading to prolonged in vivo drug half-lives and lower dose requirements. However, known antibodies specifically targeting the C-terminal region of TFPIα are not capable of completely neutralising TFPIα activity, especially at elevated concentrations of TFPI. The inventors envisage that the antibodies—and combinations thereof—that are disclosed herein may address such limitations.

SUMMARY

The invention relates to a bispecific antibody that is capable of specifically binding two epitopes on TFPI, the first of which is located within TFPI (1-181) (SEQ ID NO: 1) and the second of which is located within TFPI (182-276) (numbering relative to SEQ ID NO: 1). The first of said epitopes may be on the KPI-1 domain of TFPI. Alternatively, the first of said epitopes may be on the KPI-2 domain of TFPI. The second of said epitopes may be on the KPI-3 domain of TFPI. The bispecific antibody may be a full length antibody or it may be a conjugate or fusion protein of two antibody fragments, such as a Fab-Fab conjugate or fusion protein.

The invention also relates to a combination of two monospecific antibodies, wherein the first monospecific antibody is capable of specifically binding TFPI (1-181) and the second monospecific antibody is capable of specifically binding TFPI (182-276). The first antibody may specifically bind the KPI-1 domain of TFPI or the KPI-2 domain of TFPI and the second antibody may specifically bind the KPI-3 domain of TFPI.

The invention, moreover, relates to bispecific antibodies which selectively target full-length TFPIα.

The invention also relates to a pharmaceutical formulation comprising the bispecific antibody or the combination of monospecific antibodies according to the invention, any of which may find utility as a medicament.

BRIEF DESCRIPTION OF THE SEQUENCES

Figure 1:
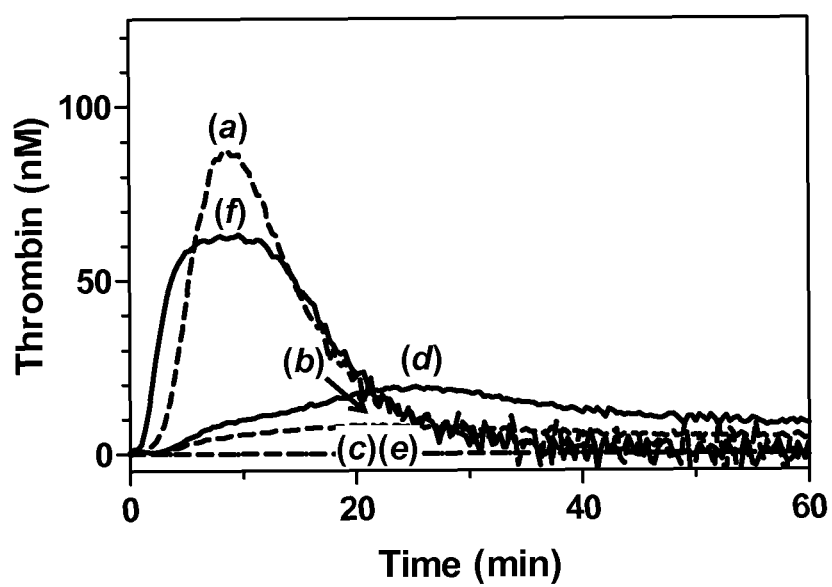
FIG. 1 shows that thrombin generation was strongly enhanced by combined antibody targeting of KPI-2 and KPI-3 of TFPI in human plasma under haemophilia A-like conditions with increased TFPI levels. Thrombin generation (TGT assay) was measured with a pool of normal human plasma (NHP) with 10 µM phosphatidyl choline/phosphatidyl serine vesicles. Initiation of coagulation was induced by re-calcification and addition of 1 pM lipidated tissue factor (Innovin®). Curve (a) shows the result obtained in NHP without further additions. Curve (b) shows the result when haemophilia A-like conditions are obtained by the addition of 100 µg/ml sheep anti human FVIII antibody (commercially available). Curve (c) shows that addition of 20 nM full-length TFPIα to haemophilia A-like plasma completely suppressed thrombin generation. Curve (d) shows that the suppression of thrombin generation, as a result of 20 nM full-length TFPIα in combination with neutralisation of FVIII, was only partly reversed by the addition of 200 nM mAb 2021 binding specifically to KPI-2. Curve (e) shows that these same conditions completely prevented that 200 nM mAb 4F110 binding specifically to KPI-3 reversed TFPI inhibition such as to allow reversal of a detectable thrombin generation. Curve (f) shows that, in contrast, a combination of 100 nM mAb 4F110 binding KPI-3 combined with 100 nM mAb 2021 binding KPI-2 effectively reversed TFPI inhibition and restored thrombin generation to approximately the level obtained in NHP without FVIII antibodies (curve (a)).

SEQ ID NO: 1 represents the amino acid sequence of human TFPI alpha.
SEQ ID NO: 2 represents the amino acid sequence of TFPI (1-181).
SEQ ID NO: 3 represents the amino acid sequence of the heavy chain (HC) of Fab 0088.
SEQ ID NO: 4 represents the amino acid sequence of the light chain (LC) of Fab 0088.
SEQ ID NO: 5 represents the amino acid sequence of the heavy chain (HC) of Fab 0094.
SEQ ID NO: 6 represents the amino acid sequence of the light chain (LC) of Fab 0094.
SEQ ID NO: 7 represents the amino acid sequence of the heavy chain (HC) of Fab 0095.
SEQ ID NO: 8 represents the amino acid sequence of the light chain (LC) of Fab 0095.
SEQ ID NO: 9 represents the amino acid sequence of the heavy chain (HC) of Fab 0089
SEQ ID NO: 10 represents the amino acid sequence of the light chain (LC) of Fab 0089.
SEQ ID NO: 11 represents the amino acid sequence of the heavy chain variable domain (VH) of mAb 22F66.
SEQ ID NO: 12 represents the amino acid sequence of the light chain variable domain (VL) of mAb 22F66.
SEQ ID NO: 13 represents the amino acid sequence of the heavy chain variable domain (VH) of mAb 22F71.
SEQ ID NO: 14 represents the amino acid sequence of the light chain variable domain (VL) of mAb 22F71.
SEQ ID NO: 15 represents the amino acid sequence of the heavy chain variable domain (VH) of mAb 22F74.
SEQ ID NO: 16 represents the amino acid sequence of the light chain variable domain (VL) of mAb 22F74.
SEQ ID NOs: 17-21 represent the nucleotide sequences of primers.
SEQ ID NO: 22 represents the amino acid sequence of the heavy chain variable domain (VH) of mAb 1 F91.
SEQ ID NO: 23 represents the amino acid sequence of the light chain variable domain (VL) of mAb 1F91.

SEQ ID NO: 24 represents the amino acid sequence of the heavy chain variable domain (VH) of mAb 2F3.
SEQ ID NO: 25 represents the amino acid sequence of the light chain variable domain (VL) of mAb 2F3.
SEQ ID NO: 26 represents the amino acid sequence of the heavy chain variable domain (VH) of mAb 2F22.
SEQ ID NO: 27 represents the amino acid sequence of the light chain variable domain (VL) of mAb 2F22.
SEQ ID NO: 28 represents the amino acid sequence of the heavy chain variable domain (VH) of mAb 2F35.
SEQ ID NO: 29 represents the amino acid sequence of the light chain variable domain (VL) of mAb 2F35.
SEQ ID NO: 30 represents the amino acid sequence of the heavy chain variable domain (VH) of mAb 2F45.
SEQ ID NO: 31 represents the amino acid sequence of the light chain variable domain (VL) of mAb 2F45.
SEQ ID NO: 32 represents the amino acid sequence of the heavy chain variable domain (VH) of mAb 2021
SEQ ID NO: 33 represents the amino acid sequence of the light chain variable domain (VL) of mAb 2021.
SEQ ID NO: 34 represents the amino acid sequence of the heavy chain variable domain (VH) of mAb 0094.
SEQ ID NO: 35 represents the amino acid sequence of the light chain variable domain (VL) of mAb 0094.
SEQ ID NO: 36 represents the amino acid sequence of the heavy chain variable domain (VH) of mAb 0095.
SEQ ID NO: 37 represents the amino acid sequence of the light chain variable domain (VL) of mAb 0095.
SEQ ID NO: 38 represents the amino acid sequence of the heavy chain variable domain (VH) of mAb 4F110.
SEQ ID NO: 39 represents the amino acid sequence of the light chain variable domain (VL) of mAb 4F110.
SEQ ID NO: 40 represents the amino acid sequence of the heavy chain (HC) of Fab 2F22.
SEQ ID NO: 41 represents the amino acid sequence of the light chain (LC) of Fab 2F22.
SEQ ID NO: 42 represents the amino acid sequence of the heavy chain variable domain (VH) of mAb 22F132.
SEQ ID NO: 43 represents the amino acid sequence of the light chain variable domain (VL) of mAb 22F132.
SEQ ID NO: 44 represents the amino acid sequence of the heavy chain variable domain (VH) of mAb 22F79.
SEQ ID NO: 45 represents the amino acid sequence of the light chain variable domain (VL) of mAb 2F79.
SEQ ID NO: 46 represents the amino acid sequence of the heavy chain variable domain (VH) of mAb 41F41.
SEQ ID NO: 47 represents the amino acid sequence of the light chain variable domain (VL) of mAb 41F41.
SEQ ID NO: 48 represents the amino acid sequence of the heavy chain (HC) of mAb 4F110.
SEQ ID NO: 49 represents the amino acid sequence of the light chain (LC) of mAb 4F110.
SEQ ID NO: 50 represents the amino acid sequence of the heavy chain (HC) of mAb 2021.
SEQ ID NO: 51 represents the amino acid sequence of the light chain (LC) of mAb 2021.
SEQ ID NO: 52 represents the amino acid sequence of the heavy chain (HC) of Fab 0296.
SEQ ID NO: 53 represents the amino acid sequence of the light chain (LC) of Fab 0296.
SEQ ID NO: 54 represents the amino acid sequence of the heavy chain (HC) of mAb 0094.
SEQ ID NO: 55 represents the amino acid sequence of the light chain (LC) of mAb 0094.
SEQ ID NO: 56 represents the amino acid sequence of the heavy chain (HC) of mAb 0095.
SEQ ID NO: 57 represents the amino acid sequence of the light chain (LC) of mAb 0095.
SEQ ID NO: 58 represents the amino acid sequence of the heavy chain (HC) of Fab 0313.
SEQ ID NO: 59 represents the amino acid sequence of the light chain (LC) of Fab 0313.
SEQ ID NO: 60 represents the amino acid sequence of the heavy chain variable domain (VH) of mAb 41F30.
SEQ ID NO: 61 represents the amino acid sequence of the light chain variable domain (VL) of mAb 41F30.
SEQ ID NO: 62 represents the amino acid sequence of tagged TFPI KPI-1/N-terminal
SEQ ID NO: 63 represents the amino acid sequence of the heavy chain (HC) of mAb 0309
SEQ ID NO: 64 represents the amino acid sequence of the light chain (LC) of mAb 0309
SEQ ID NO: 65 represents the amino acid sequence of the heavy chain (HC)) of mAb 0312.
SEQ ID NO: 66 represents the amino acid sequence of the light chain (LC) of mAb 0312.
SEQ ID NO: 67 represents the amino acid sequence of the heavy chain 1 (HC1) of mAb 0325.
SEQ ID NO: 68 represents the amino acid sequence of the light chain 1 (LC1) of mAb 0325
SEQ ID NO: 69 represents the amino acid sequence of the heavy chain 2 (HC2) of mAb 0325.
SEQ ID NO: 70 represents the amino acid sequence of the light chain 2 (LC2) of mAb 0325.

DESCRIPTION

In vivo, tissue factor pathway inhibitor (TFPI) is found in several compartments. A major fraction of TFPI is associated with the vascular endothelium and a minor fraction circulates in the blood. Two splice variants of TFPI, TFPI alpha (TFPIα) and TFPI beta (TFPIβ) have been described in humans. TFPIβ is presumably the predominant form expressed on the endothelial cell surface, whereas intracellular stores of TFPIα can be released into the circulation upon certain stimuli. TFPIα circulates in the blood as either full-length or truncated protein, associated with lipoproteins or in platelets.

Mature human TFPIα is a 276 amino acid protein (SEQ ID NO: 1) is composed of an acidic N-terminal region, three tandemly arranged Kunitz-type inhibitor domains (KPI-1, KPI-2 and KPI-3) interspersed by linker regions and a basic C-terminal tail. The KPI-1, KPI-2 and KPI-3 domains are defined as residues 26-76, residues 97-147 and residues 189-239, respectively, of SEQ ID NO: 1. Mature TFPIβ is a 193 amino acid protein covalently attached to the endothelial cell surface via a glycosylphosphatidylinositol (GPI)-anchor. The first 181 amino acids of TFPIβ are identical to TFPIα (corresponding to residues 1-181 of SEQ ID NO: 1) whereas the final 12 amino acid of the C-terminal sequence is unrelated to TFPIα and has a GPI-anchor attached to residue 193.

The present invention relates to a combination of two monospecific antibodies that bind two distinct and/or unique epitopes on TFPIα. The invention also relates to a bispecific antibody that is derived from two such monospecific antibodies. One of the monospecific antibodies, from which one antigen recognition site (or "arm") of the bispecific antibody is derived, is directed toward an epitope in the KPI-1/KPI-2 region of TFPI, herein defined as TFPI (1-181), which may be human TFPI (1-181) (SEQ ID NO: 2). The second monospecific antibody, from which the second antigen recognition site (or "arm") of the bispecific antibody is derived, is directed toward the "KPI-3 region" only present in TFPIα, herein defined as TFPI (182-276).

"KPI-1/KPI-2 region" herein refers to amino acid residues 1-181 of TFPI (i.e. TFPI (1-181)), which may be human TFPI (1-181) (SEQ ID NO: 2) and therefore encompasses the KPI-1 and KPI-2 domains of TFPI. "KPI-3 region" herein refers to amino acid residues 182-276 of TFPI (i.e. TFPI (182-276)) and therefore encompasses the KPI-3 domain and the C-terminal tail of TFPI. Hence, one monospecific antibody or one arm of the bispecific antibody or antibody fragment is capable of specifically binding to an epitope that is located within the KPI-1/KPI-2 region of TFPI (i.e. TFPI 1-181), including the acidic region near the N-terminal, KPI-1, KPI-2, the linker region between KPI-1 and KPI-2 and the first portion of the linker region between KPI-2 and KPI-3 of TFPI. The second monospecific antibody or second arm of the bispecific antibody is capable of specifically binding to an epitope that is located within amino acid residues 182-276 present only in full-length TFPIα, but not in TFPIβ. Residues 182-276 correspond to the second portion of the linker region between KPI-2 and KPI-3, the KPI-3 domain and the basic C-terminal tail.

The combination of the two monospecific antibodies of the invention, or the bispecific antibody of the invention, may have a superior profile when its pro-coagulant effect is compared to the anticipated additive effect of the individual antibodies from which it derives. For example, the two monospecific antibodies combined, or the bispecific antibody, may be capable of blocking all inhibitory functions of TFPIα, even when the concentration of TFPIα is elevated relative to, e.g. normal physiological levels. Linkage of two antigen binding moieties directed towards two separate epitopes of the invention, to obtain a bi-specific antibody or a Fab-Fab conjugate may, due to an avidity effect, lead to a more potent neutralisation of the TFPIα activity than that obtained by the combined effect of the two separate antigen binding moieties. It is not a prerequisite that both of the monospecific antibodies, from which the inventive combination or the bispecific antibody of the invention is derived, have a detectable pro-coagulant activity when tested alone, a finding which is particularly surprising. The effect arising from the antibody or the one arm of the bispecific antibody, directed toward the KPI-1/KPI-2 region, may modulate the activity of all pools of TFPI whereas the superior effect of the combination of the two monospecific antibodies, or the bispecific antibody, will preferentially modulate the activity of full length TFPIα.

A bispecific antibody of the invention may be capable of selectively modulating the activity of one specific pool of TFPI, namely TFPIα. A single arm of the bispecific antibody, capable of binding the KPI-1/KPI-2 region, may in itself, like a monospecific antibody, be incapable of significantly preventing the inhibitory activity of TFPI. It may, however, contribute more significantly to specific blockage of TFPIα inhibition when the second arm of the bispecific antibody is bound to the KPI-3 region of TFPIα. Such a bispecific antibody may thereby be capable of neutralising the inhibition of full-length TFPIα. The binding to TFPIβ of the said bispecific antibody will exclusively depend on the arm that is targeting the KPI-1/KPI-2 region. Weakening of the binding to the KPI-1/KPI-2 region will preferentially decrease the binding to TFPIβ whereas neutralization of TFPIα inhibition still remains essentially intact due to the targeting of the second arm of the bispecific antibody to the KPI-3 region. Due to reduced or absent targeting to TFPIβ or lipoprotein associated TFPI, such weakening of the affinity to the KPI-1/KPI-2 region of one arm in the said bispecific antibody may also result in reduced target mediated drug disposition leading to a prolonged in vivo drug half-life and/or lower antibody dose requirements.

The affinity of the KPI-3 region targeting component of the bispecific antibody may alone be sufficient to ensure efficient engagement of TFPI. Due to the avidity effect it may then be possible to substantially diminish binding to TFPIβ on endothelial cells while still preserving an efficient effect in plasma with neutralization of TFPIα activity. This may be obtained by weakening of the binding of the KPI-1/KPI-2 targeting component of the bispecific antibody to a point where the avidity effect of the two paratopes linked together is still present. Such antibodies may be constructed by selecting antibodies targeting certain epitopes and by tuning the absolute and relative affinities of the KPI-1/KPI-2 and KPI-3 binding components of the bispecific antibody by methods known to a person skilled in the art. Additionally, the selectivity and other properties of such a bispecific antibody may be modulated by varying the bispecific format.

The term "TFPI" as used herein encompasses naturally occurring forms of tissue factor pathway inhibitor (TFPI) that may be derived from any suitable organism. For example, TFPI for use as described herein may be a mammalian TFPI, such as human, mouse, rat, primate, bovine, ovine, rabbit or porcine TFPI. Preferably the TFPI is human TFPI. The TFPI may be a mature form of TFPI such as a TFPI protein that has undergone post-translational processing within a suitable cell. Such a mature TFPI protein may, for example, be glycosylated. The TFPI may be a full length TFPI protein. The term TFPI also encompasses variants, isoforms and other homologs of such TFPI molecules. TFPI activity refers to its inhibitory activity. Variant TFPI molecules will generally be characterised by having the same type of activity as naturally occurring TFPI, such as the ability to neutralise the catalytic activity of FXa, or the ability to inhibit a complex of TF-FVIIa/FXa.

The term "antibody" herein refers to a protein, derived from an immunoglobulin sequence, which is capable of specifically binding to an antigen or a portion thereof. The term antibody includes, but is not limited to, full length antibodies of any class (or isotype), that is, IgA, IgD, IgE, IgG, IgM and/or IgY. The term may also include one or more antigen-binding fragments of full length antibodies. An antibody that specifically binds to an antigen, or portion thereof, may bind exclusively to that antigen, or a portion thereof, or it may bind to a limited number of homologous antigens, or portions thereof.

Natural full-length antibodies usually comprise at least four polypeptide chains: two heavy (H) chains and two light (L) chains that are connected by disulfide bonds. In some cases, natural antibodies comprise less than four chains, as in the case of the heavy chain only antibodies found in camelids ($V_HH$ fragments) and the IgNARs found in Chondrichthyes. One class of immunoglobulins of particular pharmaceutical interest is the IgGs. In humans, the IgG class may be sub-divided into four sub-classes IgG1, IgG2, IgG3 and IgG4, based on the sequence of their heavy chain constant regions. The light chains can be divided into two types, kappa and lambda chains based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs) or hypervariable regions (HvRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The variable domains with the hypervariable regions of the heavy and light chains form a domain that is capable of interacting with an antigen, whilst the constant region of an antibody may mediate binding of the immunoglobulin to host tissues or factors, including, but not limited to various cells of the immune system (effector cells), Fc receptors and the first component (C1q) of the C1 complex of the classical complement system.

Antibodies of the current invention may be isolated. The term "isolated antibody" refers to an antibody that has been separated and/or recovered from (an)other component(s) in the environment in which it was produced and/or that has been purified from a mixture of components present in the environment in which it was produced.

The term "monospecific antibody", as used herein, refers to an antibody that has a single antigen recognition site (i.e. monovalent) or two identical antigen recognition sites (i.e. bivalent), each of which are specific for one common target antigen.

Monospecific antibodies of the invention may be monoclonal antibodies, in the sense that they represent a set of unique heavy and light chain variable domain sequences as expressed from a single B-cell or by a clonal population of B cells. Antibodies of the invention may be produced and purified using various methods that are known to the person skilled in the art. For example, antibodies may be produced from hybridoma cells. Antibodies may be produced by B-cell expansion. Antibodies or fragments thereof may be recombinantly expressed in mammalian or microbial expression systems, or by in vitro translation. Antibodies or fragments thereof may also be recombinantly expressed as cell surface bound molecules, by means of e.g. phage display, bacterial display, yeast display, mammalian cell display or ribosome or mRNA display. Once produced, antibodies may be screened for their ability to bind TFPI (1-181), full length TFPIα and TFPIβ, such as human TFPI (1-181), full length human TFPIα and human TFPIβ.

Various antigen-binding fragments of antibodies may also be monospecific antibodies according to the current invention, as it has been shown that the antigen-binding function of an antibody can be performed by fragments of a full-length antibody. The term "antigen-binding fragment" of an antibody refers to one or more fragment(s) of an antibody that retain(s) the ability to specifically bind to or recognise an antigen, such as TFPIα, such as human TFPIα (SEQ ID NO: 1), such as human TFPI (1-181) (SEQ ID NO:2), such as human TFPI (182-276, numbering according to SEQ ID NO: 1), such as TFPIβ, such as human TFPIβ or another target molecule, as described herein. Examples of antigen-binding fragments include Fab, Fab', Fab$_2$, Fab'$_2$, FabS, Fv (typically the VL and VH domains of a single arm of an antibody), single-chain Fv (scFv; see e.g. Bird et al., *Science* (1988) 242:42S-426; and Huston et al. *PNAS* (1988) 85: 5879-5883), dsFv, Fd (typically the VH and CH1 domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. *Protein Eng* (1997) 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol (2005) 23:1126-1136; WO2005040219, and published U.S. Patent Applications 20050238646 and 20020161201. These antibody fragments may be obtained using conventional techniques known to those of skill in the art, and the fragments may be screened for utility in the same manner as intact antibodies.

"Fab fragments" of an antibody, including "Fab", "Fab'", and "Fab'$_2$" fragments, can be derived from said antibody by cleavage of the heavy chain in the hinge region on the N-terminal or C-terminal side of the hinge cysteine residues connecting the heavy chains of the antibody. A "Fab" fragment includes the variable and constant domains of the light chain and the variable domain and the first constant domain (CH1) of the heavy chain. "Fab'$_2$" fragments comprise a pair of "Fab'" fragments that are generally covalently linked by their hinge cysteines. A Fab' is formally derived from a Fab'$_2$ fragment by cleavage of the hinge disulfide bonds connecting the heavy chains in the Fab'$_2$. Other chemical couplings than disulfide linkages of antibody fragments are also known in the art. A Fab fragment retains the ability of the parent antibody to bind to its antigen, potentially with a lower affinity. Fab'$_2$ fragments are capable of divalent binding, whereas Fab and Fab' fragments can bind monovalently. Generally, Fab fragments lack the constant CH2 and CH3 domains, i.e. the Fc part, where interaction with the Fc receptors would occur. Thus, Fab fragments are in general devoid of effector functions. Fab fragments may be produced by methods known in the art, either by enzymatic cleavage of an antibody, e.g. using papain to obtain the Fab or pepsin to obtain the Fab'$_2$, Fab fragments including Fab, Fab', Fab'$_2$ may be produced recombinantly using techniques that are well known to the person skilled in the art.

An "Fv" fragment is an antibody fragment that contains a complete antigen recognition and binding site, and generally comprises a dimer of one heavy and one light chain variable domain in association that can be covalent in nature, for example in a single chain variable domain fragment (scFv). It is in this configuration that the three hypervariable regions of each variable domain interact to define an antigen-binding site on the surface of the VH-VL dimer. Collectively, the six hypervariable regions or a subset thereof confer antigen-binding specificity to the antibody. However, even a single variable domain comprising only three hypervariable regions specific for an antigen can retain the ability to recognise and bind antigen, although usually at a lower affinity than the entire binding site (Cai & Garen, *Proc. Natl. Acad. Sci. USA* (1996) 93: 6280-6285). For example, naturally occurring camelid antibodies that only have a heavy chain variable domain (VHH) can bind antigen (Desmyter et al., *J. Biol. Chem.* (2002) 277: 23645-23650; Bond et al., *J. Mol. Biol.* (2003) 332: 643-655).

"Single-chain Fv" or "scFv" antibody fragments comprise the VH and VL domains of antibody, where these domains are present in a single polypeptide chain. Generally, the Fv polypeptide further comprises a polypeptide linker between the VH and VL domains that enables the scFv to form the desired structure for antigen-binding. For a review of scFv, see Pluckthun, 1994, In: *The Pharmacology of Monoclonal Antibodies*, Vol. 113, Rosenburg and Moore eds. Springer-Verlag, New York, pp. 269-315.

The term "diabodies" refers to small antibody fragments with two antigen-binding sites, in which fragments comprise a heavy chain variable domain (VH) connected to a light chain variable domain (VL) in the same polypeptide chain (VH and VL). By using a linker that is too short to allow pairing between the two variable domains on the same chain, the variable domains are forced to pair with complementary domains of another chain, creating two antigen-binding sites. Diabodies are described more fully, for example, in EP 404,097; WO 93/11161; and Hollinger et al., 1993, *Proc. Natl. Acad. Sci. USA*, 90:6444-6448.

The expression "linear antibodies" refers to antibodies as described in Zapata et al., 1995, *Protein Eng.*, 8(10):1057-1062. Briefly, these antibodies contain a pair of tandem Fd segments (VH-CH1-VH-CH1) that, together with complementary light chain polypeptides, form a pair of antigen-binding regions. Linear antibodies can be bispecific or monospecific.

The term "monobody" as used herein, refers to an antigen-binding molecule with a heavy chain variable domain and no light chain variable domain. A monobody can bind to an antigen in the absence of light chains and typically has three hypervariable regions, for example CDRs designated CDRH1, CDRH2, and CDRH3. A heavy chain IgG monobody has two heavy chain antigen-binding molecules connected by a disulfide bond. The heavy chain variable domain comprises one or more hypervariable regions, preferably a CDRH3 or HVL-H3 region.

Antibody fragments may be obtained using conventional recombinant or protein engineering techniques and the fragments can be screened for binding to TFPI (1-181), full length TFPIα and TFPIβ, or another function, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

The term "bispecific antibody" herein refers to an antibody that has two distinct and/or unique antigen recognition sites, or "arms", which enables it to engage two different antigens or two different epitopes on the same antigen. The term "multispecific antibody" refers to an antibody with the ability to engage two or more different antigens or two or more different epitopes on the same antigen. Multispecific antibodies thus comprise bispecific antibodies.

Bispecific antibodies in full length IgG format, mimicking natural antibodies, can be generated by fusion of two individual hybridomas to form a hybrid quadroma which produces a mixture of antibodies including a fraction of bispecific heterodimerising antibodies (Chelius D. et al.; *MAbs*. 2010 May-June; 2(3): 309-319). Bispecific heterodimerising antibodies may alternatively be produced by using recombinant technologies. Heterodimerisation can be also be achieved by engineering the dimerisation interface of the Fc region to promote heterodimerisation. One example hereof are the so-called knob-in-hole mutations where stearically bulky side chains (knobs) are introduced in one Fc matched by stearically small side chains (holes) on the opposite Fc thereby creating steric complementarity promoting heterodimerisation. Other methods for engineered heterodimerisation Fc interfaces are electrostatic complementarity, fusion to non-IgG heterodimerisation domains or utilising the natural Fab-arm exchange phenomenon of human IgG4 to control heterodimerisation. Examples of heterodimerised bispecific antibodies are well described in the literature, e.g. (Klein C, et al.; *MAbs*. 2012 November-December; 4(6): 653-663). Special attention has to be paid to the light chains in heterodimeric antibodies. Correct pairing of LCs and HCs can be accomplished by the use of a common light chain. Again engineering of the LC/HC interface can be used to promote heterodimerisation or light chain cross-over engineering as in CrossMabs. In vitro reassembly under mildly reducing conditions of antibodies from two individual IgGs containing appropriate mutations can also be used to generate bispecifics (e.g. Labrijn et al., *PNAS*, 110, 5145-5150 (2013)). Also the natural Fab-arm exchange method is reported to ensure correct light chains paring.

Multispecific antibody-based molecules may also be expressed recombinantly as fusion proteins combining the natural modules of IgGs to form multispecific and multivalent antibody derivatives as described in the literature. Examples of fusion antibodies are DVD-Igs, IgG-scFV, Diabodies, DARTs etc (Kontermann, *MAbs*. 2012 March-April 4(2): 182-197). Specific detection or purification tags, half-life extension moieties or other components can be incorporated in the fusion proteins. Additional non-IgG modalities may also be incorporated in the fusion proteins. Bispecific full length antibodies based on FC heterodimerisation are commonly referred to as asymmetic IgGs, irrespective of the LC paring methodology.

Multispecific antibody-based molecules may also be produces by chemical conjugation or coupling of individual full length IgGs or coupling of fragments of IgGs to form multispecific and multivalent antibody derivatives as described in the literature. Examples of fusion antibodies are chemical coupled Fab'$_2$, IgG-dimer etc. (Kontermann, *MAbs*. 2012 March-April 4(2): 182-197). Specific detection or purification tags, half-life extension molecules or other components can be incorporated in the conjugate proteins. Additional non-IgG polypeptide may also be incorporated in the fusion proteins. An example of such a bispecific antibody is provided in the examples.

Multispecific molecules may also be produced by combining recombinant and chemical methods including those described above.

A bispecific antibody of the current invention may comprise an antigen-binding fragment of the mAb 2021 antibody, a monoclonal antibody that was first described in WO2010/072691, which is hereby incorporated by reference.

A bispecific antibody of the current invention may comprise an antigen-binding fragment of the mAb 2F22 antibody.

A bispecific antibody of the current invention may comprise an antigen-binding fragment of the mAb 2F3 antibody, the mAb 2F45 antibody, the mAb 1 F91 antibody or the 2F35 antibody.

A bispecific antibody of the invention may further comprise an antigen-binding fragment of the mAb 4F110 antibody, the mAb 22F66 antibody or the mAb 22F71 antibody, monoclonal antibodies which were first described in WO2012/001087; which is hereby incorporated by reference; or, alternatively, an antigen-binding fragment of the mAb 22F74 antibody, as disclosed herein. For example, a bispecific antibody of the invention may comprise a Fab fragment of one of the above-mentioned antibodies. A bispecific antibody of the invention may also comprise a variant Fab fragment based on the one of the above-mentioned antibodies, such as Fab 0094 or Fab 0095 or Fab 0313 (derivatives from mAb 2021) as disclosed herein.

Bispecific, or bifunctional, antibodies of the invention can be obtained by chemical conjugation of two antibodies or fragments thereof that bind to different epitopes of TFPI:

mAb1 (or fragment)-mAb2 (or fragment)
mAb1 (or fragment)-linker-mAb2 (or fragment)

The linkage can be a single covalent bond (direct linkage) or comprise a biradical generally described as:

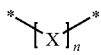

wherein X is at least, but not limited to, one atom selected from the group of carbon, oxygen, sulfur, phosphor, and nitrogen. * shows the positions of connections of this biradical. The term "biradical" refers to an even-electron chemical compound with two free radical centers which act independently of one another.

In one embodiment the linker is a chain composed of no more than 40 atoms.

In one embodiment, a chemical moiety used in the linker comprises the biradical with the structure

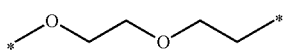

In one embodiment, the linker part comprises the biradical which has a symmetrical structure (homo-bifunctionalised linker).

The linker may also be a polymer of a structure which is similar to the description above.

In an embodiment, a chemical moiety used in the linker comprises a polymer: a macromolecule composed of two or more repeating structural units that are connected by covalent chemical bonds. Such a polymer may be hydrophilic.

The term hydrophilic or "water-soluble" refers to moieties that have some detectable degree of solubility in water. Methods to detect and/or quantify water solubility are well known in the art.

Exemplary water-soluble polymers according to the invention include peptides, saccharides, (poly)ethers, (poly)amines, (poly)carboxylic acids and the like. Peptides can have mixed sequences or can be composed of a single amino acid, e.g., (poly)lysine. An exemplary polysaccharide is (poly)sialic acid. An exemplary (poly)ether is (poly)ethylene glycol. (Poly)ethylene imine is an exemplary polyamine, and (poly)acrylic acid is a representative (poly)carboxylic acid.

Many other polymers are also suitable for the invention. Polymer backbones that are water-soluble are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(vinylpyrrolidone), poly(hydroxypropylmethacrylamide), poly([alpha]-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, as well as copolymers, terpolymers, and mixtures thereof.

The polymeric linker is, preferably, linear.

Although the molecular weight of each individual polymer chain may vary, the average molecular weight of the polymer is typically in the range of from about 1000 Da (1 kDa) to about 40,000 Da (40 kDa), such as about 1000 Da to about 12,000 Da such as about 2,000 Da to about 11,000 Da, such as about 2000 Da to about 3,000 Da; about 3000 Da to about 4,000 Da; about 4000 to about 5,000 Da; about 5000 to about 6,000 Da; about 6,000 to about 7,000 Da; about 7,000 to about 8,000 Da; about 8,000 to about 9,000 Da; about 9,000 to about 10,000 Da; or about 10,000 to about 11,000 Da. It should be understood that these sizes represent estimates rather than exact measures. According to a preferred embodiment, the molecules according to the invention are conjugated with a heterogeneous population of hydrophilic polymers.

In a particular embodiment, a chemical moiety used in the linker comprises polyethylene glycol (PEG).

The term "PEG" herein refers to a biradical comprising the structure

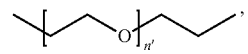

wherein n' is an integer larger than 1.

PEG is prepared by polymerisation of ethylene oxide and is commercially available over a wide range of molecular weights. The PEG for use according to the present invention is, preferably, linear.

Furthermore, "PEG" may refer to a polyethylene glycol compound, or derivative thereof, with or without coupling agents, coupling or activating moieties (e.g., with carboxylic acid/active ester, keto, alkoxyamine, thiol, triflate, tresylate, aziridine, oxirane, alkyne, azide or a maleimide moiety). The other linkers mentioned herein may also be with or without coupling agents, coupling or activating moieties (e.g., with carboxylic acid/active ester, keto, alkoxyamine, thiol, triflate, tresylate, aziridine, oxirane, alkyne, azide or a maleimide moiety)

In one particular embodiment the PEG for use according to the invention is monodisperse. In another particular embodiment, the PEG for use according to the invention is polydisperse.

Polydisperse PEG is composed of PEG molecules that have various molecular weights. The size distribution can be characterised statistically by its weight average molecular weight (Mw) and its number average molecular weight (Mn), the ratio of which is called the polydispersity index (Mw/Mn) (see e.g. "Polymer Synthesis and Characterization", J. A. Nairn, University of Utah, 2003). Mw and Mn can be measured by mass spectroscopy.

The polydispersity index may be a number that is greater than or equal to one and it may be estimated from Gel Permeation Chromatographic data. When the polydispersity index is 1, the product is monodisperse and is thus made up of compounds with a single molecular weight. When the polydispersity index is greater than 1 the polymer is polydisperse, and the polydispersity index tells how broad the distribution of polymers with different molecular weights is. The polydispersity index typically increases with the molecular weight of the PEG. In particular embodiments, the polydispersity index of the PEG for use according to the invention is i) below 1.06, ii) below 1.05, iii) below 1.04, iv) below 1.03 or v) between 1.02 and 1.03.

Different forms of PEG are available, depending on the initiator used for the polymerisation process.

Numerous methods for conjugation of PEG substituents are described in *Advanced Drug Delivery Reviews*, 2002, 54, 459-476, *Nature Reviews Drug Discovery*, 2003, 2, 214-221

DOI:10.1038/nrd1033, *Adv Polym Sci*, 2006, 192, 95-134, DOI 10.1007/12_022, Springer-Verlag, Berlin Heidelberg, 2005, and references therein. Alternatively, conjugation of the hydrophilic polymer substituent could take place by use of enzymatic methods. Such methods are for instance use of transglutaminases as described in WO2006134148.

To effect covalent attachment of the polymer molecule(s) to the polypeptide, the end groups of the polymer molecule are provided in activated form, i.e. with reactive functional groups. Suitable activated polymer molecules are commercially available, e.g. from Sigma-Aldrich Corporation, St. Louis, Mo., USA, Rapp Polymere GmbH, Tubingen, Germany, or from PolyMASC Pharmaceuticals plc, UK. Alternatively, the polymer molecules can be activated by conventional methods known in the art, e.g. as disclosed in WO 90/13540. Specific examples of activated PEG polymers are disclosed in U.S. Pat. Nos. 5,932,462 and 5,643,575. Furthermore, the following publications disclose useful polymer molecules and/or PEGylation chemistries: WO2003/031464, WO2004/099231.

The conjugation of the monoclonal antibody, or fragment thereof, with the activated polymer molecules may be conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y., Bioconjugate Techniques, Second Edition, Greg T. Hermanson, 2008, Amsterdam, Elsevier). The skilled person would be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfhydryl, succinimidyl, maleimide, vinylsulfone or haloacetate). The PEGylation may be directed towards conjugation to available attachment groups on the polypeptide (i.e. such attachment groups that are exposed at the surface of the polypeptide) or may be directed towards one or more specific attachment groups, e.g. the N-terminal amino group or a thiol. Furthermore, the conjugation may be achieved in one step or in a stepwise manner.

In another embodiment, a chemical moiety used as the linker is hydroxyethyl starch. The term "hydroxyethyl starch" (HES/HAES), as used herein, refers to a nonionic starch derivative. Different types of hydroxyethyl starches are typically described by their average molecular weight, typically around 130 to 200 kDa.

In another embodiment, a chemical moiety used in the linker comprises polysialic acid.

In another embodiment, a chemical moiety used in the linker comprises heparosan polymer which is described in for instance *Glycobiology* (2011) 21: 1331-1340.

In another embodiment, a chemical moiety in the linker is used to attach at least one of the proteins to a glycan: a polysaccharide or an oligosaccharide that is attached to a protein.

In another embodiment, a chemical moiety in the linker is used to attach at least one of the proteins to an O-linked glycan.

In another embodiment, a chemical moiety in the linker is used to attach at least one of the proteins to an N-linked glycan.

Both N-glycans and O-glycans are attached to proteins such as mAbs by the cells producing these proteins. The cellular N-glycosylation machinery recognises and glycosylates N-glycosylation signals (N-X-S/T motifs) in the amino acid chain, as the nascent protein is translocated from the ribosome to the endoplasmic reticulum (Kiely et al., *J. Biol. Chem*. 1976, 251: 5490; Glabe et al., *J. Biol. Chem*., 1980, 255, 9236). Likewise, O-glycans are attached to specific O-glycosylation sites in the amino acid chain, but the motifs triggering O-glycosylation are much more heterogeneous than the N-glycosylation signals, and our ability to predict O-glycosylation sites in amino acid sequences is still inadequate (Julenius et al., *Glycobiology*, 2005, 15: 153). Methods of conjugating polypeptides with various polymeric side groups are described e.g. in WO0331464.

In another embodiment, a chemical moiety used in the linker comprises a chemical moiety, which is used to attach said linker to at least one of the proteins with a structure selected of the biradicals:

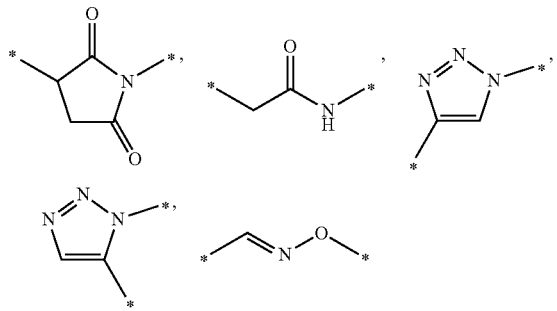

Monospecific and bispecific antibodies of the current invention may be human or humanised antibodies. The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region or a portion thereof is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalised cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains a sequence (CDR regions or parts thereof) derived from a non-human immunoglobulin. A humanised antibody is, thus, a human immunoglobulin (recipient antibody) in which at least residues from a hypervariable region of the recipient are replaced by residues from a hypervariable region of an antibody from a non-human species (donor antibody) such as from a mouse, rat, rabbit or non-human primate, which have the desired specificity, affinity, sequence composition and functionality. In some instances, framework (FR) residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (backmutation) of the amino acid residue from the donor antibody has beneficial impact on the properties of the humanised antibody. In addition to donor antibody derived backmutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another chemical agent or antibody or antibody fragment or polypeptide.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant regions.

The fragment crystallisable region ("Fc region"/"Fc domain") of an antibody is the C-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprising one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CH1 is modified such that the number of cysteine residues in the hinge region is altered, e.g., increased or decreased. This approach is described further for instance in U.S. Pat. No. 5,677,425 by Bodmer et al.

The constant region may be modified to stabilise the antibody, e.g., to reduce the risk of a bivalent antibody separating into two monovalent VH-VL fragments. For example, in an IgG4 constant region, residue S228 (according to the EU numbering index, S241 according to Kabat) may be mutated to a proline (P) residue to stabilise inter heavy chain disulphide bridge formation at the hinge (see, e.g., Angel et al., *Mol Immunol.* 1993; 30:105-8).

Bispecific antibodies or two monospecific antibodies that bind two unique epitopes on TFPI may be generated by methods known to a person skilled in the art. Bispecific formats may be prepared, for example, by chemical conjugation of two antibody fragments—such as two Fab or scFv fragments—either directly or via a linker providing the required flexibility for proper function. One specific method for coupling Fab fragments is to use the thiol functionality in cysteine residues placed appropriately in the Fab fragments.

Antibodies or fragments thereof may be defined in terms of their complementarity-determining regions (CDRs). The term "complementarity-determining region" or "hypervariable region", when used herein, refers to the regions of an antibody in which amino acid residues involved in antigen-binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al., Sequences of Proteins of Immunological Interest, 1991) Sequences of Proteins of Immunological Interest, Fifth Edition, U.S. Department of Health and Human Services, NIH Publication No. 91-3242) Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196: 901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

An antibody of the invention may comprise a CDR region from one or more of the specific antibodies disclosed herein, such as a CDR region from within SEQ ID NOs: 3 to 61, as defined using Kabat numbering or according to the sequential amino acid numbering disclosed herein.

Thus, a monospecific antibody of the invention which is capable of binding TFPI (1-181) may have the portion of the bispecific antibody of the invention which binds TFPI (1-181) may also comprise said CDR regions.

A monospecific antibody of the invention which is capable of binding TFPI (1-181) may have a heavy chain comprising:
  a CDR1 sequence corresponding to amino acids 31 to 35 of SEQ ID NO: 3, wherein one of these amino acid residues may be substituted by a different amino acid residue; and/or
  a CDR2 sequence corresponding to amino acids 50 to 66 of SEQ ID NO: 3 or SEQ ID NO: 5 or SEQ ID NO: 7, wherein one, two or three of these amino acids may be substituted by a different amino acid residue; and/or
  a CDR3 sequence corresponding to amino acids 99 to 110 of SEQ ID NO: 3, wherein one or two of these amino acid residues may be substituted by a different amino acid.

A monospecific antibody of the invention which is capable of binding TFPI (1-181) may have a light chain comprising:
  a CDR1 sequence corresponding to amino acids 24 to 39 of SEQ ID NO: 4; and/or
  a CDR2 sequence corresponding to amino acids 55 to 61 of SEQ ID NO: 4; and/or
  a CDR3 sequence corresponding to amino acids 94 to 102 of SEQ ID NO: 4.

A monospecific antibody of the invention which is capable of binding TFPI (182-276) may have a heavy chain comprising:
  a CDR1 sequence corresponding to amino acids 31 to 35 of SEQ ID NO: 9, wherein one of these amino acid residues may be substituted by a different amino acid residue; and/or
  a CDR2 sequence corresponding to amino acids 50-66 of SEQ ID NO: 9, wherein one, two or three of these amino acids may be substituted by a different amino acid residue; and/or
  a CDR3 sequence corresponding to amino acids 99-107 of SEQ ID NO: 9, wherein one or two of these amino acid residues may be substituted with a different amino acid.

A monospecific antibody of the invention which is capable of binding TFPI (182-276) may have a light chain comprising:
  a CDR1 sequence corresponding to amino acids 24-34 of SEQ ID NO: 10, wherein one or two of these amino acid residues may be substituted with a different amino acid; and/or
  a CDR2 sequence corresponding to amino acids 50-56 of SEQ ID NO: 10, wherein one of these amino acid residues may be substituted with a different amino acid; and/or
  a CDR3 sequence corresponding to amino acids 89-97 of SEQ ID NO: 10, wherein one or two of these amino acid residues may be substituted with a different amino acid.

A monospecific antibody of the invention which is capable of binding TFPI (182-276) may have a heavy chain comprising:
  a CDR1 sequence corresponding to amino acids 31-35 of SEQ ID NO: 11, wherein one of these amino acid residues may be substituted by a different amino acid residue; and/or
  a CDR2 sequence corresponding to amino acids 50-66 of SEQ ID NO: 11, wherein one, two or three of these amino acids may be substituted by a different amino acid residue; and/or
  a CDR3 sequence corresponding to amino acids 99-106 of SEQ ID NO: 11, wherein one or two of these amino acid residues may be substituted with a different amino acid.

A monospecific antibody of the invention which is capable of binding TFPI (182-276) may have a light chain comprising:
  a CDR1 sequence corresponding to amino acids 24-33 of SEQ ID NO: 12, wherein one or two of these amino acid residues may be substituted with a different amino acid; and/or
  a CDR2 sequence corresponding to amino acids 49-55 of SEQ ID NO: 12, wherein one of these amino acid residues may be substituted with a different amino acid; and/or
  a CDR3 sequence corresponding to amino acids 88-96 of SEQ ID NO: 12, wherein one or two of these amino acid residues may be substituted with a different amino acid.

The portion of the bispecific antibody of the invention which binds TFPI (182-276) may also comprise said CDR regions.

A monospecific antibody of the invention which is capable of binding TFPI (182-276) may have a heavy chain comprising:
  a CDR1 sequence corresponding to amino acids 31-35 of SEQ ID NO: 13, wherein one of these amino acid residues may be substituted by a different amino acid residue; and/or a CDR2 sequence corresponding to amino acids 50-66 of SEQ ID NO: 13, wherein one, two or three of these amino acids may be substituted by a different amino acid residue; and/or a CDR3 sequence corresponding to amino acids 99-111 of SEQ ID NO: 13, wherein one or two of these amino acid residues may be substituted with a different amino acid.

A monospecific antibody of the invention which is capable of binding TFPI (182-276) may have a light chain comprising:

a CDR1 sequence corresponding to amino acids 24-38 of SEQ ID NO: 14, wherein one, two or three of these amino acid residues may be substituted with a different amino acid; and/or a CDR2 sequence corresponding to amino acids 54-60 of SEQ ID NO: 14, wherein one of these amino acid residues may be substituted with a different amino acid; and/or a CDR3 sequence corresponding to amino acids 93-101 of SEQ ID NO: 14, wherein one or two of these amino acid residues may be substituted with a different amino acid.

A monospecific antibody of the invention which is capable of binding TFPI (182-276) may have a heavy chain comprising:

a CDR1 sequence corresponding to amino acids 31-35 of SEQ ID NO: 15, wherein one of these amino acid residues may be substituted by a different amino acid residue; and/or a CDR2 sequence corresponding to amino acids 50-66 of SEQ ID NO: 15, wherein one, two or three of these amino acids may be substituted by a different amino acid residue; and/or a CDR3 sequence corresponding to amino acids 99-106 of SEQ ID NO: 15, wherein one or two of these amino acid residues may be substituted with a different amino acid.

A monospecific antibody of the invention which is capable of binding TFPI (182-276) may have a light chain comprising:

a CDR1 sequence corresponding to amino acids 24-34 of SEQ ID NO: 16, wherein one or two of these amino acid residues may be substituted with a different amino acid; and/or a CDR2 sequence corresponding to amino acids 50-56 of SEQ ID NO: 16, wherein one of these amino acid residues may be substituted with a different amino acid; and/or a CDR3 sequence corresponding to amino acids 89-97 of SEQ ID NO: 16, wherein one or two of these amino acid residues may be substituted with a different amino acid.

The portion of the bispecific antibody of the invention which binds TFPI (182-276) may comprise said CDR regions.

A monospecific antibody according to the invention which is capable of binding TFPI (1-181) may have a heavy chain comprising:

a CDR1 sequence corresponding to amino acids 31 to 36 of SEQ ID NO: 22, wherein one of these amino acid residues may be substituted by a different amino acid residue; and/or a CDR2 sequence corresponding to amino acids 51 to 66 of SEQ ID NO: 22, wherein one, two or three of these amino acids may be substituted by a different amino acid residue; and/or a CDR3 sequence corresponding to amino acids 99 to 104 of SEQ ID NO: 22, wherein one of these amino acid residues may be substituted by a different amino acid A monospecific antibody according to the invention which is capable of binding TFPI (1-181) may have a light chain comprising:

a CDR1 sequence corresponding to amino acids 24 to 33 of SEQ ID NO: 23, wherein one or two of these amino acid residues may be substituted by a different amino acid residue; and/or a CDR2 sequence corresponding to amino acids 49 to 55 of SEQ ID NO: 23, wherein one of these amino acid residues may be substituted by a different amino acid residue; and/or a CDR3 sequence corresponding to amino acids 88 to 96 of SEQ ID NO: 23, wherein one of these amino acid residues may be substituted by a different amino acid residue.

A monospecific antibody according to the invention which is capable of binding TFPI (1-181) may have a heavy chain comprising:

a CDR1 sequence corresponding to amino acids 31 to 35 of SEQ ID NO: 24, wherein one of these amino acid residues may be substituted by a different amino acid residue; and/or a CDR2 sequence corresponding to amino acids 50 to 65 of SEQ ID NO: 24, wherein one, two or three of these amino acids may be substituted by a different amino acid residue; and/or a CDR3 sequence corresponding to amino acids 98 to 110 of SEQ ID NO: 24, wherein one or two of these amino acid residues may be substituted by a different amino acid.

A monospecific antibody according to the invention which is capable of binding TFPI (1-181) may have a light chain comprising:

a CDR1 sequence corresponding to amino acids 24 to 34 of SEQ ID NO: 25, wherein one, two or three of these amino acid residues may be substituted by a different amino acid residue; and/or a CDR2 sequence corresponding to amino acids 50 to 56 of SEQ ID NO: 25, wherein one of these amino acid residues may be substituted by a different amino acid residue; and/or a CDR3 sequence corresponding to amino acids 89 to 96 of SEQ ID NO: 25, wherein one of these amino acid residues may be substituted by a different amino acid residue.

A monospecific antibody according to the invention which is capable of binding TFPI (1-181) may have a heavy chain comprising:

a CDR1 sequence corresponding to amino acids 31 to 35 of SEQ ID NO: 28, wherein one of these amino acid residues may be substituted by a different amino acid residue; and/or a CDR2 sequence corresponding to amino acids 50 to 66 of SEQ ID NO: 28, wherein one, two or three of these amino acids may be substituted by a different amino acid residue; and/or a CDR3 sequence corresponding to amino acids 99 to 105 of SEQ ID NO: 28, wherein one or two of these amino acid residues may be substituted by a different amino acid.

A monospecific antibody according to the invention which is capable of binding TFPI (1-181) may have a light chain comprising:

a CDR1 sequence corresponding to amino acids 24 to 39 of SEQ ID NO: 29, wherein one, two or three of these amino acid residues may be substituted by a different amino acid residue; and/or a CDR2 sequence corresponding to amino acids 55 to 61 of SEQ ID NO: 29, wherein one of these amino acid residues may be substituted by a different amino acid residue; and/or a CDR3 sequence corresponding to amino acids 94 to 102 of SEQ ID NO: 29, wherein one of these amino acid residues may be substituted by a different amino acid residue.

An monospecific antibody according to the invention which is capable of binding TFPI (1-181) may have a heavy chain comprising:

a CDR1 sequence corresponding to amino acids 31 to 35 of SEQ ID NO: 30, wherein one of these amino acid residues may be substituted by a different amino acid residue; and/or a CDR2 sequence corresponding to amino acids 50 to 65 of SEQ ID NO: 30, wherein one, two or three of these amino acids may be substituted by a different amino acid residue; and/or a CDR3 sequence corresponding to amino acids 98 to 110 of SEQ ID NO: 30, wherein one or two of these amino acid residues may be substituted by a different amino acid.

A monospecific antibody according to the invention which is capable of binding TFPI (1-181) may have a light chain comprising:

a CDR1 sequence corresponding to amino acids 24 to 34 of SEQ ID NO: 31, wherein one, two or three of these amino acid residues may be substituted by a different amino acid residue; and/or a CDR2 sequence corresponding to amino acids 50 to 56 of SEQ ID NO: 31, wherein one of these amino acid residues may be substituted by a different amino acid residue; and/or a CDR3 sequence corresponding to amino acids 89 to 96 of SEQ ID NO: 31, wherein one of these amino acid residues may be substituted by a different amino acid residue.

A monospecific antibody of the invention which is capable of binding TFPI (182-276) may have a heavy chain comprising:

a CDR1 sequence corresponding to amino acids 31-35 of SEQ ID NO: 42, wherein one of these amino acid residues may be substituted by a different amino acid residue; and/or a CDR2 sequence corresponding to amino acids 50-66 of SEQ ID NO: 42, wherein one, two or three of these amino acids may be substituted by a different amino acid residue; and/or a CDR3 sequence corresponding to amino acids 99-105 of SEQ ID NO: 42, wherein one or two of these amino acid residues may be substituted with a different amino acid.

A monospecific antibody of the invention which is capable of binding TFPI (182-276) may have a light chain comprising:

a CDR1 sequence corresponding to amino acids 24-38 of SEQ ID NO: 43, wherein one, two or three of these amino acid residues may be substituted with a different amino acid; and/or a CDR2 sequence corresponding to amino acids 54-60 of SEQ ID NO: 43, wherein one of these amino acid residues may be substituted with a different amino acid; and/or a CDR3 sequence corresponding to amino acids 93-101 of SEQ ID NO: 43, wherein one or two of these amino acid residues may be substituted with a different amino acid.

A monospecific antibody of the invention which is capable of binding TFPI (182-276) may have a heavy chain comprising:

a CDR1 sequence corresponding to amino acids 31-35 of SEQ ID NO: 44, wherein one of these amino acid residues may be substituted by a different amino acid residue; and/or a CDR2 sequence corresponding to amino acids 50-66 of SEQ ID NO: 44, wherein one, two or three of these amino acids may be substituted by a different amino acid residue; and/or a CDR3 sequence corresponding to amino acids 99-109 of SEQ ID NO: 44, wherein one or two of these amino acid residues may be substituted with a different amino acid.

A monospecific antibody of the invention which is capable of binding TFPI (182-276) may have a light chain comprising:

a CDR1 sequence corresponding to amino acids 24-34 of SEQ ID NO: 45, wherein one, two or three of these amino acid residues may be substituted with a different amino acid; and/or a CDR2 sequence corresponding to amino acids 50-56 of SEQ ID NO: 45, wherein one of these amino acid residues may be substituted with a different amino acid; and/or a CDR3 sequence corresponding to amino acids 89-97 of SEQ ID NO: 45, wherein one or two of these amino acid residues may be substituted with a different amino acid.

A monospecific antibody of the invention which is capable of binding TFPI (182-276) may have a heavy chain comprising:

a CDR1 sequence corresponding to amino acids 31-36 of SEQ ID NO: 46, wherein one of these amino acid residues may be substituted by a different amino acid residue; and/or a CDR2 sequence corresponding to amino acids 51-66 of SEQ ID NO: 46, wherein one, two or three of these amino acids may be substituted by a different amino acid residue; and/or a CDR3 sequence corresponding to amino acids 99-106 of SEQ ID NO: 46, wherein one or two of these amino acid residues may be substituted with a different amino acid.

A monospecific antibody of the invention which is capable of binding TFPI (182-276) may have a light chain comprising:

a CDR1 sequence corresponding to amino acids 24-38 of SEQ ID NO: 47, wherein one, two or three of these amino acid residues may be substituted with a different amino acid; and/or a CDR2 sequence corresponding to amino acids 54-60 of SEQ ID NO: 47, wherein one of these amino acid residues may be substituted with a different amino acid; and/or a CDR3 sequence corresponding to amino acids 93-101 of SEQ ID NO: 47, wherein one or two of these amino acid residues may be substituted with a different amino acid.

A monospecific antibody of the invention which is capable of binding TFPI (182-276) may have a heavy chain comprising:
- a CDR1 sequence corresponding to amino acids 31-35 of SEQ ID NO: 60, wherein one of these amino acid residues may be substituted by a different amino acid residue; and/or
- a CDR2 sequence corresponding to amino acids 50-66 of SEQ ID NO: 60, wherein one, two or three of these amino acids may be substituted by a different amino acid residue; and/or
- a CDR3 sequence corresponding to amino acids 99-107 of SEQ ID NO: 60, wherein one or two of these amino acid residues may be substituted with a different amino acid.

A monospecific antibody of the invention which is capable of binding TFPI (182-276) may have a light chain comprising:
- a CDR1 sequence corresponding to amino acids 24-34 of SEQ ID NO: 61, wherein one, two or three of these amino acid residues may be substituted with a different amino acid; and/or
- a CDR2 sequence corresponding to amino acids 50-56 of SEQ ID NO: 61, wherein one of these amino acid residues may be substituted with a different amino acid; and/or
- a CDR3 sequence corresponding to amino acids 89-97 of SEQ ID NO: 61, wherein one or two of these amino acid residues may be substituted with a different amino acid.

Said monospecific antibodies may be combined to form a KPI-1/KPI-3 bispecific antibody.

In one embodiment a KPI-1 domain specific antibody or fragment thereof is combined with C-terminal region (182-276 according to SEQ ID NO: 1) specific antibody or fragment thereof to form a bispecific antibody in inter alia full length format or Fab-Fab conjugate.

In one such embodiment mAb 1 F91 (SEQ ID NOs: 22 and 23) or fragment thereof is combined with mAb 22F74 (SEQ ID NO: 15 and 16) or fragment thereof.

In one such embodiment mAb 1 F91 (SEQ ID NOs: 22 and 23) or fragment thereof is combined with mAb 22F132 (SEQ ID NO: 42 and 43) or fragment thereof.

In one such embodiment mAb 1 F91 (SEQ ID NOs: 22 and 23) or fragment thereof is combined with mAb 22F79 (SEQ ID NO: 44 and 45) or fragment thereof.

In one such embodiment mAb 1 F91 (SEQ ID NOs: 22 and 23) or fragment thereof is combined with mAb 41F41 (SEQ ID NO: 46 and 47) or fragment thereof.

In one such embodiment mAb 1 F91 (SEQ ID NOs: 22 and 23) or fragment thereof is combined with mAb 41F30 (SEQ ID NO: 60 and 61) or fragment thereof.

In one such embodiment mAb 2F3 (SEQ ID NOs: 24 and 25) or fragment thereof is combined with mAb 22F74 (SEQ ID NO: 15 and 16) or fragment thereof.

In one such embodiment mAb 2F3 (SEQ ID NOs: 24 and 25) or fragment thereof is combined with mAb 22F132 (SEQ ID NO: 42 and 43) or fragment thereof.

In one such embodiment mAb 2F3 (SEQ ID NOs: 24 and 25) or fragment thereof is combined with mAb 22F79 (SEQ ID NO: 44 and 45) or fragment thereof.

In one such embodiment mAb 2F3 (SEQ ID NOs: 24 and 25) or fragment thereof is combined with mAb 41F41 (SEQ ID NO: 46 and 47) or fragment thereof.

In one such embodiment mAb 2F3 (SEQ ID NOs: 24 and 25) or fragment thereof is combined with mAb 41F30 (SEQ ID NO: 60 and 61) or fragment thereof.

In one such embodiment mAb 2F22 (SEQ ID NOs: 26 and 27) or fragment thereof is combined with mAb 22F74 (SEQ ID NO: 15 and 16) or fragment thereof.

In one such embodiment mAb 2F22 (SEQ ID NOs: 26 and 27) or fragment thereof is combined with mAb 22F132 (SEQ ID NO: 42 and 43) or fragment thereof.

In one such embodiment mAb 2F22 (SEQ ID NOs: 26 and 27) or fragment thereof is combined with mAb 22F79 (SEQ ID NO: 44 and 45) or fragment thereof.

In one such embodiment mAb 2F22 (SEQ ID NOs: 26 and 27) or fragment thereof is combined with mAb 41F41 (SEQ ID NO: 46 and 47) or fragment thereof.

In one such embodiment mAb 2F22 (SEQ ID NOs: 26 and 27) or fragment thereof is combined with mAb 41F30 (SEQ ID NO: 60 and 61) or fragment thereof.

In one such embodiment mAb 2F35 (SEQ ID NOs: 28 and 29) or fragment thereof is combined with mAb 22F74 (SEQ ID NO: 15 and 16) or fragment thereof.

In one such embodiment mAb 2F35 (SEQ ID NOs: 28 and 29) or fragment thereof is combined with mAb 22F132 (SEQ ID NO: 42 and 43) or fragment thereof.

In one such embodiment mAb 2F35 (SEQ ID NOs: 28 and 29) or fragment thereof is combined with mAb 22F79 (SEQ ID NO: 44 and 45) or fragment thereof.

In one such embodiment mAb 2F35 (SEQ ID NOs: 28 and 29) or fragment thereof is combined with mAb 41F41 (SEQ ID NO: 46 and 47) or fragment thereof.

In one such embodiment mAb 2F35 (SEQ ID NOs: 28 and 29) or fragment thereof is combined with mAb 41F30 (SEQ ID NO: 60 and 61) or fragment thereof.

In one such embodiment mAb 2F45 (SEQ ID NOs: 30 and 31) or fragment thereof is combined with mAb 22F74 (SEQ ID NO: 15 and 16) or fragment thereof.

In one such embodiment mAb 2F45 (SEQ ID NOs: 30 and 31) or fragment thereof is combined with mAb 22F132 (SEQ ID NO: 42 and 43) or fragment thereof.

In one such embodiment mAb 2F45 (SEQ ID NOs: 30 and 31) or fragment thereof is combined with mAb 22F79 (SEQ ID NO: 44 and 45) or fragment thereof.

In one such embodiment mAb 2F45 (SEQ ID NOs: 30 and 31) or fragment thereof is combined with mAb 41F41 (SEQ ID NO: 46 and 47) or fragment thereof.

In one such embodiment mAb 2F45 (SEQ ID NOs: 30 and 31) or fragment thereof is combined with mAb 41F30 (SEQ ID NO: 60 and 61) or fragment thereof.

A variant antibody may comprise 1, 2, 3, 4, 5, up to 10 or more amino acid substitutions and/or deletions and/or insertions from the specific sequences and fragments discussed above. "Deletion" variants may comprise the deletion of individual amino acids, deletion of small groups of amino acids such as 1, 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 1, 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

Preferred "derivatives" or "variants" include those in which instead of the naturally occurring amino acid the amino acid which appears in the sequence is a structural analogue thereof. Amino acids used in the sequences may also be derivatized or modified, e.g. labelled, providing the function of the antibody is not significantly adversely affected.

Substitutions may be, but are not limited to, conservative substitutions.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogues thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. For example, a polynucleotide of the invention may encode a polypeptide comprising the sequence of SEQ ID NO: 11, or a variant or fragment thereof as described above. A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide encoding a polypeptide of the present invention preferably at least 80 or 90% and more preferably at least 95%, 97% or 99% homologous thereto. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example, the UWGCG Package provides the BESTFIT program which can be used to calculate homology (e.g. used on its default settings) (Devereux et al. (1984) Nucleic Acids Research 12: 387-395).

The PILEUP and BLAST algorithms can also be used to calculate homology or line up sequences (typically on their default settings), for example as described in Altschul S. F. (1993) *J Mol Evol* 36: 290-300; Altschul, S. F. et al. (1990) *J Mol Biol* 215: 403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al. supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787.

The term "antigen" (Ag) herein refers to the entity used for immunisation of an immunocompetent vertebrate to produce an antibody (Ab) that recognises the Ag. In the context of the current invention, suitable antigens include human TFPI (1-181) and full length human TFPIα. Herein, Ag is termed more broadly and is generally intended to include target molecules that are specifically recognised by the Ab, thus including fragments or mimics of the molecule used in the immunisation process, or other process, e.g. phage display, used for generating the Ab.

The term "epitope", as used herein, is defined in the context of a molecular interaction between an "antigen-binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined using various criteria (e.g. a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immunodominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The term "epitope" herein comprises both types of binding region in any particular region of TFPI that specifically binds to a mono- or bispecific TFPI antibody, or another TFPI-specific agent according to the invention, unless otherwise stated. TFPI may comprise a number of different epitopes, which may include, without limitation, (1) linear peptide epitopes (2) conformational epitopes which consist of one or more non-contiguous amino acids located near each other in the mature TFPI conformation; and (3) post-translational epitopes which consist, either in whole or part, of molecular structures covalently attached to TFPI, such as carbohydrate groups.

The epitope for a given antibody (Ab)/antigen (Ag) pair can be described and characterised at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be characterised by the spatial coordinates defining the atomic contacts between the Ag and Ab. At an even less detailed level the epitope can be characterised by the amino acid residues that it comprises as defined by a specific criteria such as the distance between or solvent accessibility of atoms in the Ab:Ag complex. At a further less detailed level the epitope can be characterised through function, e.g. by competition binding with other Abs. The epitope can also be defined more generically as comprising amino acid residues for which substitution by another amino acid will alter the characteristics of the interaction between the Ab and Ag. In the context of an X-ray derived crystal structure defined by spatial coordinates of a complex between an Ab, e.g. a Fab fragment, and its Ag, the term epitope is herein, unless otherwise specified or contradicted by context, specifically defined as being TFPI residues having a heavy atom (i.e. a non-hydrogen atom) within a distance of 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described at the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

The definition of the term "paratope" is derived from the above definition of "epitope" by reversing the perspective. Thus, the term "paratope" refers to the area or region on the Ab to which an Ag specifically binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ag residues characterised by having a heavy atom (i.e. a non-hydrogen atom) within a distance of 4 Å from a heavy atom in TFPI.

The epitope and paratope for a given antibody (Ab)/antigen (Ag) pair may be identified by routine methods. For example, the general location of an epitope may be determined by assessing the ability of an antibody to bind to different fragments or variant TFPI polypeptides. The specific amino acids within TFPI that make contact with an antibody (epitope) and the specific amino acids in an antibody that make contact with TFPI (paratope) may also be determined using routine methods. For example, the antibody and target molecule may be combined and the Ab:Ag complex may be crystallised. The crystal structure of the complex may be determined and used to identify specific sites of interaction between the antibody and its target.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes.

Adjusting the relative and absolute affinities of the two antigen recognition sites of the monospecific antibodies or the bispecific antibody for TFPI (1-181) and TFPI (182-276) may be advantageous in terms of, for example, providing selective binding to TFPIα while still providing complete blockage of TFPI inhibition.

The term "binding affinity" is herein used as a measure of the strength of a non-covalent interaction between two molecules, e.g. an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determining the equilibrium dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

An antibody according to the current invention may be able to compete with another molecule, such as a naturally occurring ligand or receptor or another antibody, for binding to TFPI and thereby affect functions associated with these interactions. The ability of an antibody to compete with a natural ligand/receptor may be assessed by various activity assays measuring the effect on the apparent $K_I$ for TFPI inhibition. $K_D$ values may then be deduced from apparent $K_I$ values. Typically, the $K_D$ value of interest for the antibody with respect to the target (TFPI) will be 2-fold, preferably 5-fold, more preferably 10-fold lower than the $K_D$ of other TFPI ligands. More preferably, the $K_D$ will be 50-fold less, such as 100-fold less, or 200-fold less; even more preferably 500-fold less, such as 1,000-fold less, or 10,000-fold less.

The value of this dissociation constant can be determined directly by well-known methods. Standard assays to evaluate the binding ability of ligands such as antibodies towards targets are known in the art and include, for example, ELISAs, Western blots, RIAs, isothermal titration calorimetry, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody.

A monospecific antibody, or any arm of a bispecific antibody of the invention, may have a $K_D$ for its target of $1\times10^{-7}$M or less, $1\times10^{-8}$M or less, or $1\times10^{-9}$M or less, or $1\times10^{-10}$M or less, $1\times10^{-11}$M or less, or $1\times10^{-12}$M or less. The $K_D$ of an antibody of the current invention may be less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM, such as less than 0.015 nM, such as between 0.015 nM and 0 nM.

In one aspect the present invention comprises antibodies that compete with the antibodies of the present invention to the extent that such competing antibodies are bispecific.

In another aspect, the present invention provides compositions and formulations comprising molecules of the invention, such as the bispecific antibodies described herein. For example, the invention provides a pharmaceutical composition that comprises one or more bispecific TFPI antibodies of the invention, formulated together with a pharmaceutically acceptable carrier.

Accordingly, one object of the invention is to provide a pharmaceutical formulation comprising such a bispecific TFPI antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabiliser, or a surfactant, as well as various combinations thereof. The use of preservatives, isotonic agents, chelating agents, stabilisers and surfactants in pharmaceutical compositions is well-known to the skilled person. Reference may be made to Remington: The Science and Practice of Pharmacy, 19th edition, 1995.

In one embodiment, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

A bispecific antibody or a pharmaceutical formulation comprising two monospecific antibodies according to the invention may be used to treat a subject with a coagulopathy.

The term "subject", as used herein, includes any human patient, or non-human vertebrate.

The term "coagulopathy", as used herein, refers to an increased haemorrhagic tendency which may be caused by any qualitative or quantitative deficiency of any pro-coagulative component of the normal coagulation cascade, or any upregulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor X deficiency, Factor XI deficiency, von Willebrand's disease and thrombocytopenias such as Glanzmann's thombasthenia and Bernard-Soulier syndrome. Said haemophilia A or B may be severe, moderate or mild. The clinical severity of haemophilia is determined by the concentration of functional units of FIX/FVIII in the blood and is classified as mild, moderate, or severe. Severe haemophilia is defined by a clotting factor level of <0.01 U/ml corresponding to <1% of the normal level, while moderate and mild patients have levels from 1-5% and >5%, respectively. Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exacerbate this situation. Said haemorrhage may be from any part of the body.

A non-limiting example of an iatrogenic coagulopathy is an overdosage of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with thrombocytopenia. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

An antibody of the invention may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

In one embodiment the bispecific antibodies of the present invention are used to measure TFPIα levels in vitro.

The following are non-limiting aspects of the invention:
1. A multispecific antibody that is capable of specifically binding tissue factor pathway inhibitor (TFPI).
2. A multispecific antibody that is capable of specifically binding a first epitope of tissue factor pathway inhibitor (TFPI) and a second epitope of TFPI, wherein the first epitope comprises an amino acid residue located within positions 1 to 181 of SEQ ID NO: 1 and the second epitope comprises an amino acid residue located within TFPI positions 182 to 276 of SEQ ID NO: 1.
3. The multispecific antibody according to aspects 1 or 2, wherein the first epitope comprises an amino acid residue within the KPI-1 domain of tissue factor pathway inhibitor (TFPI).
4. The multispecific antibody according to aspects 1 or 2, wherein the first epitope comprises an amino acid residue within the KPI-2 domain of tissue factor pathway inhibitor (TFPI).
5. The multispecific antibody according to any one of aspects 1 to 4, wherein the second epitope comprises an amino acid residue within the KPI-3 domain of tissue factor pathway inhibitor (TFPI).
6. A multispecific antibody according to any one of aspects 1 to 5 which is a bispecific antibody.
7. The bispecific antibody according to aspect 6 that is capable of specifically binding tissue factor pathway inhibitor (TFPI), wherein said antibody is capable of binding a KPI-1 epitope comprising one or more amino acid residues selected from the group consisting of Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75 of SEQ ID NO: 1
8. The bispecific antibody according to aspect 7, wherein said antibody is capable of binding a KPI-1 epitope comprising amino acid residues Arg 41, Arg 65 and/or Glu 67 of SEQ ID NO: 1.
9. A bispecific antibody according to aspect 6 that is capable of specifically binding tissue factor pathway inhibitor (TFPI), wherein said antibody is capable of binding a KPI-2 epitope comprising one or more amino acid residues selected from the group consisting of Glu 100, Glu 101, Asp 102, Pro 103, Arg 107, Tyr 109, Thr 111, Tyr 113, Phe 114, Asn 116, Gln 118, Gln 121, Cys 122, Glu 123, Arg 124, Phe 125, Lys 126 and Leu 140 of SEQ ID NO: 1.
10. The bispecific antibody according to aspect 9 that is capable of specifically binding tissue factor pathway inhibitor (TFPI) wherein said antibody is capable of specifically binding a KPI-2 epitope comprising amino acid residue Arg 107 of SEQ ID NO: 1.
11. The bispecific antibody according to any one of aspects 6 to 10 that is capable of specifically binding tissue factor pathway inhibitor (TFPI), wherein said antibody is capable of binding a KPI-3 epitope comprising one or more amino acid residues selected from the group consisting of Tyr 207, Asn 208, Ser 209, Val 210, Ile 211, Gly 212, Lys 213, Arg 215, Lys 232, Gln 233, Leu 236 and Lys 240 of SEQ ID NO: 1.
12. The bispecific antibody according to aspect 11 wherein said antibody is capable of binding a KPI-3 epitope comprising amino acid residue Ile 211, Lys 213 and/or Arg 215 of SEQ ID NO: 1.
13. The bispecific antibody according to any one of aspects 6 to 8 that is capable of specifically binding tissue factor pathway inhibitor (TFPI), wherein said antibody is capable of binding a KPI-1 epitope comprising one or more amino acid residues selected from the group consisting of Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75 of SEQ ID NO: 1; and a KPI-3 epitope comprising one or more amino acid residues selected from the group consisting of Tyr 207, Asn 208, Ser 209, Val 210, Ile 211, Gly 212, Lys 213, Arg 215, Lys 232, Gln 233, Leu 236 and Lys 240 of SEQ ID NO: 1.

14. The bispecific antibody according to any one of aspects 9 to 12 that is capable of specifically binding tissue factor pathway inhibitor (TFPI), wherein said antibody is capable of binding a KPI-2 epitope comprising one or more amino acid residues selected from the group consisting of Glu 100, Glu 101, Asp 102, Pro 103, Arg 107, Tyr 109, Thr 111, Tyr 113, Phe 114, Asn 116, Gln 118, Gln 121, Cys 122, Glu 123, Arg 124, Phe 125, Lys 126 and Leu 140 of SEQ ID NO: 1; and a KPI-3 epitope comprising one or more amino acid residues selected from the group consisting of Tyr 207, Asn 208, Ser 209, Val 210, Ile 211, Gly 212, Lys 213, Arg 215, Lys 232, Gln 233, Leu 236 and Lys 240 of SEQ ID NO: 1.

15. The bispecific antibody according to aspect 6 comprising a heavy chain comprising:
   a CDR3 sequence corresponding to amino acid residues 99 to 110 of SEQ ID NO: 3;
   and a light chain comprising:
   a CDR3 sequence corresponding to amino acid residues 94 to 102 of SEQ ID NO: 4;
   wherein one or two of the amino acid residues in the individual CDR sequences may be conservatively substituted by a different amino acid.

16. The bispecific antibody according to aspect 15, wherein the heavy chain further comprises:
   a CDR1 sequence corresponding to amino acid residues 31 to 35 of SEQ ID NO: 3; and
   a CDR2 sequence corresponding to amino acid residues 50 to 66 of a sequence selected from the group consisting of SEQ ID NO: 3 or SEQ ID NO: 5 and SEQ ID NO: 7;
   and the light chain further comprises:
   a CDR1 sequence corresponding to amino acid residues 24 to 39 of SEQ ID NO: 4; and
   a CDR2 sequence corresponding to amino acid residues 55 to 61 of SEQ ID NO: 4;
   wherein one or two of the amino acid residues in the individual CDR sequences may be conservatively substituted by a different amino acid.

17. The antibody according to aspect 6, comprising a heavy chain comprising:
   a CDR3 sequence corresponding to amino acid residues 99 to 107 of SEQ ID NO: 9;
   and a light chain comprising:
   a CDR3 sequence corresponding to amino acid residues 89 to 97 of SEQ ID NO: 10;
   wherein one or two of the amino acid residues in the individual CDR sequences may be conservatively substituted with a different amino acid.

18. The bispecific antibody according to aspect 17, wherein the heavy chain further comprises:
   a CDR1 sequence corresponding to amino acid residues 31 to 35 of SEQ ID NO: 9; and
   a CDR2 sequence corresponding to amino acid residues 50 to 66 of SEQ ID NO: 9;
   and wherein the light chain further comprises:
   a CDR1 sequence corresponding to amino acid residues 24 to 34 of SEQ ID NO: 10;
   a CDR2 sequence corresponding to amino acid residues 50 to 56 of SEQ ID NO: 10;
   wherein one or two of the amino acid residues in the individual CDR sequences may be conservatively substituted with a different amino acid.

19. The bispecific antibody according to aspect 6, comprising a heavy chain comprising:
   a CDR3 sequence corresponding to amino acid residues 99 to 106 of SEQ ID NO: 11;
   and a light chain comprising:
   a CDR3 sequence corresponding to amino acid residues 88 to 96 of SEQ ID NO: 12;
   wherein one or two of the amino acid residues in the individual CDR sequences may be conservatively substituted with a different amino acid.

20. The bispecific antibody according to aspect 19, wherein the heavy chain further comprises:
   a CDR1 sequence corresponding to amino acid residues 31 to 35 of SEQ ID NO: 11; and
   a CDR2 sequence corresponding to amino acid residues 50 to 66 of SEQ ID NO: 11;
   and wherein the light chain further comprises:
   a CDR1 sequence corresponding to amino acid residues 24 to 33 of SEQ ID NO: 12; and
   a CDR2 sequence corresponding to amino acid residues 49 to 55 of SEQ ID NO: 12;
   wherein one or two of the amino acid residues in the individual CDR sequences may be conservatively substituted with a different amino acid.

21. The bispecific antibody according to aspect 6, comprising a heavy chain comprising
   a CDR3 sequence corresponding to amino acid residues 99 to 111 of SEQ ID NO: 13;
   and a light chain comprising:
   a CDR3 sequence corresponding to amino acid residues 93 to 101 of SEQ ID NO: 14;
   wherein one or two of the amino acid residues in the individual CDR sequences may be conservatively substituted with a different amino acid.

22. The bispecific antibody according to aspect 21, wherein the heavy chain further comprises:
   a CDR1 sequence corresponding to amino acid residues 31 to 35 of SEQ ID NO: 13; and
   a CDR2 sequence corresponding to amino acid residues 50 to 66 of SEQ ID NO: 13;
   and wherein the light chain further comprises:
   a CDR1 sequence corresponding to amino acid residues 24 to 38 of SEQ ID NO: 14; and
   a CDR2 sequence corresponding to amino acid residues 54 to 60 of SEQ ID NO: 14;
   wherein one or two of the amino acid residues in the individual CDR sequences may be conservatively substituted with a different amino acid.

23. The bispecific antibody according to aspect 6, comprising a heavy chain comprising:
   a CDR3 sequence corresponding to amino acid residues 99 to 106 of SEQ ID NO: 15;
   and a light chain comprising:
   a CDR3 sequence corresponding to amino acid residues 89 to 97 of SEQ ID NO: 16;
   wherein one or two of the amino acid residues in the individual CDR sequences may be conservatively substituted with a different amino acid.

24. The bispecific antibody according to aspect 23, wherein the heavy chain further comprises:
   a CDR1 sequence corresponding to amino acid residues 31 to 35 of SEQ ID NO: 15; and a CDR2 sequence corresponding to amino acid residues 50 to 66 of SEQ ID NO: 15;
and wherein the light chain further comprises:
a CDR1 sequence corresponding to amino acid residues 24 to 34 of SEQ ID NO: 16; and
a CDR2 sequence corresponding to amino acid residues 50 to 56 of SEQ ID NO: 16;
wherein one or two of the amino acid residues in the individual CDR sequences may be conservatively substituted with a different amino acid.

25. The bispecific antibody according to aspect 6, comprising a heavy chain comprising
a CDR3 sequence corresponding to amino acid residues 98 to 110 of SEQ ID NO: 26;
and a light chain comprising:
a CDR3 sequence corresponding to amino acid residues 89 to 96 of SEQ ID NO: 27;
wherein one or two of the amino acid residues in the individual CDR sequences may be conservatively substituted with a different amino acid.

26. The bispecific antibody according to aspect 25, wherein the heavy chain further comprises:
a CDR1 sequence corresponding to amino acid residues 31 to 35 of SEQ ID NO: 26; and
a CDR2 sequence corresponding to amino acid residues 50 to 65 of SEQ ID NO: 26;
and wherein the light chain further comprises:
a CDR1 sequence corresponding to amino acid residues 24 to 34 of SEQ ID NO: 27; and
a CDR2 sequence corresponding to amino acid residues 50 to 56 of SEQ ID NO: 27;
wherein one or two of the amino acid residues in the individual CDR sequences may be conservatively substituted with a different amino acid.

27. A bispecific antibody according to aspect 6 which is in a full length antibody format.

28. A bispecific antibody according to any one of aspects 6 to 31, which is a Fab-Fab conjugate or fusion protein.

29. The Fab-Fab conjugate according to aspect 28 comprising a first Fab and a second Fab, wherein the first Fab comprises a first heavy chain (HC) and a first light chain (LC), the first heavy chain comprising:
a CDR1 sequence corresponding to amino acid residues 31 to 35 of SEQ ID NO: 3;
a CDR2 sequence corresponding to amino acid residues 50 to 66 of a sequence selected from a group consisting of SEQ ID NO: 3 or SEQ ID NO: 5 and SEQ ID NO: 7; and
a CDR3 sequence corresponding to amino acid residues 99 to 110 of SEQ ID NO: 3;
and the first light chain (LC) comprising
a CDR1 sequence corresponding to amino acid residues 24 to 39 of SEQ ID NO: 4;
a CDR2 sequence corresponding to amino acid residues 55 to 61 of SEQ ID NO: 4; and
a CDR3 sequence corresponding to amino acid residues 94 to 102 of SEQ ID NO: 4;
and the second Fab comprising a second heavy chain and a second light chain, the second heavy chain (HC) comprising:
a CDR1 sequence corresponding to amino acid residues 31 to 35 of SEQ ID NO: 9;
a CDR2 sequence corresponding to amino acid residues 50 to 66 of SEQ ID NO: 9; and
a CDR3 sequence corresponding to amino acid residues 99 to 107 of SEQ ID NO: 9;
and the second light chain (LC) comprising:
a CDR1 sequence corresponding to amino acid residues 24 to 34 of SEQ ID NO: 10;
a CDR2 sequence corresponding to amino acid residues 50 to 56 of SEQ ID NO: 10; and
a CDR3 sequence corresponding to amino acid residues 89 to 97 of SEQ ID NO: 10;
wherein one or two of the amino acid residues in the individual CDR sequences may be conservatively substituted by a different amino acid.

30. The Fab-Fab conjugate according to aspect 29 comprising a first Fab and a second Fab, wherein the first Fab fragment comprises a first heavy chain (HC) and a first light chain (LC), the first heavy chain comprising:
a CDR1 sequence corresponding to amino acid residues 31 to 35 of SEQ ID NO: 26;
a CDR2 sequence corresponding to amino acid residues 50 to 65 of SEQ ID NO: 26; and
a CDR3 sequence corresponding to amino acid residues 98 to 110 of SEQ ID NO: 26;
and the first light chain (LC) comprising:
a CDR1 sequence corresponding to amino acid residues 24 to 34 of SEQ ID NO: 27;
a CDR2 sequence corresponding to amino acid residues 50 to 56 of SEQ ID NO: 27; and
a CDR3 sequence corresponding to amino acid residues 89 to 96 of SEQ ID NO: 27;
and the second Fab fragment comprising a second heavy chain and a second light chain, the second heavy chain (HC) comprising:
a CDR1 sequence corresponding to amino acid residues 31 to 35 of SEQ ID NO: 9;
a CDR2 sequence corresponding to amino acid residues 50 to 66 of SEQ ID NO: 9; and
a CDR3 sequence corresponding to amino acid residues 99 to 107 of SEQ ID NO: 9;
and the second light chain (LC) comprising:
a CDR1 sequence corresponding to amino acid residues 24 to 34 of SEQ ID NO: 10;
a CDR2 sequence corresponding to amino acid residues 50 to 56 of SEQ ID NO: 10; and
a CDR3 sequence corresponding to amino acid residues 89 to 97 of SEQ ID NO: 10;
wherein one or two of the amino acid residues in the individual CDR sequences may be conservatively substituted by a different amino acid.

31. The multispecific or bispecific antibody according to any one of aspects 1 to 30 which is humanized.

32. A pharmaceutical composition comprising a first monospecific antibody and a second monospecific antibody, wherein the first monospecific antibody is capable of specifically binding to an epitope within tissue factor pathway inhibitor (TFPI) amino acid residues 1 to 181 of SEQ ID NO: 1;
and the second monospecific antibody is capable of specifically binding to an epitope within TFPI amino acid residues 182 to 276 of SEQ ID NO: 1.

33. The pharmaceutical composition according to aspect 32, wherein the epitope of the first antibody comprises an amino acid residue within the KPI-1 domain of tissue factor pathway inhibitor (TFPI) or within the KPI-2 domain of TFPI and wherein the epitope of the second antibody comprises an amino acid residue within the KPI-3 domain of TFPI.

34. The pharmaceutical composition according to aspect 33, wherein the first monospecific antibody comprises a heavy chain (HC) comprising:

a CDR3 sequence corresponding to amino acid residues 98 to 110 of SEQ ID NO: 26;
and a light chain (LC) comprising:
a CDR3 sequence corresponding to amino acid residues 89 to 96 of SEQ ID NO: 27;
wherein one or two of the amino acid residues in the individual CDR sequences may be conservatively substituted with a different amino acid.

35. The pharmaceutical composition according to aspect 33, wherein the second monospecific antibody comprises a heavy chain (HC) comprising:
a CDR3 sequence corresponding to amino acid residues 99 to 107 of SEQ ID NO: 9;
and a light chain (LC) comprising:
a CDR3 sequence corresponding to amino acid residues 89 to 97 of SEQ ID NO: 10;
wherein one or two of the amino acid residues in the individual CDR sequences may be conservatively substituted with a different amino acid.

36. The pharmaceutical composition according to aspect 35, wherein the second monospecific antibody comprises a heavy chain (HC) further comprising:
a CDR1 sequence corresponding to amino acid residues 31 to 35 of SEQ ID NO: 9; and
a CDR2 sequence corresponding to amino acid residues 50 to 66 of SEQ ID NO: 9;
and the second monospecific antibody comprises a light chain (LC) further comprising
a CDR1 sequence corresponding to amino acid residues 24 to 34 of SEQ ID NO: 10; and
a CDR2 sequence corresponding to amino acid residues 50 to 56 of SEQ ID NO: 10;
wherein one or two of the amino acid residues in the individual CDR sequences may be conservatively substituted with a different amino acid.

37. A multispecific or bispecific antibody or a pharmaceutical composition comprising monospecific antibodies that compete with the multispecific or bispecific antibody or pharmaceutical composition comprising a combination of monospecific antibodies according to any one of the former aspects.

38. A pharmaceutical composition comprising the multispecific or bispecific antibody according to any one of aspects 1 to 31.

39. The multispecific or bispecific antibody according to any one of aspects 1 to 31 or 37 or the pharmaceutical composition comprising a combination of monospecific antibodies according to any one of aspects 32 to 37 for use as a medicament.

40. The multispecific or bispecific antibody according to any one of aspects 1 to 19 or 37 or the pharmaceutical composition comprising a combination of monospecific antibodies according to any one of aspects 32 or 37 for use in the treatment of coagulopathy.

41. A eukaryotic cell which expresses the bispecific antibody according to any one of aspects 1 to 31 or a fragment thereof.

42. Use of the bispecific antibodies according any one of aspects 6 to 31 for measuring TFPIα levels in vitro.

43. A bispecific antibody according to any one of aspects 1 to 37 which selectively target circulating TFPIα.

EXAMPLES

Example 1

Immunisation, Fusion and Screening

RBF mice were immunised with human TFPIα (SEQ ID NO: 1) or a TFPI fragment, e.g. corresponding to residues 1-161 of SEQ ID NO: 1. Mice were injected subcutaneously: 20'4 human TFPI was mixed with complete Freund's adjuvant for the first injection. For subsequent immunisations, incomplete Freund's adjuvant was used with the same concentration of the antigen. Ten days after the final immunisation, eye-blood from mice was screened, using ELISA, for human TFPI specific antibodies. Mice with positive serum titres were boosted with 10 μg of human TFPIα or TFPI (1-161) by intravenous injection and sacrificed after three days. The spleens were removed aseptically and dispersed to a single cell suspension. Fusion of spleen cells and myeloma cells was done by means of the PEG-method or by electrofusion. The resulting hybridoma cells were cloned by limiting dilution into microtiter plates. Supernatants from individual hybridomas were initially screened by ELISA for expression of antibodies capable of binding to full-length TFPIα or TFPI fragments.

Antibodies were purified from supernatants by standard protein A affinity chromatography and used to determine binding and affinity to human TFPI and TFPI neutralising activity in plasma (dilute prothrombin time). Hybridomas producing antibodies of interest were subcloned by limited dilution and the original antibody profile was verified for material from subcloned hybridomas. Cells from subcloned hybridomas were used for isolation of RNA and subsequent antibody cloning and sequence identification.

Example 2

Cloning and Sequencing of Mouse Anti-TFPI KPI-3/C-terminal Specific mAbs TFPI4F110, TFPI22F66 and TFPI22F71

The murine heavy chain and light chain sequences of TFPI antibodies: TFPI4F110, TFPI22F66 and TFPI22F71 were cloned and sequenced as described in WO2012/001087.

Total RNA was extracted from hybridoma cells using the RNeasy-Mini Kit from Qiagen and used as a template for cDNA synthesis. cDNA was synthesised in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. A reverse primer with the following sequence was used for HC (VH domain) amplification:

(SEQ ID NO: 17)
5'-CTTGCCATTGAGCCAGTCCTGGTGCATGATGG-3'

A reverse primer with the following sequence was used for TFPI22F66 and TFPI22F71 LC (VL domain) amplification:

(SEQ ID NO: 18)
5'-GTTGTTCAAGAAGCACACGACTG-3'

A reverse primer with the following sequence was used for TFPI4F110 LC amplification:

(SEQ ID NO: 19)
5'-GCTCTAGACTAACACTCATTCCTGTTGAAGCTCTTG-3'

PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 E. coli (Invitrogen). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at Eurofins MWG Operon, Germany using M13uni(-21)/M13rev(-29) sequencing primers. Sequences were analyzed and annotated using the VectorNTI program. All kits and reagents were used according to the manufacturer's instructions.

A single unique murine kappa type LC and a single unique murine HC, subclass IgG1 was identified for each of the hybridomas: TFPI4F110, TFPI22F66 and TFPI22F71. Amino acid sequences are provided in the sequence list: the leader peptide sequences are not included.

Example 3

Cloning and Sequencing of Mouse Anti-TFPI KPI-3/C-terminal Specific mAb 22F74, 41F41, 41F30, 22F132, 22F79 and Cloning and Sequencing of Mouse Anti-TFPI KPI-1 mAb 2F3, 2F22, 2F45, 1F91 and 2F35

The murine heavy chain and light chain sequences of anti-TFPI antibodies were cloned and sequenced as follows.

Total RNA was extracted from hybridoma cells using the RNeasy-Mini Kit from Qiagen and used as template for cDNA synthesis. cDNA was synthesised in a 5'-RACE reaction using either the SMART™ or SMARTer™ RACE cDNA amplification kit from Clontech. Subsequent target amplification of HC and LC sequences was performed by PCR using Phusion Hot Start polymerase (Finnzymes) and the universal primer mix (UPM) included in the SMART™/SMARTer™ RACE kit as forward primer. A reverse primer with the following sequence was used for HC (VH domain) amplification:

(SEQ ID NO: 20)
5'-CCCTTGACCAGGCATCCCAG-3'

A reverse primer with the following sequence was used for LC amplification:

(SEQ ID NO: 21)
5'-GCTCTAGACTAACACTCATTCCTGTTGAAGCTCTTG-3'

PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 E. coli (Invitrogen). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at Eurofins MWG Operon, Germany using M13uni(-21)/M13rev(-29) sequencing primers. Sequences were analyzed and annotated using the VectorNTI program. All kits and reagents were used according to the manufacturer's instructions.

A single unique murine kappa type LC and a single unique murine IgG HC, subclass was identified for each hybridoma. Amino acid sequences are provided in the sequence list: the leader peptide sequences are not included.

Example 4

Cloning and Engineering of mAb 2021 and mAb 2021 Variants

This example describes cloning and engineering of anti-TFPI antibody: mAb2021 and variants thereof.

Total RNA was extracted from M-hTFPI 4F36A1 B2 hybridoma cells using the RNeasy-Mini Kit from Qiagen and used as template for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. A reverse primer with the following sequence was used for HC (VH domain) amplification:

(SEQ ID NO: 20)
5'-CCCTTGACCAGGCATCCCAG-3'

A reverse primer with the following sequence was used for LC amplification:

(SEQ ID NO: 21)
5'-GCTCTAGACTAACACTCATTCCTGTTGAAGCTCTTG-3'

PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 E. coli (Invitrogen). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at Eurofins MWG Operon, Germany using either M13uni(-21)/M13rev(-29) or T3/T7 sequencing primers. Sequences were analyzed and annotated using the VectorNTI program. All kits and reagents were used according to the manufacturer's instructions.

A single unique murine kappa type LC and a single unique murine HC, subclass IgG1 was identified.

Generation of Expression Vectors for the Grafted Anti-HzTFPI4F36A1B2

A series of CMV promotor-based based expression vectors (pTT vectors) were generated for transient expression of anti-TFPI antibody/antibody fragment in the HEK293-6E EBNA-based expression system developed by Yves Durocher (Durocher et al. Nucleic Acid Research, 2002). In addition to the CMV promotor, the pTT-based vectors contain a pMB1 origin, an EBV origin and the Amp resistance gene.

Based on the cloned murine anti-TFPI4F36A1B2 VH and VL sequences a humanized version of anti-TFPI4F36 was designed by CDR grafting on human germline sequences. DNA sequences for grafted HzTFPI4F36 VH and VL regions were synthesized (GENEART AG) according to the humanization design of the antibody described above. The sequences were obtained with the basic minimal CDR grafting and no additional back mutations. The respective LC and HC germline leader peptide sequences were include in the constructs as well as a Kozak sequence (5'-GCCGC-CACC-3') immediately upstream of the ATG start codon.

pTT-based expression vectors were generated for transient expression of the grafted TFPI4F36 antibody as a human kappa/IgG4(S241P) isotype. The proline mutation at position 241 (numbering according to Kabat, corresponding to residue 228 per the EU numbering system (Edelman G. M. et AL., Proc. Natl. Acad. USA 63, 78-85 (1969)) was introduced in the IgG4 hinge region to eliminated formation of monomeric antibody fragments, i.e. "half-antibodies" comprised of one LC and one HC.

The VH fragment was excised from the GENEART cloning vector and cloned into a linearized pTT-based vector containing the sequence for a human IgG4(S241P) CH domain and subsequently transformed into E. coli for selection. The sequence of the final construct was verified by DNA sequencing. The VL fragment was excised from the GENEART cloning vector and cloned into a linearized pTT-based vector containing the sequence for a human kappa CL domain and subsequently transformed into E. coli for selection. The sequence of the final constructs was verified by DNA sequencing.

Site-directed Mutagenesis to Isolate mAb 2021

A series of human-to-mouse reverse mutation (referred to as back mutations) were generated in the light chain (LC) and heavy chain (HC) of the grafted HzTFPI4F36.

Site-directed mutagenesis was performed to introduce human-to-mouse reverse mutations (henceforth referred to as back mutations) at the specific residues in the grafted HzTFPI4F36 LC/HC constructs to optimize the grafted constructs. Mutations were introduced by two different methods:

1. QuikChange® Site-Directed or Multi Site-Directed Mutagenesis kits from Stratagene were used to introduce point mutations and combination mutations. The kits were used according to the manufacturer's protocol.

2. Standard 2-step overlapping PCR methods were also used to introduce point mutations and to generate combination mutations.

The LC and HC expression plasmids for grafted HzTFPI4F36 were used as templates for the mutagenesis. The sequences of all final constructs were verified by DNA sequencing.

The final sequences for mAb 2021 HC carries a FR2 region with 4 back mutations rendering the framework sequence identical to original mouse FR2 and 3 CDR2 mutants, i.e. a total of 7 HC back mutations (A40T, G42E, G44R, S49A, Y59F, A60P, K64Q) compared to the original grafted sequence (numbering according to Kabat). The LC sequence is the grafted HzTFPI4F36 LC sequence. CDRs and frameworks defined according to Kabat.

The amino acid sequences for the HC and LC of the final mAb 2021 are listed as SEQ ID NO: 50 and SEQ ID NO: 51, respectively.

In order to improve the expression yield the original signal peptide sequences (human germline sequence) for both HC and LC, were exchanged for the human CD33 signal peptide (SP). The signal peptide sequences were exchanged by standard PCR amplification of the HC or LC fragment with primers containing a Kozak element (GC-CGCCACC), start codon and the CD33 signal sequence (sense primer) and stop codon and EcoRI restriction site (anti-sense primer). The amplified fragments were cloned into linearized pTT-based vectors and transformed into E. coli for selection. The sequence of the final construct was verified by DNA sequencing.

Generation of Lower Affinity Variants of mAb 2021

During humanization of anti-TFPI4F36A1 B2 to obtain mAb 2021 a number of lower affinity variants were identified. The variants were generated as described above by site-directed mutagenesis. mAb 2007 and mAb 2014 were two such lower affinity variants. mAb 2007 carries a single A60P back mutations in the VH domain compared to the sequence for the grafted HzTFPI4F36 (numbering according to Kabat). Compared to the sequence for the grafted HzTFPI4F36, mAb 2014 carries a FR2 region with 4 back mutations (Y36L, K39R, Q42E, Q45K) in the VL domain, rendering the framework sequence identical to original mouse FR2 (numbering according to Kabat). The heavy chain of mAb 2014 corresponds to the grafted HzTFPI4F36. The two variants have TFPI binding affinities that are lower by at least one or two orders of magnitude, respectively compared to mAb 2021. The initial grafted HzTFPI4F36 variant (mAb 2000) exhibited TFPI binding affinities approximately three orders of magnitude lower compared to mAb 2021.

Expression vectors for expression of Fab fragments of mAb 2021 and mAb 2021 variants were generated as described in example 6. The IgG4-based HC was truncated in the hinge region after the cysteine corresponding to position 227 in the HC sequence for mAb 2021, SEQ. ID. NO: 50. The truncation leaves the C-terminal cysteine available for chemical conjugation. The Fab fragment of mAb 2007 was expressed as Fab 0094, using the mAb 2021 LC vector and the truncated mAb 2007 HC vector described above. The Fab fragment of mAb 2014 was expressed as Fab 0095, using the mAb 2014 LC vector and the truncated mAb 2014 HC vector described above. The Fab fragment of mAb 2000 was expressed as Fab 0313, using the mAb 2021 LC vector and the truncated HC for the grafted HzTFPI4F36.

Example 5

Generation of Expression Vectors for Mouse/Human Chimeric TFPI4F110, TFPI22F66, TFPI22F71 TFPI2F22 mAbs A series of CMV promoter-based expression vectors (pTT vectors) were generated for transient expression of a mouse/human chimeric anti-TFPI antibody/antibody fragment in the HEK293-6E EBNA-based expression system developed by Yves Durocher (Durocher et al. Nucleic Acid Research, 2002) or the EXPI293F system from Invitrogen. In addition to the CMV promoter, the pTT-based vectors contain a pMB1 origin, an EBV origin and the Amp resistance gene. The anti-TFPI antibody variants including Fab fragments were expressed transiently in HEK293-6E or EXPI293F cells by co-transfection of LC and HC expression vectors as described in example 7. pTT-based LC expression vectors were generated for transient expression of chimeric anti-TFPI mAb and Fab fragments. Initially, the region corresponding to the VL domains of either TFPI4F110, TFPI22F66, TFPI22F71 or TFPI2F22 were PCR amplified in a 2-step reaction from an original TOPO sequencing clone, using primers specific for the N and C-terminal sequences. The original murine signal peptide was exchanged for the human CD33 signal peptide by 2-step overlapping PCR. The primary sense primers carries the C-terminal part of the CD33 signal peptide sequence and the secondary sense primer contained a HindIII restriction site for cloning purposes, a Kozak sequence (5'-GCCGCCACC-3') immediately upstream of the ATG start codon and the N-terminal part of the CD33 signal peptide sequences. The anti-sense primer contained an in-frame BsiWI restriction site in the VL/CL transition sequence.

The amplified fragments were cloned into a linearised pTT-based vector containing the sequence for a human kappa CL domain and subsequently transformed into *E. coli* for selection. The sequence of the final construct was verified by DNA sequencing.

pTT-based HC expression vectors were generated for transient expression of chimeric anti-TFPI mAbs. Initially, the region corresponding to the VH domains of either TFPI4F110, TFPI22F66, TFPI22F71 or TFPI2F22 were PCR amplified in a 2-step reaction from an original TOPO sequencing clone, using primers specific for the N- and C-terminal sequences. The original murine signal peptide was exchanged for the human CD33 signal peptide by 2-step overlapping PCR. The primary sense primers carries the C-terminal part of the CD33 signal peptide sequence and the secondary sense primer contained a HindIII restriction site for cloning purposes, a Kozak sequence (5'-GCCGCCACC-3') immediately upstream of the ATG start codon and the N-terminal part of the CD33 signal peptide sequences. The anti-sense primer contained an in-frame NheI restriction site at the VH/CH transition.

The generated VH domain PCR fragment was restriction digested and cloned into a linearised pTT-based vector containing the sequence of an engineered human IgG4(S241 P) CH domain and subsequently transformed into *E. coli* for selection. The proline mutation at position 241 (numbering according to Kabat, corresponding to residue 228 per the EU numbering system (Edelman G. M. et al., *Proc. Natl. Acad. USA* 63: 78-85 (1969))) in the IgG4 hinge region was introduced to eliminated formation of monomeric antibody fragments, i.e. "half-antibodies" comprised of one LC and one HC. The sequence of the final construct was verified by DNA sequencing.

The chimeric version of TFPI4F110 was expressed recombinantly as mAb 4F110, using the TFPI4F110 LC and HC vectors.

The chimeric version of TFPI22F66 was expressed recombinantly as mAb 22F66, using the TFPI22F66 LC and HC vectors.

The chimeric version of TFPI22F71 was expressed recombinantly as mAb 22F71, using the TFPI22F71 LC and HC vectors.

The chimeric version of TFPI2F22 was expressed recombinantly as mAb 2F22, using the TFPI2F22 LC and HC vectors.

Example 6

Fab Components for Bispecific Molecules

To generate Fab fragments suitable for Fab-Fab chemical conjugates, an expression vector for expression of a truncated mAb 4F110 HC was generated. The IgG4-based HC of mAb 4F110 was truncated in what corresponds to the hinge region after the cysteine in position 227 in the human IgG4 constant region (numbering according to SEQ ID NO: 50). The truncation leaves the C-terminal cysteine available for chemical conjugation. The truncated sequence was generated by introducing a stop codon after the cysteine residue by site-directed mutagenesis using the QuikChange® Site-Directed mutagenesis kit from Stratagene. The sequences of the final constructs were verified by DNA sequencing. The Fab fragment of mAb 4F110 was expressed as Fab 0089, using the mAb 4F110 LC vector and the truncated HC vector described above (SEQ ID NO: 9 and SEQ ID NO: 10).

For Fab-Fab chemical conjugates, an expression vector for expression of a truncated mAb 2021 HC was also generated. Cloning, humanisation and expression of mAb 2021 is described in WO2010/072691, which is hereby incorporated by reference. The IgG4-based HC of mAb 2021 was truncated in the hinge region after the cysteine in position 227 in the human IgG4 constant region of mAb 2021 HC, SEQ ID no: 50. The truncation leaves the C-terminal cysteine available for chemical conjugation. The truncated sequence was generated by introducing a stop codon after the cysteine residue by site-directed mutagenesis using the QuikChange® Site-Directed mutagenesis kit from Stratagene. The sequences of all final constructs were verified by DNA sequencing. The Fab fragment of mAb2021 was expressed as Fab 0088, using the mAb 2021 LC vector and the truncated HC vector described above (SEQ ID NO: 3 and SEQ ID NO: 4).

Heavy chain expression vectors for expression of lower affinity variants of mAb 2021 were also generated. The mAb 2021 variants originate from the humanisation of mAb 2021 and are described in WO2010/072691. The IgG4-based HCs were truncated in the hinge region after the cysteine corresponding to position 227 in the human IgG4 constant region of mAb 2021 HC, SEQ ID no: 50. The truncation leaves the C-terminal cysteine available for chemical conjugation. To assemble the expression vectors, the region corresponding to the VH domain of the HCs of mAb 2000, mAb2007 and mAb2014 described in example 4 were cloned using standard restriction enzyme based cloning into a linearised pTT-based toolbox vector containing the sequence of the truncated human IgG4 CH domain. The IgG4-based HCs were truncated in the hinge region after the cysteine in position 227 as described above. The sequences of the final constructs were verified by DNA sequencing. The lower affinity Fab fragments of mAb2007, mAb 20014 and mAb 2000 were expressed as Fab 0094 (SEQ ID NO: 5 and SEQ ID NO: 6), Fab 0095 (SEQ ID NO: 7 and SEQ ID NO: 8) and Fab 0313 (SEQ ID NO: 58 and SEQ ID NO: 59), respectively.

The above described method for generation of truncated HC expression vectors for Fab 0094, 0095, 0313 was also used in the generation of other Fab fragments of the present invention such as Fab 2F22 (SEQ ID NO: 40 and SEQ ID NO: 41).

Example 7

Expression and Purification of mAbs and Fabs

The anti-TFPI antibody variants including Fab fragments were expressed transiently in suspension cultures of either HEK293-6E cells or EXPI293F cells, by co-transfection of LC and HC expression vectors. The following procedures describes the generic transfection protocol used for suspension adapted HEK293-6E cells or EXPI293F cells.

HEK293-6E Protocol

HEK293-6E cells were grown in suspension in FreeStyle™ 293 expression medium (Gibco) supplemented with 25 μg/ml Geneticin (Gibco), 0.1% v/v of the surfactant Pluronic F-68 (Gibco) & 1% v/v Penicillin-Streptomycin (Gibco). Cells were cultured in Erlenmeyer shaker flasks in shaker incubators at 37° C., 8% $CO_2$ and 125 rpm and maintained at cell densities between $0.1$-$1.5 \times 10^6$ cells/ml.

HEK293-6E Transfection

The cell density of cultures used for transfection was $0.9$-$2.0 \times 10^6$ cells/ml.

A mix of 0.5 μg LC vector DNA+0.5 μg HC vector DNA was used per ml cell culture.

The DNA was diluted in Opti-MEM media (Gibco) 30 μl media/μg DNA, mixed and incubated at room temperature (23-25° C.) for 5 min.

293Fectin™ (Invitrogen) was used as transfection reagent at a concentration of 1 μl per μg DNA.

The 293Fectin™ was diluted 30× in Opti-MEM media (Gibco), mixed and incubated at room temperature (23-25° C.) for 5 min.

The DNA and 293Fectin solutions were mixed and left to incubate at room temperature (23-25° C.) for 25 min.

The DNA-293Fectin mix was then added directly to the cell culture.

The transfected cell culture was transferred to a shaker incubator at 37° C., 8% $CO_2$ and 125 rpm.

3-6 days post transfection, cell culture supernatants were harvested by centrifugation, followed by filtration through a 0.22 μm PES filter (Corning).

Quantitative analysis of antibody production was performed by Biolayer Interferometry directly on clarified cell culture supernatants using the ForteBio Octet system and protein A biosensors or quantitative protein A HPLC.

EXPI293F protocol

EXPI293F cells were grown in suspension in Expi293™ expression medium (Life Technologies). Cells were cultured in Erlenmeyer shaker flasks in an orbital shaker incubator at 36.5° C., 8% $CO_2$ and 85-125 rpm and maintained at cell densities between 0.4-4×10⁶ cells/ml.

EXPI293F Transfection

1) Separate dilutions of DNA and transfection reagent are initially prepared.
  a) Use a total of 1 μg of vector DNA (0.5 ug LC vector and 0.5 ug HC vector) per ml cell culture. Dilute the DNA in Opti-MEM media (Gibco) 50 μl medium/μg DNA, mix and incubate at room temperature (23-25° C.) for 5 min.
  b) Use Expifectamin™ 293 (Life Technologies) as transfection reagent at a concentration of 2.7 μl per μg DNA. Dilute the Expifectamin™ solution 18.5× in Opti-MEM media (Gibco), mix and incubate at room temperature (23-25° C.) for 5 min.
2) Mix DNA and Expifectamin™ 293 dilutions and leave to incubate at room temperature (23-25° C.) for 10 min.
3) Add the DNA-Expifectamin™ 293 mix directly to the EXPI293F cell culture.
  a) At the time of transfection the cell density of the EXPI293F culture should be 2.8-3.2×10⁶ cells/ml.
4) Transfer the transfected cell culture to an orbital shaker incubator at 36.5° C., 8% $CO_2$ and 85-125 rpm.
5) 18 hrs post transfection, add 5 ul Expifectamin™ 293 Transfection Enhancer1/ml culture and 50 ul Expifectamin™ 293 Transfection Enhancer2/ml culture and return culture to an orbital shaker incubator at 36.5° C., 8% $CO_2$ and 85-125 rpm.
6) 5 days post transfection, cell culture supernatants were harvested by centrifugation, followed by filtration through a 0.22 μm PES filter unit (Corning).

General Purification Protocol mAb variants were purified by standard affinity chromatography using MabSelectSuRe resin from GE Healthcare according to manufacturer's instructions. The purified antibodies were buffer exchanged to PBS buffer pH7.2.

Fab fragments were purified by standard affinity chromatography using KappaSelect resin developed by GE Healthcare. The purified Fab fragments were buffer exchanged to PBS buffer pH7.2.

Quality assessment and concentration determination was done by SEC-HPLC.

Example 8

Conjugation of Fab 0088 and Fab 0089 with 1,8-N,N'-bis(maleimido)-3,6-dioxaoctane (Ref. 9000)

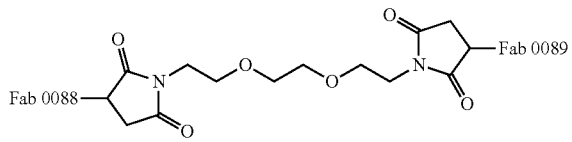

Fab 0088 (Fab fragment of mAb 2021) (5 mg, 3.92 mg/ml, 0.104 mmol) in PBS buffer was mixed with a solution of Tris(3-sulfonatophenyl)phosphine hydrate sodium salt (3.2 ml, 10 mg/ml, technical grade, (Alfa Aesar #39538, CAS: 63995-70-0). The reaction was left for 1 hour and 30 minutes at ambient temperature. The mixture was subjected to buffer exchange into 50 mM acetate buffer (dilute acetic acid adjusted to pH 5 with sodium hydroxide; buffer A) using an Amicon Ultra centrifugal filter device (5 kDa MWCO, Millipore). The protein was immobilised on a preconditioned HiTrap SP HP column (GE Healthcare) and eluted with a gradient in which buffer B was buffer A containing 300 mM sodium chloride.

The eluted protein (3 ml, 0.6 mg) was mixed with a solution of 1,8-N,N'-bis(maleimido)-3,6-dioxaoctane (Thermo Scientific/Pierce, product no. 22336; 6.2 mg in 2 ml buffer). The resulting mixture was incubated at ambient temperature for 2.5 hours. The mixture was subjected to buffer exchange into 50 mM acetate buffer (dilute acetic acid adjusted to pH 5 with sodium hydroxide; buffer A) using an Amicon Ultra centrifugal filter device (5 kDa MWCO, Millipore). The protein was immobilised on a preconditioned HiTrap SP HP column (GE Healthcare) and eluted with a gradient in which buffer B was buffer A containing 300 mM sodium chloride.

Fab 0089 (Fab fragment of mAb 4F110) (5 mg, 3.58 mg/ml, 0.105 mmol) in PBS buffer was mixed with a solution of Tris(3-sulfonatophenyl)phosphine hydrate sodium salt (3.2 ml, 10 mg/ml, technical grade, (Alfa Aesar #39538, CAS: 63995-70-0).

The reaction was left for 2 hours and 15 minutes at ambient temperature. The mixture was subjected to buffer exchange into 50 mM acetate buffer (dilute acetic acid adjusted to pH 5 with sodium hydroxide; buffer A) using an Amicon Ultra centrifugal filter device (5 kDa MWCO, Millipore). The protein was immobilised on a preconditioned HiTrap SP HP column (GE Healthcare) and eluted with a gradient in which buffer B was buffer A containing 300 mM sodium chloride.

The two solutions (Fab 0088 reduced and coupled to linker, 4 ml; and Fab 0089, reduced, 4 ml) were mixed. The resulting mixture was left at ambient temperature overnight. The solution was concentrated and loaded onto a Superdex200 10/300 GL column (GE Healthcare) using an Äkta FPLC instrument and eluted in buffer (9.7 mM Histidin, 2.3 mM $CaCl_2$, 308 mM NaCl, 8.8 mM Sucrose, 0.01% Tween 80, pH 7.0). The isolated fractions were analysed by SDS-PAGE analysis, analytical size exclusion chromatography, and Edman sequence determination.

Example 9

Preparation of 1,16-N,N'-bis(maleimido)-4,13-diaza-7,10-dioxa-3,14-dioxohexadecane

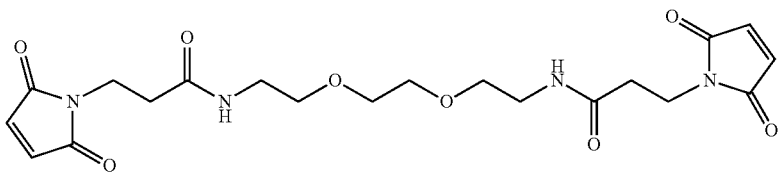 [SMILES: O=C(CCN1C(=O)C=CC1=O)NCCOCCOCCNC(=O)CCN1C(=O)C=CC1=O]

N-Maleoyl-β-alanine (1.26 g, 7.4 mmol) was dissolved in DCM (20 ml). N,N'-diisopropylcarbodiimide (1.15 ml, 7.4 mmol) was added. The mixture was stirred for 30 minutes. A solution of 1,8-diamino-3,6-dioxaoctane in DCM was added dropwise to the stirring solution over a period of 60 minutes. The mixture was stirred for 1 h. The solution was concentrated in vacuo to dryness. The crude solids were suspended in water/MeCN (2:1) with some acetic acid present. The mixture was purified using RP HPLC (0-50% MeCN in water, 0.1% TFA, $C_{18}$ column). The product was characterised by LCMS (ESI): 451 ([M+H]$^+$:) and NMR.

Example 10

Conjugation of Fab 0088 and Fab 0089 with 1,16-N,N'-bis(maleimido)-4,13-diaza-7,10-dioxa-3,14-dioxohexadecane (Ref. 9002)

Fab 0089 (5 mg, 3.58 mg/ml, 1.42 ml, 104 nmol) was buffer exchanged into 25 mM sodium phosphate buffer, pH 7. The final volume was 2000 microliter (50 micromolar, 2.5 mg/ml). Bis(p-sulfonatophenyl)phenylphospine dihydrate dipotassium salt from a solution in the phosphate buffer was added to an end-concentration of 200 micromolar (Bis(p-sulfonatophenyl)phenylphosphine dipotassium dihydrate salt, CAS: 151888-20-9, Sigma-Aldrich; 2.24 mg, 4.19 micromol) was dissolved in 1 ml 25 mM sodium phosphate buffer, pH 7 resulting in a concentration of 4.19 mM (dilution factor: 20.9); 95 microliter was added to the protein solutions. (2000 microliter total volume).

1,16-N,N'-bis(maleimido)-4,13-diaza-7,10-dioxa-3,14-dioxohexadecane (5 mg, 11 micromol) was added to the solution. The mixture was incubated at ambient temperature for 45 minutes.

The sample was diluted with 5 mM acetate buffer, pH 5. The sample was loaded onto a HiTrap SP HP column (1 ml). The column was washed with 5 mM acetate and 25 mM acetate buffer. The compound was eluted with 25 mM acetate buffer containing 1 M NaCl.

Fab 0088 (5 mg, 3.92 mg/ml, 1.27 ml, 104 nmol) was buffer exchanged into 25 mM sodium phosphate buffer, pH 7. The final volume was 2000 microliter (50 micromolar, 2.5 mg/ml). Bis(p-sulfonatophenyl)phenylphospine dihydrate dipotassium salt from a solution in the phosphate buffer was added to an end-concentration of 200 micromolar (Bis(p-sulfonatophenyl)phenylphosphine dipotassium dihydrate salt, CAS: 151888-20-9, Sigma-Aldrich; 2.24 mg, 4.19 micromol) was dissolved in 1 ml 25 mM sodium phosphate buffer, pH 7 resulting in a concentration of 4.19 mM (dilution factor: 20.9); 95 microliter was added to the protein solutions (2000 microliter total volume).

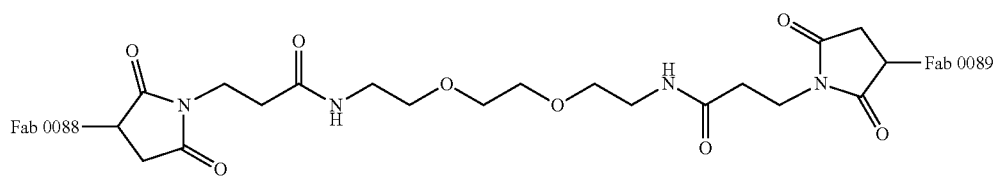

The two protein solutions were mixed, buffer exchanged to 25 mM acetate buffer, pH 5, and concentrated to half the volume. The mixture was incubated at ambient temperature for 3 hours. The solution was loaded onto a Superdex200 10/300 GL column that had been preconditioned in 10 mM L-Histidine, 150 mM NaCl, pH 7. The compound was eluted using said buffer. The selected fractions were pooled and analysed using SDS-PAGE analysis, LCMS (m/z: 96144, [M-NH$_3$+H]$^+$), Reversed phase HPLC, and Edman sequence determination. This conjugate was designated 9002.

Example 11

Conjugation of Fab 2F22 and Fab 0089 with 1,16-N,N'-bis(maleimido)-4,13-diaza-7,10-dioxa-3,14-dioxohexadecane (Ref. 9028)

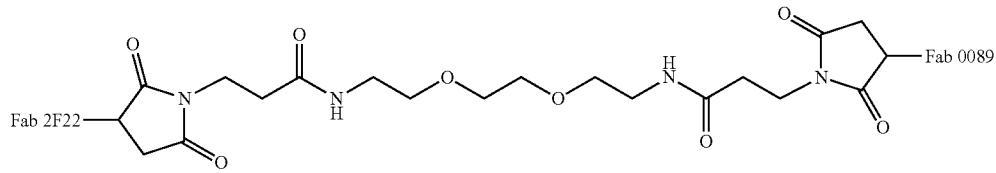

In complete analogy with the example above, Fab 2F22 (3.9 mg) and Fab 0089 (8.0 mg) were buffer-exchanged to phosphate buffered saline using an Amicon Ultra centrifugal device (Millipore Corp., 10 kDa MWCO). The concentrations of both proteins were adjusted to 50 micromolar.

Bis(p-sulfonatophenyl)phenylphospine dihydrate dipotassium salt from a solution in the phosphate buffer was added to an end-concentration of 200 micromolar. The resulting mixtures were incubated over night at room temperature. Fab 2F22 was buffer-exchanged into 15 mM sodium acetate buffer, 1 M sodium chloride, pH 5.0.

Fab 0089 was buffer-exchanged into 15 mM sodium acetate buffer, pH 4.5. 1,16-N,N'-bis(maleimido)-4,13-diaza-7,10-dioxa-3,14-dioxohexadecane (tip of a spatula) was added to the solution. The resulting mixture was kept at room temperature for 30 minutes. The mixture was loaded onto a preconditioned HiTrap SP HP column (GEHealthcare, 1 ml). The immobilised protein was washed with 15 mM sodium acetate buffer, pH 4.5, 25 CV. The protein was eluded from the column with 15 mM sodium acetate buffer, 1 M NaCl, pH 5.0 and mixed with Fab 2F22. The resulting mixture was concentrated in Amicon Ultra centrifugal spin filter (MWCO 10 kDa). End volume: 400 microliter. The mixture was incubated for 20 h. The sample was injected on gel-permeation column that had been pre-conditioned in 5 mM HEPES, 150 mM NaCl, pH 7.3 (HiLoad16/600 Superdex 200 column, GE Heathcare). Using a flow of 1 ml/min of 5 mM HEPES, 150 mM NaCl, pH 7.3 in water, the sample was eluded from the column. The fractions containing the desired conjugate were identified using SDS-PAGE analysis. The pooled fractions were concentrated to a volume of 1000 microliter using an Amicon Ultra Centrifugal device (MWCO 10 kDa). LCMS (m/z: 95629, [M+H]$^+$). This conjugate was designated 9028.

Example 12

Conjugation of Fab 0094 and Fab 0089 with 1,16-N,N'-bis(maleimido)-4,13-diaza-7,10-dioxa-3,14-dioxohexadecane (Ref. 9004)

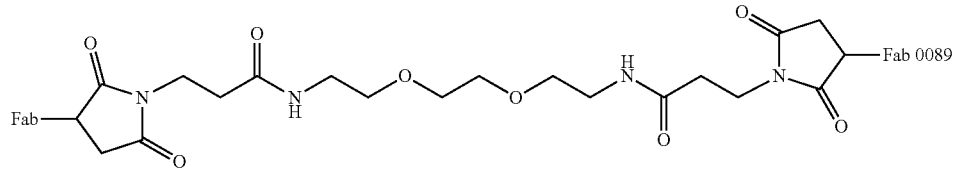

In complete analogy with the example above, a conjugate of Fab 0094 and Fab 0089 was formed. LCMS (m/z: 95994, [M+H]$^+$). This conjugate was designated 9004.

Example 13

Conjugation of Fab 0095 and Fab 0089 with 1,16-N,N'-bis(maleimido)-4,13-diaza-7,10-dioxa-3,14-dioxohexadecane (Ref. 9005)

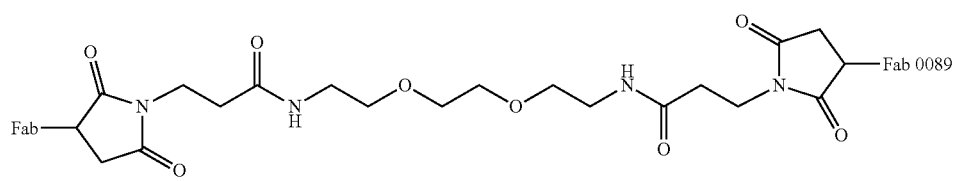

In complete analogy with the example above, a conjugate of Fab 0095 and Fab 0089 was formed. LCMS (m/z: 95928, [M-NH$_3$+H]$^+$). This conjugate was designated 9005.

Example 14

Preparation of BIS(bromoacetyl)ethylene diamine

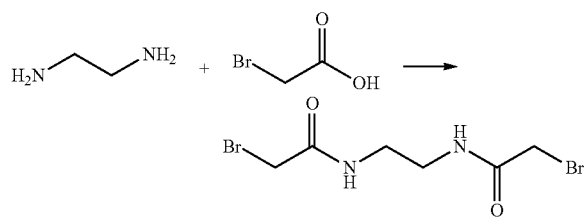

Bromoacetic acid (2.1 g, 15 mmol) was dissolved in DCM (40 ml). The solution was added dropwise to a suspension of immobilised carbodiimide on PS resin (N-cyclohexylcarbodiimide-N'-methyl polystyrene; Novabiochem, prod#: 8.55029.0025; 2.3 mmol/g; 10 g) over a period of 15 minutes. A solution of diamine (450 mg, 7.5 mmol) in DCM (20 ml) was added dropwise to the stirring solution over a period of 20 minutes. The mixture was stirred for 1 h. The solution was filtered and concentrated in vacuo to dryness. LCMS (m/z: 302.9, [M-FH]$^+$).

Example 15

Conjugation of Fab 0088 and Fab 0089 Using bis(bromoacetyl)ethylene diamine (Ref. 9029)

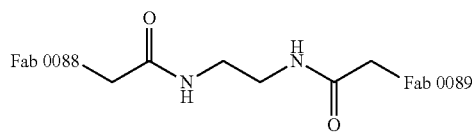

Fab 0088 and Fab 0089 were buffer-exchanged to phosphate buffered saline using an Amicon Ultra centrifugal device (Millipore Corp., 10 kDa MWCO). The concentrations of both proteins were adjusted to 50 micromolar. Bis(p-sulfonatophenyl)phenylphospine dihydrate dipotassium salt from a solution in the phosphate buffer was added to an end-concentration of 200 micromolar. The resulting mixtures were incubated over night at room temperature.

The proteins were buffer exchanged to 20 mM triethanolamin, 1 M NaCl, 200 micromolar Bis(p-sulfonatophenyl)phenylphospine dihydrate dipotassium salt, pH 8.5. Fab 0089 (60 mg, 10 mg/ml) was mixed with bis(bromoacetyl) ethylene diamine (37 mg). The mixture was incubated at ambient temperature for 30 minutes. LCMS (m/z: 47858 [M-NH$_3$+H]$^+$). The sample was diluted (about 10-fold) with 15 mM acetate buffer, pH 4.5. The sample was loaded onto a pre-conditioned HiTrap SP HP column (5 ml). The column was washed with 15 mM acetate buffer. The compound was eluded with an aqueous buffer of 20 mM triethanolamin and 1 M NaCl.pH 8.5. The two protein solutions were mixed, and concentrated/buffer exchanged into 20 mM triethanolamin, 1 M NaCl, pH 8.5, 200 micromolar Bis(p-sulfonatophenyl)phenylphospine dihydrate dipotassium salt, pH 8.5 using an Amicon Ultra centrifugal device (Millipore Corp., 10 kDa MWCO). The mixture was incubated at ambient temperature for 24 hours. The solution was loaded onto a Superdex200 26/60 GL column that had been preconditioned in 15 mM HEPES, 150 mM NaCl, pH 7.3 (HiLoad26/60 Superdex 200 column, GE Heathcare). Using a flow of 2.5 ml/min of in 15 mM HEPES, 150 mM NaCl, pH 7.3 in water, the sample was eluded from the column. The fractions containing the desired conjugate were identified using SDS-PAGE analysis. The pooled fractions were concentrated to a volume of 1000 microliter using an Amicon Ultra Centrifugal device (MWCO 10 kDa). LCMS (m/z: 95834, [M-NH$_3$+H]$^+$).

Example 16

Conjugation of Fab 0094 and Fab 0089 Using bis(bromoacetyl)ethylene diamine (Ref. 9030)

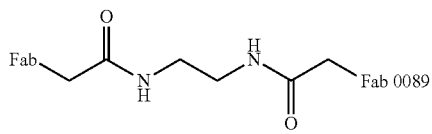

Fab 0094 and Fab 0089 were buffer-exchanged to phosphate buffered saline using an Amicon Ultra centrifugal device (Millipore Corp., 10 kDa MWCO). The concentrations of both proteins were adjusted to 50 micromolar. Bis(p-sulfonatophenyl)phenylphospine dihydrate dipotassium salt from a solution in the phosphate buffer was added to an end-concentration of 200 micromolar. The resulting mixtures were incubated over night at room temperature. The proteins were buffer exchanged to 20 mM triethanolamin, 1 M NaCl, 200 micromolarBis(p-sulfonatophenyl)phenylphospine dihydrate dipotassium salt, pH 8.5.

Fab 0089 (60 mg, 10 mg/ml) was mixed with bis(bromoacetyl)ethylene diamine (37 mg). The mixture was incubated at ambient temperature for 30 minutes. LCMS (m/z: 47858 [M-NH$_3$+H]$^+$).

The sample was diluted (about 10-fold) with 15 mM acetate buffer, pH 4.5. The sample was loaded onto a pre-conditioned HiTrap SP HP column (5 ml). The column was washed with 15 mM acetate buffer. The compound was eluded with an aqueous buffer of 20 mM triethanolamin and 1 M NaCl.pH 8.5.

The two protein solutions were mixed, and concentrated/buffer exchanged into 20 mM triethanolamin, 1 M NaCl, pH 8.5, 200 micromolar Bis(p-sulfonatophenyl)phenylphospine dihydrate dipotassium salt, and 200 micromolar sodium iodide, pH 8.5 using an Amicon Ultra centrifugal device (Millipore Corp., 10 kDa MWCO). The mixture was incubated at ambient temperature for 24 hours. The solution was loaded onto a Superdex200 26/60 GL column that had been preconditioned in 15 mM HEPES, 150 mM NaCl, pH 7.3 (HiLoad26/60 Superdex 200 column, GE Heathcare). Using a flow of 2.5 ml/min of in 15 mM HEPES, 150 mM NaCl, pH 7.3 in water, the sample was eluded from the column. The fractions containing the desired conjugate were identified using SDS-PAGE analysis. The pooled fractions were concentrated to a volume of 1000 microliter using an Amicon Ultra Centrifugal device (MWCO 10 kDa). LCMS (m/z: 95664, [M-NH$_3$+H]$^+$). This compound was designated 9030.

Example 17

Conjugation of Fab 0313 and Fab 0089 Using bis(bromoacetyl)ethylene diamine (Ref. 9031)

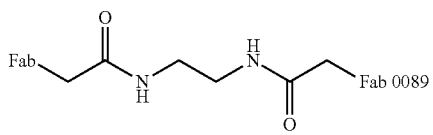

Fab 0094 and Fab 0089 were buffer-exchanged to phosphate buffered saline using an Amicon Ultra centrifugal device (Millipore Corp., 10 kDa MWCO). The concentrations of both proteins were adjusted to 50 micromolar. Bis(p-sulfonatophenyl)phenylphospine dihydrate dipotassium salt from a solution in the phosphate buffer was added to an end-concentration of 200 micromolar. The resulting mixtures were incubated over night at room temperature.

The proteins were buffer exchanged to 20 mM triethanolamin, 1 M NaCl, 200 micromolarBis(p-sulfonatophenyl)phenylphospine dihydrate dipotassium salt, pH 8.5.

Fab 0089 (60 mg, 10 mg/ml) was mixed with bis(bromoacetyl)ethylene diamine (37 mg). The mixture was incubated at ambient temperature for 30 minutes. LCMS (m/z: 47858 $[M-NH_3+H]^+$).

The sample was diluted (about 10-fold) with 15 mM acetate buffer, pH 4.5. The sample was loaded onto a pre-conditioned HiTrap SP HP column (5 ml). The column was washed with 15 mM acetate buffer. The compound was eluded with an aqueous buffer of 20 mM triethanolamin and 1 M NaCl, pH 8.5.

The two protein solutions were mixed, and concentrated/buffer exchanged into 20 mM triethanolamin, 1 M NaCl, pH 8.5, 200 micromolar Bis(p-sulfonatophenyl)phenylphospine dihydrate dipotassium salt, and 200 micromolar sodium iodide, pH 8.5 using an Amicon Ultra centrifugal device (Millipore Corp., 10 kDa MWCO). The mixture was incubated at ambient temperature for 24 hours. The solution was loaded onto a Superdex200 26/60 GL column that had been preconditioned in 15 mM HEPES, 150 mM NaCl, pH 7.3 (HiLoad26/60 Superdex 200 column, GE Heathcare). Using a flow of 2.5 ml/min of in 15 mM HEPES, 150 mM NaCl, pH 7.3 in water, the sample was eluded from the column. The fractions containing the desired conjugate were identified using SDS-PAGE analysis. The pooled fractions were concentrated to a volume of 1000 microliter using an Amicon Ultra Centrifugal device (MWCO 10 kDa). LCMS (m/z: 95638, $[M-NH_3+H]^+$).

Example 18

Thrombin Generation Assay

The effect of antibodies on thrombin generation was studied in normal human plasma (NHP, HemosIL Calibration plasma) supplemented with 10 μM PS/PC: Phosphatidylserine/phosphatidylcholine 25/75%. Coagulation was initiated by re-calcification and addition of Innovin® (1.0 μM). Haemophilia A-like plasma was obtained by the addition of 100 μg/ml sheep anti human FVIII antibody (commercially available).

Thrombin activity was assessed continuously following the conversion of the fluorogenic substrate Z-Gly-Gly-Arg-AMC.HCl (I-1140), from Bachem (Bubendorf, Switzerland). Fluorescence was measured in a microtiter plate Fluorskan Ascent fluorometer (Thermo Labsystems, Helsinki, Finland) with excitation and emission wavelengths set at 368 and 460 nm, respectively. A calibrator was used to allow calculation of the amount of thrombin formed and correction of the obtained relative fluorescence units for inner-filter effects and fluorogenic substrate consumption. In addition, the contribution to substrate conversion by thrombin-α2-macroglobulin complexes was subtracted. These corrections were performed automatically by means of the calibrated automated thrombogram (CAT) computer software provided by Synapse BV (Maastricht, the Netherlands). The first derivative of the data was taken that yielded the thrombin generation curve, allowing calculation of i) lag time, ii) total area under the curve, the endogenous thrombin potential (ETP), iii) thrombin peak height (Peak), iv) time to peak (ttPeak) and v) maximal rate of thrombin generation (Rate).

Example 19

Binding Interaction Analysis

Binding interaction analysis was obtained by Surface Plasmon Resonance in a Biacore T200 instrument. Human Fab Binder (Human Fab Capture Kit, GE Healthcare) was immobilized to a series S CM4 sensor chip (GE Healthcare) in flow-cells 1-4 at 10000 response units (RU) using the amine coupling protocol available within the Biacore T-200 control software (GE Healthcare) and the reagents provided with the Amine Coupling Kit (GE Healthcare). The relevant Fab fragment or Fab-Fab conjugate was captured in flow-cell 2, 3 or 4 at a fixed concentration. Different concentrations of TFPI were tested by diluting TFPI in the running buffer (10 mM Hepes, pH 7.4, 300 mM NaCl, 5 mM $CaCl_2$, 0.05% Surfactant P20, 1 mg/ml BSA). Each sample was assayed using 300 seconds of contact time followed by 600 seconds of dissociation time at 50 μl/min flow rate. A buffer blank was also assayed. The sensor surface was regenerated with 10 mM Glycine pH 2.1 with two cycles each of 30 seconds at 50 μl/min flow rate.

Biacore T200 Evaluation software was used to analyse the data. Determination of binding constants ($k_{on}$, $k_{off}$, $K_D$) was obtained assuming a 1:1 interaction of TFPI and the Fab variant or Fab-Fab conjugate of interest.

Example 20

Effect of Anti-TFPI Antibodies on Tissue Factor-induced Thrombin Generation in Human Haemophilia A Plasma A synergistic effect of anti-TFPI antibodies on tissue factor-induced thrombin generation in human haemophilia A plasma can be obtained by combination or fusion of an antibody targeting an epitope in the KPI-3 region with an antibody targeting an epitope in the KPI-1/KPI-2 region of TFPI.

The effect of antibodies on thrombin generation was studied in a thrombin generation assay according to Example 18.

FIG. 1 (Curve a) shows the thrombin generation curve with NHP. Addition of 100 μg/ml sheep anti human FVIII antibody to NHP to simulate haemophilia A-like condition (Curve b) strongly reduced thrombin generation. NHP contains about 1.6 nM TFPI of which only about 0.2 nM is present as full length TFPIα. Addition of a number of anti-TFPI antibodies, including mAb 2021 (also disclosed in WO2010/072691), to FVIII-neutralised plasma efficiently re-establishes a close to normal thrombin generation curve. However, pre-clinical and clinical studies have shown that in vivo targeting of TFPI with antibodies or aptamers causes a significant elevation of the TFPI plasma level. It was therefore of interest to study the effect of TFPI targeting under conditions with an elevated TFPI concentration. FIG. 1 shows that addition of 20 nM full-length TFPIα to FVIII-neutralised plasma completely prevented a measurable thrombin generation (Curve c) and that addition of 200 nM of a high affinity antibody against KPI-2 (mAb 2021) could not efficiently abrogate TFPI inhibition and establish a robust thrombin generation under these conditions (Curve d). Addition of 200 nM of a high affinity antibody against KPI-3 (mAb 4F110) is completely incapable of establishing a significant thrombin generation in the presence of 20 nM TFPI (Curve e). Surprisingly, however, the combination of 100 nM mAb 2021 and 100 nM mAb 4F110 shows a synergistic effect by establishing a robust thrombin generation (Curve f) that is clearly larger than the sum of thrombin generation produced by each antibody alone and is of the same order of magnitude as the thrombin generation produced in NHP (Curve a).

The data in FIG. 1 shows that a combination of an antibody against KPI-3 of TFPI in combination with an antibody against KPI-2 acted synergistically in reversing TFPI inhibition at elevated TFPI concentrations. Parameters of thrombin peak height (Peak) derived from the curves in FIG. 1 are listed in Table 1.

TABLE 1

Effect of combinations of anti-TFPI KPI-2 and anti-TFPI KPI-3 monospecific antibodies on thrombin generation in FVIII-neutralised NHP (HAP) with 20 nM full-length TFPIα

| | mAb-1 100 nM | mAb-2 100 nM | Combination of mAb1 and mAb-2 | Peak (nM) |
|---|---|---|---|---|
| NHP[1] | — | — | — | 36.0 |
| HAP[2] | — | — | — | 8.0 |
| HAP + TFPI[3] | — | — | — | 0 |
| HAP + TFPI[3] | 2021 | 2021 | 2 × KPI-2 | 18.9 |
| HAP + TFPI[3] | 2021 | 4F110 | KPI-2 + KPI-3 | 62.4 |
| HAP + TFPI[3] | 4F110 | 4F110 | 2 × KPI-3 | 0 |

[1]NHP: Normal human plasma without further additions,
[2]HAP: FVIII-neutralised plasma,
[3]HAP + TFPI: FVIII-neutralised plasma with 20 nM TFPIα

A number of antibodies against the C-terminal region of TFPI were subsequently evaluated for a possible synergistic effect on thrombin generation, when combined with mAb 2021. Under conditions with an elevated TFPI concentration obtained by addition of 20 nM human TFPIα to FVIII-neutralized plasma, none of the C-terminal antibodies were by themselves capable of preventing inhibition by TFPI and promoting a measurable thrombin generation (data not shown). However, the data in Table 2 shows that a number of anti-TFPI KPI-3/C-terminal antibodies (marked *) act synergistically together with mAb 2021 to produce a prominent thrombin peak in plasma under haemophilia A-like conditions with elevated TFPI concentrations. Thrombin peak height derived from thrombin generation curves are listed in Table 2.

TABLE 2

Effect of combinations of anti-TFPI KPI-2 and anti-TFPI KPI-3 monospecific TFPI antibodies on thrombin generation in FVIII-neutralised NHP (HAP) with 20 nM full-length TFPIα

| | mAb-1 100 nM | mAb-2 100 nM | Combination of Ab targets | Peak (nM) |
|---|---|---|---|---|
| NHP[1] | — | — | — | 87.1 |
| HAP[2] | — | — | — | 10.8 |
| HAP + TFPI[3] | — | — | — | 0 |
| HAP + TFPI[3] | 2021 | 2021 | 2 × KPI-2 | 17.2 |
| HAP + TFPI[3] | 2021 | 4F110* | KPI-2 + KPI-3 | 50.4 |
| HAP + TFPI[3] | 2021 | 22F66 | KPI-2 + KPI-3 | 14.7 |
| HAP + TFPI[3] | 2021 | 22F71* | KPI-2 + KPI-3 | 26.4 |
| HAP + TFPI[3] | 2021 | 22F74* | KPI-2 + KPI-3 | 50.1 |
| HAP + TFPI[3] | 2021 | 22F79* | KPI-2 + KPI-3 | 55.6 |
| HAP + TFPI[3] | 2021 | 22F132* | KPI-2 + KPI-3 | 64.8 |
| HAP + TFPI[3] | 2021 | 35F2* | KPI-2 + KPI-3 | 21.8 |
| HAP + TFPI[3] | 2021 | 37F7* | KPI-2 + KPI-3 | 30.6 |
| HAP + TFPI[3] | 2021 | 41F15 | KPI-2 + KPI-3 | 16.4 |
| HAP + TFPI[3] | 2021 | 41F30* | KPI-2 + KPI-3 | 27.5 |
| HAP + TFPI[3] | 2021 | 41F41* | KPI-2 + KPI-3 | 68.3 |
| HAP + TFPI[3] | 2021 | 41F61* | KPI-2 + KPI-3 | 38.9 |
| HAP + TFPI[3] | 2021 | 41F62 | KPI-2 + KPI-3 | 16.6 |
| HAP + TFPI[3] | 2021 | 41F66* | KPI-2 + KPI-3 | 28.7 |
| HAP + TFPI[3] | 2021 | 41F74 | KPI-2 + KPI-3 | 17.2 |

[1]NHP: Normal human plasma without further additions,
[2]HAP: FVIII-neutralised plasma,
[3]HAP + TFPI: FVIII-neutralised plasma with 20 nM TFPIα,
*Synergic effect when combined with mAb 2021

A number of antibodies against the KPI-1 domain of TFPI were evaluated for a possible synergistic effect on thrombin generation when combined with the KPI-3 domain specific mAb 4F110. Table 3 and Table 4 show data on the effect of KPI-1 domain specific mAbs 4903 (American Diagnostica, cat no. ADG4903), 1F91, 2F3, 2F22, 2F35, and 2F45 on lag time, time to peak and peak, alone and in combination with mAb 4F110 in FVIII-neutralized plasma (HAP) with 20 nM of human TFPIα added.

Only some of the KPI-1 specific antibodies were by themselves capable of preventing inhibition by TFPI and promoting a measurable thrombin generation. However, the data in Table 4 show that a number of KPI-1 domain specific antibodies (marked *) act synergistically together with mAb 4F110 to produce a prominent thrombin peak in plasma under haemophilia A-like conditions with elevated TFPI concentrations. Thrombin peak height was derived from thrombin generation curves.

TABLE 3

Effect of combinations of anti-TFPI KPI-1 and anti-TFPI KPI-3 monospecific TFPI antibodies on thrombin generation in FVIII-neutralised NHP (HAP) with 20 nM full-length TFPIα

| | mAb-1 100 nM | mAb-2 100 nM | Combination of Ab | Peak (nM) |
|---|---|---|---|---|
| NHP[1] | — | — | — | 36.0 |
| HAP[2] | — | — | — | 8.0 |
| HAP + TFPI | — | — | — | 0 |
| HAP + TFPI | 4903 | 4903 | 2 × KPI-1 | 0 |
| HAP + TFPI | 4903 | 4F110 | KPI-1 + KPI-3 | 26.9 |

[1]NHP: Normal human plasma without further additions,
[2]HAP: FVIII-neutralised plasma

TABLE 4

Effect of combinations of anti-TFPI KPI-1 and anti-TFPI KPI-3 monospecific antibodies on thrombin generation in FVIII-neutralised NHP (HAP) with 20 nM full-length TFPIα

| | mAb-1 100 nM | mAb-2 100 nM | Combination of Ab targets | Lag time (min) | ttPeak (min) | Peak (nM) |
|---|---|---|---|---|---|---|
| NHP[1] | — | — | — | 6.7 | 11.6 | 71.0 |
| HAP + TFPI[2] | — | — | — | 0 | 0 | 0 |
| HAP + TFPI[2] | 4F110 | 4F110 | 2 × KPI-3 | 0 | 0 | 0 |
| HAP + TFPI[2] | 1F91 | 1F91 | 2 × KPI-1 | 0 | 0 | 0 |
| HAP + TFPI[2] | 1F91* | 4F110 | KPI-1 + KPI-3 | 3.1 | 7.4 | 18.9 |
| HAP + TFPI[2] | 2F3 | 2F3 | 2 × KPI-1 | 5.8 | 14.6 | 20.9 |
| HAP + TFPI[2] | 2F3* | 4F110 | KPI-1 + KPI-3 | 3.3 | 8.9 | 63.3 |
| HAP + TFPI[2] | 2F22 | 2F22 | 2 × KPI-1 | 5.1 | 13.6 | 23.7 |
| HAP + TFPI[2] | 2F22* | 4F110 | KPI-1 + KPI-3 | 3.3 | 9.1 | 61.7 |
| HAP + TFPI[2] | 2F35 | 2F35 | 2 × KPI-1 | 0 | 0 | 0 |
| HAP + TFPI[2] | 2F35 | 4F110 | KPI-1 + KPI-3 | 0 | 0 | 0 |
| HAP + TFPI[2] | 2F45 | 2F45 | 2 × KPI-1 | 9 | 23.6 | 7.2 |
| HAP + TFPI[2] | 2F45* | 4F110 | KPI-1 + KPI-3 | 3.2 | 10.7 | 28.5 |

[1] NHP: Normal human plasma without further additions,
[2] HAP: FVIII-neutralised plasma,
*Synergic effect on thrombin generation when combined with mAb 4F110

Example 21

Synergistic Effect of Anti-TFPI Fab Fragment Conjugates on Tissue Factor-induced Thrombin Generation in Human Haemophilia A Plasma Fab fragments and Fab-Fab conjugates prepared according to Examples 6, 7 10, 12, 13 and 17 were analysed in a binding interaction analysis assay according to Example 19 to determine binding affinity towards human TFPI.
Table 5 shows the equilibrium dissociation constants ($K_D$) for five Fab fragments:
Fab 0088 (KPI-2) SEQ ID NO: 3+4,
Fab 0094 (KPI-2) SEQ ID NO: 5+6
Fab 0095 (KPI-2) SEQ ID NO: 7+8
Fab 0313 (KPI-2) SEQ ID NO: 58+59
Fab 0089 (KPI-3) SEQ ID NO: 9+10
and four KPI-2/KPI-3 domain specific Fab-Fab conjugates (SEQ ID NOs for the individual Fabs are the same as above):
Fab 0088-Fab 0089 (also referred to as 9002; KPI-2/KPI-3)
Fab 0094-Fab 0089 (also referred to as 9004; KPI-2/KPI-3)
Fab 0095-Fab 0089 (also referred to as 9005; KPI-2/KPI-3)
Fab 0313-Fab 0089 (also referred to as 9031; KPI-2/KPI-3)

TABLE 5

Binding of anti-TFPI KPI-2 and anti-TFPI KPI-3 Fab fragments and Fab-Fab conjugates to human TFPIα (TFPIα)

| Ligand | Target | $k_a$ (1/Ms) | $k_d$ (1/s) | Affinity $K_D$ (M) |
|---|---|---|---|---|
| Fab 0088) | TFPIα | 1.7E+06 | 1.0E−04 | 6.0E−11 |
| Fab 0089 | TFPIα | 5.0E+06 | 5.7E−04 | 1.1E−10 |
| Fab 0094 | TFPIα | 1.5E+05 | 6.6E−04 | 4.4E−09 |
| Fab 0095 | TFPIα | 3.9E+06 | 3.0E−03 | 7.8E−10 |
| Fab 0313 | TFPIα | 4.9E+04 | 2.1E−03 | 4.2E−08 |
| Fab 0088-Fab 0089 (9002) | TFPIα | 7.1E+06 | 3.8E−05 | 5.3E−12 |
| Fab 0094-Fab 0089 (9004) | TFPIα | 6.2E+06 | 2.2E−04 | 3.6E−11 |
| Fab 0095-Fab 0089 (9005) | TFPIα | 6.1E+06 | 2.3E−04 | 3.8E−11 |
| Fab 0313-FAb 0089 (9031) | TFPIα | 4.0E+07 | 6.7E−03 | 1.7E−10 |

Fab fragments against the KPI-2 domain of TFPI were evaluated for a possible effect on thrombin generation (as measured according to Example 18). Table 6 shows data on the effect of KPI-2 domain specific Fab fragments 0088, 0094 and 0095 and mAb 2021 on thrombin peak in FVIII-neutralized NHP (HAP) with endogenous TFPI levels. Fab fragments 0088, 0094 and 0095 are variants of mAb 2021. Table 7 shows the results from a similar experiment wherein 2 nM full-length TFPIα was added to FVIII-neutralized NHP (HAP). Thrombin peak height was derived from thrombin generation curves.

TABLE 6

Effect of anti-TFPI KPI-2 specific Fab fragments or mAb 2021 on thrombin generation in FVIII-neutralised NHP (HAP) with endogenous TFPI levels

| | mAb 2021 | Fab 0088 | Fab 0094 | Fab 0095 |
|---|---|---|---|---|
| Fab/mAb conc. (nM) | Thrombin peak (nM) | | | |
| 0.00 | 22.4 | 22.4 | 22.3 | 25.1 |
| 6.25 | 112.8 | 96.8 | 35.9 | 74.2 |
| 12.5 | 113.6 | 98.1 | 45.0 | 81.3 |
| 25.0 | 116.5 | 101.5 | 60.2 | 84.9 |
| 50.0 | 118.2 | 100.9 | 73.9 | 85.4 |
| 100 | 118.0 | 87.7 | 74.1 | 84.7 |

TABLE 7

Effect of anti-TFPI KPI-2 specific Fab fragments or mAb 2021 on thrombin generation in FVIII-neutralised NHP (HAP) with 2 nM full-length TFPIα

| | mAb 2021 | Fab 0088 | Fab 0094 | Fab 0095 |
|---|---|---|---|---|
| Fab/mAb conc. (nM) | Thrombin peak (nM) | | | |
| 0.00 | 4.08 | 4.05 | 4.1 | 3.9 |
| 6.25 | 48.9 | 38.4 | 5.9 | 13.3 |
| 12.5 | 61.7 | 64.2 | 10.6 | 19.4 |
| 25.0 | 68.4 | 69.8 | 14.3 | 22.4 |
| 50.0 | 73.4 | 67.7 | 18.9 | 25.1 |
| 100 | 58.6 | 48.1 | 20.3 | 24.6 |

Fab-Fab conjugates targeting the KPI-2 and KPI-3 domains were prepared according to examples 6, 7 10 (9002) and 12 (9004) and compared to corresponding non-conjugated Fab fragments in order to determine a possible effect on thrombin generation as measured according to Example 18. Tables 8A and 8B show data on the effect of KPI-2+KPI-3 domain specific Fab 0088-Fab 0089 (designated 9002) and Fab 0094-Fab 0089 (designated 9004) conjugates as well as the Fab fragments in a non-conjugated form on thrombin generation in FVIII-neutralized NHP (HAP) with 20 nM full length TFPIα.

It clearly follows that the Fab-Fab conjugates, in addition to the synergistic effect obtained by combining to antibodies or Fab fragments, show an avidity effect on thrombin generation when compared to a combination—i.e. non-conjugated—Fab fragments at the same concentration. Thrombin peak height was derived from thrombin generation curves.

TABLE 8A

Effect of anti-TFPI KPI-2 and anti-TFPI KPI-3 specific Fab fragments or Fab-Fab conjugates on thrombin generation in FVIII-neutralised NHP (HAP) with 20 nM TFPIα

|  | Fab 0088-Fab 0089 (9002) | Fab 0088 + Fab 0089 | Fab 0094-Fab 0089 (9004) | Fab 0094 + Fab 0089 |
|---|---|---|---|---|
|  | Thrombin peak (nM) | | | |
| NHP | 47.2 | 47.2 | 47.2 | 47.2 |
| HA Plasma | 10.3 | 10.3 | 10.3 | 10.3 |
| HA Plasma + 20 nM TFPI | 0 | 0 | 0 | 0 |
| +20 nM Fab-Fab or Fab + Fab* | 22.3 | 0 | 2.0 | 0 |
| +50 nM Fab-Fab or Fab + Fab** | 39.7 | 18.1 | 14.8 | 1.3 |
| +100 nM Fab-Fab or Fab + Fab*** | 46.8 | 36.3 | 19.3 | 5.1 |
| +200 nM Fab-Fab or Fab + Fab***** | 48.2 | 47.4 | 24.9 | 14.1 |

2 × 20*, 2 × 50, 2 × 100* or 2 × 200**** nM of each of the non-conjugated Fab fragments was used to achieve a total concentration comparable to the concentration of the Fab-Fab conjugates

TABLE 8B

Effect of anti-TFPI KPI-2 and anti-TFPI KPI-3 specific Fab fragments or Fab-Fab conjugates on thrombin generation (time to peak) in FVIII-neutralised NHP (HAP) with 20 nM TFPIα

|  | Fab 0088-Fab 0089 (Fab-Fab 9002) | Fab 0088 + Fab 0089 | Fab 0094-Fab 0089 (Fab-Fab 9004) | Fab 0094 + Fab 0089 |
|---|---|---|---|---|
|  | Time to peak (min) | | | |
| NHP | 9.7 | 9.7 | 9.7 | 9.7 |
| HA Plasma | 12.7 | 12.7 | 12.7 | 12.7 |
| HA Plasma + 20 nM TFPI | — | — | — | — |
| +20 nM Fab-Fab or Fab + Fab* | 20.4 | — | ~40 | — |
| +50 nM Fab-Fab or Fab + Fab** | 18.1 | 23.7 | 25 | ~60 |
| +100 nM Fab-Fab or Fab + Fab*** | 17.5 | 20.7 | 17.5 | ~45 |
| +200 nM Fab-Fab or Fab + Fab***** | 16.4 | 18.7 | 16.0 | 23.1 |

2 × 20*, 2 × 50, 2 × 100* or 2 × 200**** nM of each of the non-conjugates Fab fragments was used to achieve a total concentration comparable to the concentration of the Fab-Fab conjugates It clearly follows that the Fab-Fab conjugates show an avidity effect on binding to TFPI, resulting in a synergistic increase in thrombin generation which is higher than the effect obtained by combining two antibodies or two non-conjugated Fab fragments.

Fab fragments and Fab-Fab conjugates targeting the KPI-1 and KPI-3 domains were prepared according to Example 6, 7 and 11 (9028) and were analysed in a binding interaction analysis assay according to Example 19 to determine binding affinity towards human TFPI. Table 9 shows the equilibrium dissociation constants ($K_D$) for one Fab fragment:

Fab 2F22 (KPI-1) (SEQ ID NO: 40 and 41)

and one KPI-1/KPI-3 domain specific Fab-Fab conjugate (SEQ ID NOs for the individual Fabs are the same as above):

Fab 2F22-Fab 0089 (also referred to as 9028; KPI-1/KPI-3)

TABLE 9

Binding of anti-TFPI KPI-1 Fab fragment 2F22 and of an anti-TFPI KPI-1 and anti-TFPI KPI-3 Fab-Fab conjugate to human TFPIα (TFPIα).

| Ligand | Target | $k_a$ (1/Ms) | $k_d$ (1/s) | Affinity $K_D$ (M) |
|---|---|---|---|---|
| Fab 2F22 | TFPIα | 1.2E+05 | 2.1E−04 | 1.7E−09 |
| Fab 2F22-Fab 0089 (9028) | TFPIα | 2.7E+06 | 2.0E−04 | 7.5E−11 |

Fab-Fab conjugates targeting the KPI-1 and KPI-3 domains were compared to corresponding non-conjugated Fab fragments in order to determine a possible effect on thrombin generation measured according to example 18. Table 10 shows data on the effect of KPI-1/KPI-3 domain specific Fab 2F22-Fab 0089 conjugates as well as the Fab fragments in non-conjugates form on thrombin generation in FVIII-neutralized NHP (HAP) with 20 nM full length TFPIα.

TABLE 10

Effect of anti-TFPI KPI-1 and anti-TFPI KPI-3 specific Fab fragments and Fab-Fab conjugate compounds on thrombin generation in FVIII neutralised NHP (HAP) with 20 nM full-length TFPIα

| FVIII neutralized NHP (HAP) | | Peak (nM) | | | | Lag time (min) | | | | ttPeak (min) | | | |
|---|---|---|---|---|---|---|---|---|---|---|---|---|---|
| TFPI conc. (nM) | Drug conc. (nM) | Fab 2F22 | Fab 0089 | Fab 2F22 + Fab 0089 | Fab 2F22 − Fab 0089 conjugate | Fab 2F22 | Fab 0089 | Fab 2F22 + Fab 0089 | Fab 2F22 − Fab 0089 conjugate | Fab 2F22 | Fab 0089 | Fab 2F22 + Fab 0089 | Fab 2F22 − Fab 0089 conjugate |
| 20 | 200 | 26.6 | 0.97 | 68.5 | 87.0 | 7.7 | 16.8 | 4.0 | 4.0 | 14.7 | 76.7 | 11.7 | 10.8 |
| 20 | 100 | 26.7 | 0.8 | 61.7 | 76.4 | 8.0 | 20.3 | 4.0 | 4.2 | 16.3 | 71.8 | 12.5 | 11.0 |
| 20 | 50 | 21.2 | 0.0 | 54.5 | 54.1 | 8.17 | n.a. | 4.2 | 4.3 | 19.8 | n.a. | 13.0 | 12.0 |

TABLE 10-continued

Effect of anti-TFPI KPI-1 and anti-TFPI KPI-3 specific Fab fragments and Fab-Fab conjugate compounds on thrombin generation in FVIII neutralised NHP (HAP) with 20 nM full-length TFPIα

| 20 | 25 | 11.9 | 0.0 | 31.1 | 21.4 | 12.0 | n.a. | 4.7  | 5.2  | 29.0 | n.a. | 15.8 | 16.2 |
|----|----|------|-----|------|------|------|------|------|------|------|------|------|------|
| 20 | 0  | 0.0  | 0.0 | 0.0  | 0.0  | n.a. | n.a. | n.a. | n.a. | n.a. | n.a. | n.a. | n.a. |

| NHP | Peak (nM) | Lag time (min) | ttPeak (min) |
|---|---|---|---|
| | 61.1 | 8.3 | 13.8 |

'Peak': thrombin peak height;
'ttPeak': time to peak.
n.a.: not available.

Example 22

Crystal Structure of Soluble TFPI KPI-1 in Complex with Fab Fragment of Anti-TFPI mAb 2F22

The 3D structure of soluble human TFPI Kunitz-type protease inhibitor domain 1 (KPI-1), inclusive the N-terminal part preceding the TFPI KPI-1, (TFPI 1-79, numbering according to SEQ ID NO: 1), in complex with a Fab fragment (SEQ ID NOs: SEQ 52 and 53) of the anti-TFPI2F22 monoclonal antibody, was determined to high resolution using X-ray crystallography. The results demonstrate that the antibody is capable of binding the KPI-1 of TFPI, and part of the preceding N-terminal. The resulting human TFPI epitope residues comprise: Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75 (SEQ ID NO: 1).

Materials and Methods

To obtain Fab fragments suitable for crystallography, a pTT-based expression vector for expression of a truncated mAb 2F22 HC was generated. The VH fragment was excised from a mAb 2F22 HC expression vector by restriction enzyme digestion and cloned into a linearized pTT-based toolbox vector containing the sequence for a truncated human IgG4 constant region. The IgG4-based HCs was truncated in the hinge region after the lysine corresponding to position 222 in the sequence for the extended Fab 2F22 HC (Fab for chemical coupling, SEQ ID NO: 40). The cloning reaction was subsequently transformed into E. coli for selection. The sequence of the final construct was verified by DNA sequencing. The Fab fragment of mAb 2F22 fragment was expressed as Fab 0296 (SEQ ID NO: 52 and 53) in EXPI293F cells and purified by standard affinity chromatography using KappaSelect resin as described in example 7.

Soluble human TFPI KPI-1, including the N-terminal part of human TFPI and, additionally, a GSSGSSG tag N-terminally attached (SEQ ID NO: 62) and Fab 0296 (which consists of a light chain corresponding to SEQ ID NO: 53 and a heavy chain fragment corresponding to SEQ ID NO: 52), both in phosphate buffered saline (PBS) buffer (4 tablets in 2 litres of water, GIBCO Cat. No. 18912-014 Invitrogen Corporation), were mixed with a slight molar excess (1.1:1) of the TFPI specie. The complex was then concentrated to about 10.0 mg/ml using an Amicon Ultra-4 centrifugal filter with a 10,000 molecular weight cut-off. Crystals were grown by the sitting drop-technique using a 96 wells TTP IQ plate from TTP Lab Tech no:4150-05800 and 100 μl precipitant solution per well. The precipitant solution contained 20% w/v PEG 3350, 200 mM potassium formate and was mixed with the protein solution in a ratio of 3:1. Total drop size was 200 nl and crystals appeared after a few days. A crystal was prepared for cryo-freezing by transferring 1 μl of a cryo-solution mix containing 75% of the precipitant solution and 25% glycerol to the drop containing the crystal. The soaking was allowed for about 2 minutes. The crystal was then fished, flash frozen in liquid $N_2$ and kept at a temperature of 100 K by a cryogenic $N_2$ gas stream during data collection. Crystallographic data were collected, to 1.65 Å at beam-line BL911-3 at MAX-lab, Lund, Sweden. Space group determination, integration and scaling of the data were made by the XDS software package [Kabsch, W., J. Appl. Crystallogr., (1993), Vol. 26, pages 795-800]. The space group was determined to be C2 and the cell parameters for the synchrotron data were determined to be 89.010, 66.660, 106.110 Å, respectively, and with a βangle of 111.18°. The R-sym to 1.65 Å resolution was 8.4% and completeness 99.5%. Mean of intensity/sigma(intensity) of unique reflections were equal to 2.0 at around 1.8 Å resolution.

Molecular replacement (MR) was used for structure determination using the coordinates of a Fab molecule with accession code 1NGZ [Yin, J. et al, Proc Natl Acad Sci USA. 2003. Feb. 4, (100), Vol. 100 pages 856-861] of the Protein Data Bank (PDB) [Berman, H. M. et al, Nucleic Acids Res., (2000), Vol. 28, pages 235-242]. The Fab molecule was divided into two domains, the variable and the constant domains, which each were used as search models in the MR calculations. The Molrep software [Vagin, A. et al, J. Appl. Crystallogr., (1997), Vol. 30, pages 1022-1025] of the CCP4 package CCP4 [Collaborative Computational Project, N., Acta crystallographica. Section D, Biological crystallography, (1994), Vol. 50, pages 760-763] was used to find the positions of the constant and variable Fab domains. The KPI-1 domain was not found in the MR step, however, the difference electron density map indicated the approximate positions of the KPI-1 domain molecules at this stage. After electron density improvements by the DM software of the CCP4 software package, followed by automated model building and phase improvements using the ARP-wARP software [Langer, G. et al, Nat Protoc, (2008), Vol. 3, pages 1171-1179][Murshudov, G. N. et al, Acta Crystallographica Section D Biological Crystallography, (2011), Vol. 67, pages 355-367] gave an almost complete structure of both the Fab 0296 molecule and of the KPI-1 domain structure, and part of the N-terminal preceding the KPI-1 domain. For the TFPI (SEQ ID NO: 1) residues from 15 to 77 are included in the X-ray model which in addition to the KPI-1 also includes some residues N-terminally of the KPI-1 (residues 26-79). For the Fab 0296 fragment the light chain residues 1 to 212 and the heavy chain residues 1 to 221 are observed. A procedure of computer graphics inspection of the electron density maps, model corrections and building using the Coot software program [Emsley, P. et al, Acta Crystallogr. Sect.

D—Biol. Crystallogr., (2004), Vol. 60, pages 2126-2132] followed by crystallographic refinements, using the software programs Refmac5 [Murshudov, G. N. et al, Acta Crystallographica Section D Biological Crystallography, (2011), Vol. 67, pages 355-367] of the CCP4 software package was entered. The procedure was cycled until no further significant improvements could be made to the model. Final R- and R-free for all data to 1.65 Å resolution were 0.192 and 0.220, respectively.

Results

Calculation of the average areas excluded in pair-wise interactions by the software program Areaimol [Lee, B. et al, J Mol Biol, (1971), Vol. 55, pages 379-400][Saff, E. B. et al, Math Intell, (1997), Vol. 19, pages 5-11] of the CCP4 program suite [Collaborative Computational Project, N., Acta crystallographica. Section D, Biological crystallography, (1994), Vol. 50, pages 760-763] gave for the soluble human TFPI fragment/anti-TFPI Fab 0296 molecular complex of the crystal structure 1195 Å$^2$.

The direct contacts between the TFPI KPI-1, inclusive the N-terminal part of TFPI observed in the crystal structure, (SEQ ID NO:62) and anti-TFPI Fab 0296 (SEQ ID NOs: 52 and 53) were identified by running the Contacts software of the CCP4 program suite [Bailey, S., Acta Crystallogr. Sect. D—Biol. Crystallogr., (1994), Vol. 50, pages 760-763] using a cut-off distance of 4.0 Å between the anti-TFPI Fab 0296 and the TFPI fragment molecules. The results from the soluble TFPI fragment/anti-TFPI Fab 0296 complex crystal structure are shown in Table 11. The resulting TFPI KPI-1, including the TFPI N-terminal, epitope for anti-TFPI2F22 was found to comprise one or more of the following residues of TFPI (SEQ ID NO: 1): Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75. Evaluated from distances, charge-charge interactions, hydrogen bonds, polar and hydrophobic interactions and low solvent accessibility the following residues seems to be particularly important residues of the epitope: Arg 41, Arg 65 and Glu 67.

Thus, the anti-TFPI2F22 TFPI epitope comprises residues preceding the KPI-1, including a short N-terminal α-helix, residues in the loop before β-strands 1 of the KPI-1 and residues in the beginning of α-strand 1. It also includes residues in the end of β-strand 2 and residues in the loop between β-strand 2 and the C-terminal α-helix of KPI-1 and residues within the C-terminal α-helix of KPI-1.

The anti-TFPI2F22 paratope for TFPI KPI-1 includes residues Val 2, Phe 27, Tyr 32, Trp 52, Arg 53, Gly 54, Gly 55, Ser 56, Ile 57, Asp 58, Tyr 59, Ala 61, Met 64, Lys 97, Ser 99, His 100, Asn 102, Tyr 103, Val 104, Gly 105 and Tyr 106 of the heavy (H) chain (SEQ ID NO:52, Table 11), and residues Pro 31, Ala 32, Tyr 49, Ser 50, Asn 53, Tyr 55, Thr 56, Tyr 91, Thr 92, Ser 93 and Tyr 94 of the light (L) chain (SEQ ID NO: 53, Table 11).

Table 11. Interactions

TFPI KPI-1, chain K, (SEQ ID NO: 1) interactions with the heavy chain (chain H) of anti-TFPI Fab 0296 (SEQ ID NO: 52) and light chain (chain L) of anti-TFPI Fab 0296 (SEQ ID NO: 53) for the first crystallographic independent complex. A distance cut-off of 4.0 Å was used. The contacts were identified by the CONTACT computer software program of the CCP4 suite [Collaborative Computational Project, N., Acta crystallographica. Section D, Biological crystallography, (1994), Vol. 50, pages 760-763]. In the last column "***" indicates a strong possibility for a hydrogen bond at this contact (distance <3.3 Å) as calculated by CONTACT, "*" indicates a weak possibility (distance >3.3 Å). Blank indicates that the program considered there to be no possibility of a hydrogen bond. Hydrogen-bonds are specific between a donor and an acceptor, are typically strong, and are easily identifiable.

These results indicate that anti-TFPI Fab 0296 specifically binds to TFPI KPI-1 and part of the preceding N-terminal.

| hTFPI | | | Fab 0296 | | | | |
|---|---|---|---|---|---|---|---|
| Res. Type | Res. # and Chain | Atom name | Res. Type | Res. # and Chain | Atom name | Distance [Å] | Possibly H-bond |
| Leu | 16K | CB | Tyr | 32H | OH | 3.77 | |
| Leu | 16K | CD1 | Phe | 27H | CB | 3.99 | |
| | | | Tyr | 32H | CZ | 3.78 | |
| | | | Tyr | 32H | CE2 | 3.86 | |
| | | | Tyr | 32H | OH | 3.40 | |
| | | | Lys | 97H | CE | 3.77 | |
| Leu | 16K | CD2 | Val | 2H | CG2 | 3.74 | |
| Pro | 17K | CG | Thr | 56L | OG1 | 3.68 | |
| Leu | 19K | CA | Tyr | 49L | OH | 3.80 | |
| Leu | 19K | CB | His | 100H | ND1 | 3.95 | |
| | | | His | 100H | CE1 | 3.46 | |
| | | | His | 100H | NE2 | 3.73 | |
| | | | Tyr | 49L | OH | 3.79 | |
| Leu | 19K | CD1 | Ser | 99H | O | 3.47 | |
| | | | His | 100H | CD2 | 3.85 | |
| | | | His | 100H | NE2 | 3.69 | |
| | | | Tyr | 55L | CE1 | 3.86 | |
| Leu | 19K | C | Tyr | 49L | OH | 3.85 | |
| Lys | 20K | N | Tyr | 49L | CZ | 3.89 | |
| | | | Tyr | 49L | OH | 3.01 | *** |
| Lys | 20K | CA | Tyr | 49L | OH | 3.93 | |
| Lys | 20K | CB | Tyr | 49L | OH | 3.70 | |
| Lys | 20K | CG | Tyr | 49L | OH | 3.51 | |
| Lys | 20K | CD | Tyr | 49L | OH | 3.80 | |
| | | | Asn | 53L | CG | 3.73 | |
| | | | Asn | 53L | OD1 | 3.29 | |
| Lys | 20K | CE | Asn | 53L | OD1 | 3.93 | |
| Lys | 20K | C | His | 100H | CE1 | 3.92 | |
| Lys | 20K | O | His | 100H | ND1 | 3.41 | * |
| | | | His | 100H | CE1 | 2.88 | |
| | | | Tyr | 49L | CE2 | 3.58 | |
| Leu | 21K | CA | Tyr | 106H | OH | 3.73 | |
| Leu | 21K | CB | Tyr | 106H | OH | 3.99 | |
| Leu | 21K | CD2 | Tyr | 103H | CE2 | 3.72 | |
| | | | Tyr | 103H | CD2 | 3.52 | |
| | | | His | 100H | ND1 | 3.89 | |
| | | | Tyr | 106H | OH | 3.87 | |
| Leu | 21K | C | Tyr | 106H | OH | 3.71 | |
| Met | 22K | N | Tyr | 106H | CZ | 3.81 | |
| | | | Tyr | 106H | OH | 2.81 | *** |
| | | | Tyr | 106H | CE2 | 3.87 | |
| Met | 22K | CA | Tyr | 106H | OH | 3.68 | |
| Met | 22K | CB | Tyr | 106H | OH | 3.60 | |
| Met | 22K | CG | Ser | 50L | OG | 3.75 | |
| Met | 22K | SD | Pro | 31L | CG | 3.78 | |
| Met | 22K | CE | Pro | 31L | CG | 3.80 | |
| Met | 22K | O | Tyr | 106H | OH | 3.86 | * |
| Phe | 25K | CZ | Gly | 105H | O | 3.58 | |
| | | | Ala | 32L | CB | 3.89 | |
| Phe | 25K | CE2 | Val | 104H | O | 3.96 | |
| | | | Gly | 105H | CA | 3.87 | |
| | | | Gly | 105H | C | 3.87 | |
| | | | Gly | 105H | O | 3.41 | |
| | | | Tyr | 106H | CE1 | 3.90 | |
| | | | Tyr | 106H | CZ | 3.61 | |
| | | | Tyr | 106H | OH | 3.79 | |
| | | | Tyr | 106H | CE2 | 3.86 | |
| Phe | 25K | CD2 | Val | 104H | O | 3.81 | |
| | | | Tyr | 106H | CZ | 3.81 | |
| | | | Tyr | 106H | OH | 3.59 | |
| Cys | 35K | SG | Ala | 61H | CB | 3.72 | |
| Ala | 37K | CB | Met | 64H | CE | 3.75 | |

-continued

| hTFPI | | | Fab 0296 | | | |
|---|---|---|---|---|---|---|
| Res. Type | Res. # and Chain | Atom name | Res. Type | Res. # and Chain | Atom name | Distance [Å] | Possibly H-bond |
| Met | 39K | SD | Ile | 57H | O | 3.21 | |
| Met | 39K | CE | Ser | 56H | CA | 3.87 | |
| | | | Ser | 56H | CB | 3.66 | |
| | | | Ile | 57H | N | 3.44 | |
| | | | Ile | 57H | O | 3.31 | |
| Arg | 41K | NE | Ser | 56H | CB | 3.74 | |
| Arg | 41K | CZ | Ser | 56H | CB | 3.85 | |
| | | | Asp | 58H | OD1 | 3.00 | |
| Arg | 41K | NH1 | Asp | 58H | CG | 3.53 | |
| | | | Asp | 58H | OD1 | 2.67 | *** |
| | | | Asp | 58H | OD2 | 3.65 | * |
| Arg | 41K | NH2 | Ser | 56H | CB | 3.50 | |
| | | | Ile | 57H | N | 3.79 | * |
| | | | Ile | 57H | C | 3.58 | |
| | | | Ile | 57H | O | 3.12 | *** |
| | | | Asp | 58H | CG | 3.78 | |
| | | | Asp | 58H | OD1 | 2.58 | *** |
| Tyr | 56K | CE2 | Asp | 58H | OD1 | 3.40 | |
| Gly | 57K | O | Met | 64H | CE | 3.82 | |
| Gly | 58K | O | Asp | 58H | C | 3.65 | |
| | | | Tyr | 59H | N | 2.83 | *** |
| | | | Tyr | 59H | CB | 3.96 | |
| | | | Tyr | 59H | CD1 | 3.80 | |
| | | | Asp | 58H | CA | 3.56 | |
| | | | Tyr | 59H | CA | 3.82 | |
| | | | Tyr | 59H | O | 3.69 | * |
| Cys | 59K | CA | Tyr | 59H | O | 3.61 | |
| Cys | 59K | CA | Tyr | 59H | O | 3.59 | |
| Cys | 59K | CB | Tyr | 59H | O | 3.52 | |
| Cys | 59K | CB | Tyr | 59H | O | 3.30 | |
| Cys | 59K | SG | Met | 64H | SD | 3.34 | |
| | | | Ala | 61H | CA | 3.60 | |
| | | | Tyr | 59H | O | 3.92 | |
| | | | Ala | 61H | N | 3.94 | |
| | | | Ala | 61H | CB | 3.75 | |
| Cys | 59K | SG | Ala | 61H | CB | 3.85 | |
| Glu | 60K | N | Ser | 93L | O | 3.90 | * |
| Glu | 60K | CA | Ser | 93L | O | 3.25 | |
| | | | Ser | 93L | CB | 4.00 | |
| | | | Ser | 93L | C | 3.99 | |
| Glu | 60K | OE2 | Tyr | 94H | CE1 | 3.99 | |
| Glu | 60K | C | Ser | 93L | O | 3.30 | |
| Glu | 60K | O | Ser | 93L | O | 3.25 | *** |
| Gly | 61K | O | Ser | 93L | CA | 3.27 | |
| | | | Ser | 93L | CB | 3.51 | |
| Asn | 62K | CA | Thr | 92L | O | 3.84 | |
| Gln | 63K | CA | Val | 104H | CG1 | 3.96 | |
| Gln | 63K | CG | Tyr | 91L | O | 3.58 | |
| | | | Gly | 105H | CA | 3.77 | |
| Gln | 63K | CD | Tyr | 91L | O | 3.77 | |
| | | | Thr | 92L | CA | 3.83 | |
| Gln | 63K | OE1 | Thr | 92L | O | 3.95 | * |
| | | | Thr | 92L | CA | 3.87 | |
| Gln | 63K | NE2 | Tyr | 91L | O | 3.65 | * |
| | | | Thr | 92L | CA | 3.98 | |
| | | | Thr | 92L | CG2 | 3.73 | |
| | | | Ala | 32L | CB | 3.74 | |
| Arg | 65K | NE | Asp | 58H | OD1 | 3.91 | * |
| | | | Asp | 58H | OD2 | 3.76 | * |
| Arg | 65K | CZ | Asp | 58H | OD2 | 3.81 | |
| Arg | 65K | NH2 | Asp | 58H | CG | 3.65 | |
| | | | Asp | 58H | OD2 | 2.92 | *** |
| | | | Val | 104H | CG1 | 3.71 | |
| | | | Val | 104H | CG2 | 3.60 | |
| Arg | 65K | O | Val | 104H | CG2 | 3.64 | |
| Phe | 66K | CD1 | Tyr | 103H | CE1 | 3.80 | |
| | | | Tyr | 103H | CD1 | 3.77 | |
| Phe | 66K | CE1 | Tyr | 103H | CE1 | 3.74 | |
| | | | Tyr | 103H | CD1 | 3.63 | |
| Glu | 67K | CB | Asn | 102H | ND2 | 3.46 | |
| Glu | 67K | CG | Ser | 56H | OG | 3.33 | |
| Glu | 67K | CD | Gly | 54H | N | 3.40 | |
| | | | Gly | 54H | CA | 3.69 | |
| | | | Ser | 56H | OG | 3.32 | |
| | | | Trp | 52H | CB | 3.78 | |
| | | | Asn | 102H | ND2 | 3.94 | |
| | | | Ser | 56H | CB | 3.89 | |
| Glu | 67K | OE1 | Gly | 54H | N | 2.79 | *** |
| | | | Gly | 54H | CA | 3.49 | |
| | | | Trp | 52H | CB | 3.57 | |
| | | | Trp | 52H | C | 3.94 | |
| | | | Arg | 53H | N | 3.47 | * |
| | | | Arg | 53H | CG | 3.98 | |
| | | | Arg | 53H | CD | 3.87 | |
| | | | Arg | 53H | C | 3.84 | |
| | | | Asn | 102H | CG | 3.86 | |
| | | | Asn | 102H | OD1 | 3.93 | * |
| | | | Asn | 102H | ND2 | 2.97 | *** |
| Glu | 67K | OE2 | Gly | 54H | C | 3.27 | |
| | | | Gly | 54H | O | 3.77 | * |
| | | | Gly | 55H | N | 3.51 | * |
| | | | Ser | 56H | N | 3.02 | *** |
| | | | Gly | 54H | N | 3.28 | *** |
| | | | Gly | 54H | CA | 3.27 | |
| | | | Ser | 56H | CA | 3.64 | |
| | | | Ser | 56H | OG | 2.52 | *** |
| | | | Trp | 52H | CB | 3.91 | |
| | | | Ser | 56H | CB | 3.10 | |
| Glu | 71K | CD | Asn | 102H | ND2 | 3.46 | |
| | | | Arg | 53H | NH1 | 3.50 | |
| Glu | 71K | OE1 | Asn | 102H | CB | 3.82 | |
| | | | Asn | 102H | CG | 3.79 | |
| | | | Asn | 102H | ND2 | 2.81 | *** |
| Glu | 71K | OE2 | Arg | 53H | NH2 | 3.78 | * |
| | | | Arg | 53H | CD | 3.65 | |
| | | | Arg | 53H | NE | 3.58 | * |
| | | | Asn | 102H | ND2 | 3.43 | * |
| | | | Arg | 53H | CZ | 3.01 | |
| | | | Arg | 53H | NH1 | 2.28 | *** |
| Glu | 71K | O | Tyr | 103H | CE1 | 3.91 | |
| | | | Tyr | 103H | OH | 3.57 | * |
| Met | 75K | N | Tyr | 103H | OH | 3.80 | * |
| Met | 75K | CB | Tyr | 103H | CE1 | 3.82 | |
| | | | Tyr | 103H | CZ | 4.00 | |
| | | | Tyr | 103H | OH | 3.73 | |

These results show that anti-TFPI Fab 0296 specifically binds to TFPI KPI-1 and part of the preceding N-terminal.

Example 23

Binding of Antibodies to Cell Surface Associated TFPI

The ability of anti-TFPI antibodies, Fab fragments or Fab-Fab conjugates to bind to TFPI associated with the endothelial cell surface in vitro was studied using flow cytometry. Human umbilical vein cell line EA.hy926 cells (ATCC) were incubated for 30 min on ice with different concentrations of anti-TFPI mAb 2021, Fab 0088, Fab 0094, Fab 0095, or Fab 0313, or Fab 0088-Fab 0089 conjugate 9002 or Fab 0094-Fab 0089 conjugate 9004 in assay buffer (PBS supplemented with 2% FCS). The cells were washed with PBS and subsequently incubated on ice with APC-conjugated secondary antibody (Allophycocyanin-AffiniPure F(ab')2 Fragment Donkey Anti-Human IgG (H+L), Jackson ImmunoResearch, Cat. 709-136-149) for 30 min in assay buffer. The cells were washed with PBS and analysed on a BD LSRFortessa flow cytometer. Binding profiles were plotted using the median fluorescence intensity at different antibody concentrations and half maximal binding values (EC50) were calculated.

The data listed in Table 12 clearly shows that KPI-2 TFPI Fab 0088, Fab 0094, and Fab 0313 (all Fab fragments are derived from mAb 2021) bind with similar affinities to EA.hy926 cell surface associated TFPI and TFPIα as determined by SPR analysis listed in Table 5. In contrast to high affinity binding to TFPIα (Table 5), no measurable binding of anti-TFPI KPI-3 mAb 4F110 could be detected to EA.hy926 cell surface associated TFPI. The data also shows that the affinity of Fab 0094-Fab 0089 conjugate 9004 for EA.hy926 cell surface associated TFPI is significantly reduced compared to its affinity for TFPIα (Table 5) indicating preferential binding to TFPI species which comprises a C-terminal region.

TABLE 12

EC50 values for the binding of anti-TFPI antibodies and fragments EA.hy926 cell surface associated TFPI (n.b: No measurable binding)

| Antibody (mAb/Fab/Fab-Fab conjugate) | EC50 (nM) |
|---|---|
| mAb 2021 | 0.11 |
| Fab 0088 | 0.31 |
| Fab 0094 | 3.80 |
| Fab 0313 | 25.90 |
| mAb 4F110 | n.b. |
| Fab 0088-Fab 0089 conjugate (9002) | 0.33 |
| Fab 0094-Fab 0089 conjugate (9004) | 6.90 |

Example 24

Neutralisation by mAbs and Fab-Fab Conjugates of the TFPIβ Inhibition of TF/FVIIa-mediated FXa Generation Human umbilical vein cell line EA.hy926 cells (ATCC) were grown to 100% confluence in 96 well plates in DMEM (Gibco) supplied with 10% FCS and 1% penicillin/streptomycin. The cells were stimulated with 20 ng/ml TNFα and 20 ng/ml IL-1β for 3 hours and used for testing of neutralisation of cell surface TF-dependent FX activation. Cells were washed twice with 25 mM HEPES, 137 mM NaCl, 3.5 mM KCl, pH 7.4 before FX activation was measured in 25 mM HEPES, 137 mM NaCl, 3.5 mM KCl, 5 mM $CaCl_2$, 1 mg/ml BSA pH 7.4. After incubation for 15 min at 37° C., neutralisation of TFPI was induced by addition of 0-60 nM mAb or Fab-Fab conjugate for 120 min. This was followed by incubation with 50 µM rFVIIa (Novo Nordisk A/S) for 15 min. Generation of FXa was then initiated by addition of 50 nM FX for 40 min at 37° C. The reaction was stopped by mixing 40 µl supernatant with 10 µl (75 mM) EDTA and FXa activity was finally measured with 0.6 mM chromogenic substrate S-2765 (Chromogenix). TF/FVIIa activity was verified in control experiments with addition of 0.5 mg/ml neutralising goat anti human TF polyclonal antibody.

Figure 2:
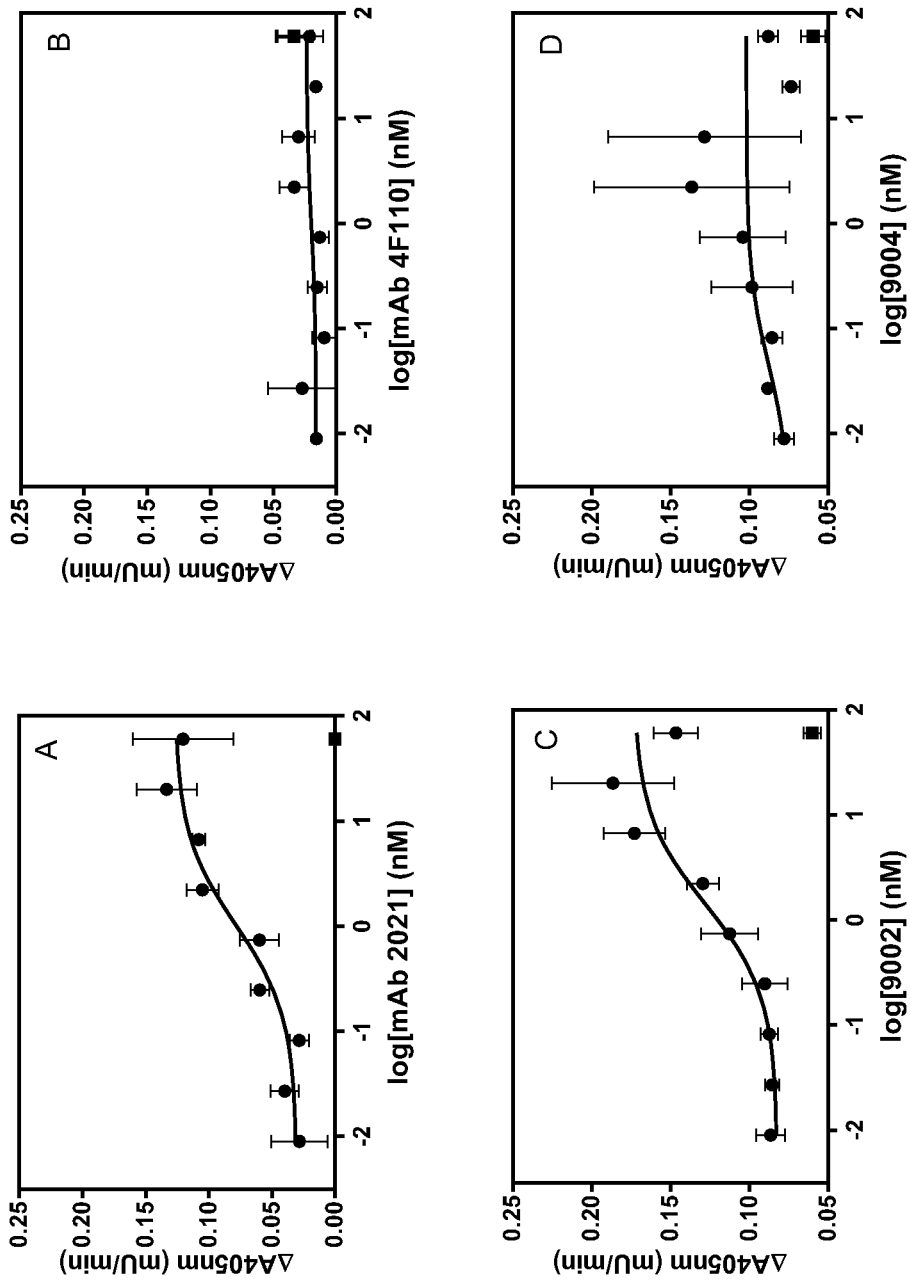
FIG. 2A-D shows the neutralisation by mAbs and Fab-Fab conjugates of the TFPIβ inhibition of TF/FVIIa-mediated FXa generation on the cell surface. EA.hy926 wt cells were incubated with increasing concentrations of mAbs or Fab-Fab conjugates. FXa activity in the supernatant was measured after incubation with 50 pM FVIIa and 50 nM FX at 37° C. with various concentrations (0-60 nM) of mAb 2021 (A), mAb 4F110: (B), Fab-Fab conjugate 9002 (C), or Fab-Fab conjugate 9004 (D). Squares show the effect of 0.5 mg/ml goat anti human TF polyclonal antibody together with 60 nM mAb or Fab-Fab conjugate. Results are shown as mean±SD, (n=3).

Data were analysed with GraphPad Prism Software (version 5). Results are shown in FIG. 2. FXa activity in the supernatant was measured after incubation with 50 µM FVIIa and 50 nM FX at 37° C. with various concentrations (0-60 nM) of mAb 2021: (A); mAb 4F110 (B); Fab 0088-Fab 0089 conjugate 9002 (C); or Fab 0094-Fab 0089 conjugate 9004 (D). Squares show the effect of 0.5 mg/ml goat anti human TF polyclonal antibody together with 60 nM mAb or Fab-Fab conjugate. Results are shown as mean±SD, n=3.

The data show that mAb 2021, but not mAb 4F110, was capable of neutralizing TFPI inhibition of TF/FVIIa-mediated FX activation on the surface of EA.hy926 cells. Neutralization of TFPIβ was also observed with Fab 0088-Fab 0089 conjugate 9002. In contrast, Fab 0094-Fab 0089 9004 was without a significant neutralizing effect on the TFPIβ inhibition of TF/FVIIa on EA.hy926 cells. Modulation of the affinity of a KPI-2 binding antibody is therefore shown to be crucial for the functional effect Fab-Fab conjugates against KPI-2 and KPI-3.

Example 25

Generation of Asymmetric Bispecific Antibodies

A bispecific TFPI KPI-2/KPI-3 binding antibody antibody was generated based on an asymmetric IgG format, i.e through FC heterodimerization. In order to achieve FC heterodimerization a set of compatible mutations were engineered into the FC region of hIgG1 variants of mAb 2021 and mAb 4F110.

The VH fragments were excised from the mAb 2021 and mAb 4F110 HC expressions vectors by restriction enzyme digestion and cloned into a linearized pTT-based toolbox vector containing the sequence for a human IgG1 constant region. The cloning reaction was subsequently transformed into E. coli for selection. The sequence of the final construct was verified by DNA sequencing.

To support FC heterodimerization by controlled Fab-arm exchange a single phenylalanine to leucine mutation was introduced into the CH3 domain of the IgG1 HC of mAb 2021, corresponding to position 409 in SEQ ID NO: 63. The mutations was introduced by site-directed mutagenesis using the QuikChange® Site-Directed mutagenesis kit from Stratagene. The sequences of all final construct were verified by DNA sequencing. The engineered IgG1 version of mAb 2021 was expressed as mAb 0309 (SEQ ID NO: 63 and 64) in EXPI293F cells as described in example 7. Purification was performed by standard affinity chromatography using MabSelectSuRe resin from GE Healthcare according to manufacturer's instructions. The purified antibodies were buffer exchanged to PBS buffer pH7.2.

A matching lysine to arginine mutation was introduced into the CH3 domain of the IgG1 HC of mAb 4F110, corresponding to position 410 in SEQ ID NO: 65. The mutations was introduced by site-directed mutagenesis using the QuikChange® Site-Directed mutagenesis kit from Stratagene. The sequences of all final construct were verified by DNA sequencing. The engineered IgG1 version of mAb 2021 was expressed as mAb 0312 (SEQ ID NO: 65 and 66) in EXPI293F cells as described in example 7. Purification was performed by standard affinity chromatography using MabSelectSuRe resin from GE Healthcare according to manufacturer's instructions. The purified antibodies were buffer exchanged to PBS buffer pH7.2.

A bispecific KPI-2/KPI-3 binding antibody was prepared by controlled Fab-arm exchange between the engineered IgG1 variant of mAb2021 (KPI-2 binding), mAb309 and the engineered IgG1 variant of mAb4F110 (KPI-3 binding), mAb312. The bispecific antibody was prepared essentially according to published methods (Labrijn et al., PNAS, 110: 5145-5150 (2013)).

In short, mAb 0309 (mAb2021 IgG1 Phe-to-Leu variant SEQ ID NO: 63) was mixed with mAb 0312 (mAb 4F110 IgG1 Lys-to-Arg variant SEQ ID NO: 65) at a 1:1 molar ratio (1 mg/ml per antibody) in PBS buffer. The antibodies were selectively reduced by incubation of the 1:1 mixture for 90 minutes at 37° C. in the presence of 25 mM 2-mercaptoethylamine (MEA) to form half antibodies and allow Fab-arm exchange. Finally, spontaneous reassembly and re-oxidation was obtained after removal of the reducing agent (diafiltration in to PBS buffer without MEA) and storage at +5° C. for at least 16 hours. Hetero-dimerization, promoted by the CH3 domain mutations, was observed with an efficiency exceeding 90%. The final bispecific antibody derived from mAb 0309 and 0312 was named mAb 0325 (SEQ ID NO: 67-70).

The reverse set of mutations, i.e Lys-to-Arg on Mab 2021 IgG1 and Phe-to-Leu on Mab 4F110 IgG1 were also generated and tested with similar results.

A synergistic effect on tissue factor-induced thrombin generation in human haemophilia A plasma can be obtained by using an asymmetric bispecific antibody, assembled through FC heterodimerisation of antibodies targeting epitopes in the KPI-2 and KPI-3 regions of TFPI.

The effect of antibodies on thrombin generation was studied in a thrombin generation assay according to Example 18.

Figure 3:
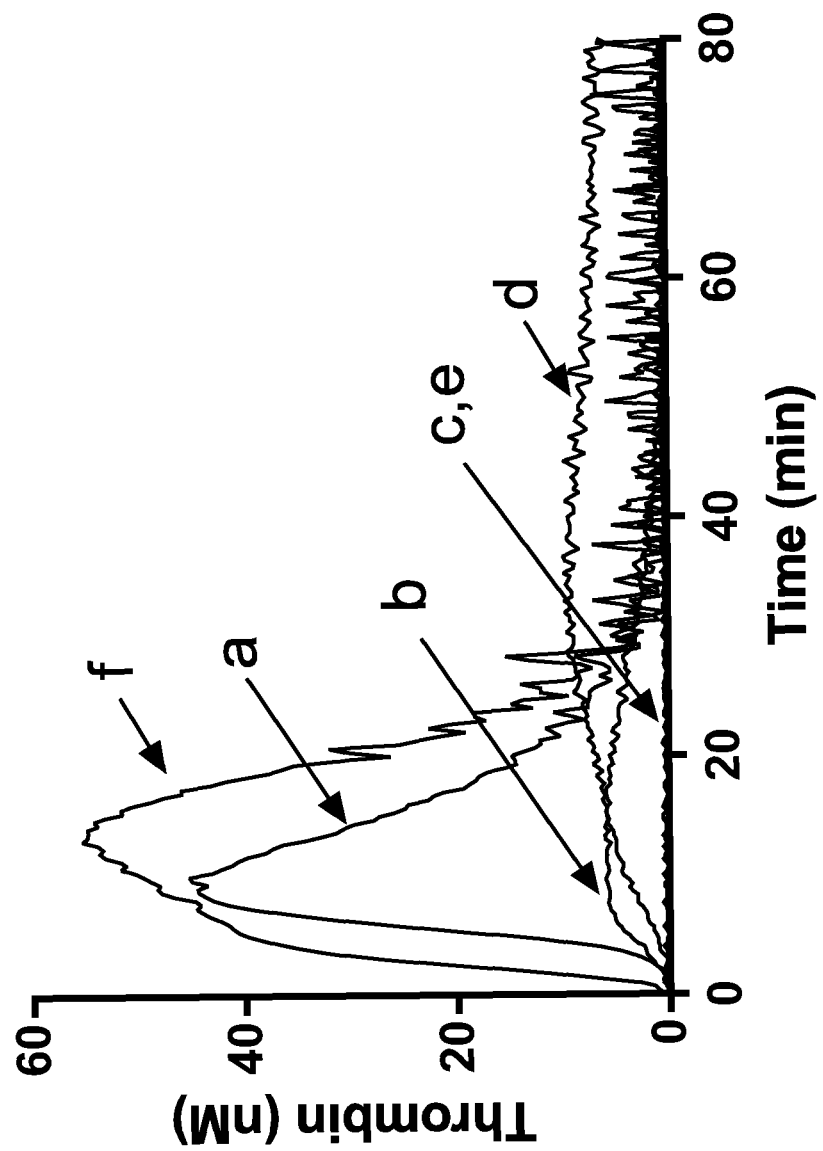
FIG. 3 shows that thrombin generation was strongly enhanced by combined antibody targeting of KPI-2 and KPI-3 of TFPI in human plasma under haemophilia A-like conditions with increased TFPI levels using an asymmetric bispecific antibody format.

FIG. 3 (Curve a) shows the thrombin generation curve with NHP. Addition of 100 µg/ml sheep anti human FVIII antibody to NHP to simulate haemophilia A-like condition (Curve b) strongly reduced thrombin generation. NHP contains about 1.6 nM TFPI of which only about 0.2 nM is present as full length TFPIα. Addition of a number of anti-TFPI antibodies, including mAb 0309 an FC engineered version of mAb 2021 (mAb 2021 also disclosed in WO2010/072691), to FVIII-neutralised plasma efficiently re-establishes a close to normal thrombin generation curve (data not shown). However, pre-clinical and clinical studies have shown that in vivo targeting of TFPI with antibodies or aptamers causes a significant elevation of the TFPI plasma level. It was therefore of interest to study the effect of TFPI targeting under conditions with an elevated TFPI concentration. FIG. 3 shows that addition of 20 nM full-length TFPIα to FVIII-neutralised plasma completely prevented a measurable thrombin generation (Curve c) and that addition of 200 nM of a high affinity antibody against KPI-2 (mAb 0309) could not efficiently abrogate TFPI inhibition and establish a robust thrombin generation under these conditions (Curve d). Addition of 200 nM of a high affinity antibody against KPI-3 (mAb 0312, an FC engineered version of mAb 4F110) is completely incapable of establishing a significant thrombin generation in the presence of 20 nM TFPI (Curve e). In contrast, the asymmetric bispecific antibody combination of mAb 0309 and 0312; mAb 0325 shows a synergistic effect by establishing a robust thrombin generation (Curve f) that is clearly larger than the sum of thrombin generation produced by each antibody alone and is of the same order of magnitude as the thrombin generation produced in NHP (Curve a).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A bispecific antibody that is capable of specifically binding a first epitope of tissue factor pathway inhibitor (TFPI) and a second epitope of tissue factor pathway inhibitor (TFPI), wherein the first epitope comprises an amino acid residue located within positions 1 to 181 of SEQ ID NO: 1 and the second epitope comprises an amino acid residue located within TFPI positions 182 to 276 of SEQ ID NO: 1.

2. The bispecific antibody according to claim 1, wherein a first epitope comprises an amino acid residue within the KPI-1 domain of tissue factor pathway inhibitor (TFPI).

3. The bispecific antibody according to claim 1, wherein a first epitope comprises an amino acid residue within the KPI-2 domain of tissue factor pathway inhibitor (TFPI).

4. The bispecific antibody according to claim 1, wherein a second epitope comprises an amino acid residue within the KPI-3 domain of tissue factor pathway inhibitor (TFPI).

5. The bispecific antibody according to claim 1, wherein said antibody is capable of binding a KPI-1 epitope comprising one or more amino acid residues selected from the group consisting of Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75 of SEQ ID NO: 1.

6. The bispecific antibody according to claim 5, wherein said antibody is capable of binding a KPI-1 epitope comprising amino acid residues Arg 41, Arg 65 and/or Glu 67 of SEQ ID NO: 1.

7. The bispecific antibody according to claim 1, wherein said antibody is capable of binding a KPI-2 epitope comprising one or more amino acid residues selected from the group consisting of Glu 100, Glu 101, Asp 102, Pro 103, Arg 107, Tyr 109, Thr 111, Tyr 113, Phe 114, Asn 116, Gln 118, Gln 121, Cys 122, Glu 123, Arg 124, Phe 125, Lys 126 and Leu 140 of SEQ ID NO: 1.

8. The bispecific antibody according to claim 7 that is capable of specifically binding tissue factor pathway inhibitor (TFPI) wherein said antibody is capable of specifically binding a KPI-2 epitope comprising amino acid residue Arg 107 of SEQ ID NO: 1.

9. The bispecific antibody according to claim 1, wherein said antibody is capable of binding a KPI-3 epitope comprising one or more amino acid residues selected from the group consisting of Tyr 207, Asn 208, Ser 209, Val 210, Ile 211, Gly 211, Lys 213, Arg 215, Lys 232, Gln 233, Leu 236 and Lys 240 of SEQ ID NO: 1.

10. The bispecific antibody according to claim 9 wherein said antibody is capable of binding a KPI-3 epitope comprising amino acid residue Ile 211, Lys 213 and/or Arg 215of SEQ ID NO: 1.

11. The bispecific antibody according to claim 1 which is a Fab-Fab conjugate or in a full length antibody format.

12. The bispecific antibody according to claim 1 which is humanized.

13. The bispecific antibody according to claim 1 which selectively targets TFPIα.

14. A pharmaceutical composition comprising the bispecific antibody according to claim 1.

15. A method for treating coagulopathy in a patient in need of such treatment, said method comprising administering to said patient a therapeutically effective amount of the pharmaceutical composition according to claim 14.

16. The bispecific antibody according to claim 3, wherein a second epitope comprises an amino acid residue within the KPI-3 domain of tissue factor pathway inhibitor (TFPI).

17. The bispecific antibody according to claim 7, wherein said antibody is capable of binding a KPI-3 epitope comprising one or more amino acid residues selected from the group consisting of Tyr 207, Asn 208, Ser 209, Val 210, Ile 211, Gly 212, Lys 213, Arg 215, Lys 232, Gln 233, Leu 236 and Lys 240 of SEQ ID NO: 1.

18. The bispecific antibody according to claim 8, wherein said antibody is capable of binding a KPI-3 epitope comprising one or more amino acid residues selected from the group consisting of Tyr 207, Asn 208, Ser 209, Val 210, Ile 211, Gly 212, Lys 213, Arg 215, Lys 232, Gln 233, Leu 236 and Lys 240 of SEQ ID NO: 1.

19. The bispecific antibody according to claim 7 wherein said antibody is capable of binding a KPI-3 epitope comprising amino acid residue Ile 211, Lys 213 and/or Arg 215 of SEQ ID NO: 1.

20. The bispecific antibody according to claim 8 wherein said antibody is capable of binding a KPI-3 epitope comprising amino acid residue Ile 211, Lys 213 and/or Arg 215 of SEQ ID NO: 1.

* * * * *

SEQUENCE LISTING

```
<160> NUMBER OF SEQ ID NOS: 70

<210> SEQ ID NO 1
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
        50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175
```

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
210             215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
        275

<210> SEQ ID NO 2
<211> LENGTH: 181
<212> TYPE: PRT
<213> ORGANISM: Homo sapiens

<400> SEQUENCE: 2

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
        50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe
            180

<210> SEQ ID NO 3
<211> LENGTH: 227
<212> TYPE: PRT
<213> ORGANISM: Artificial
<220> FEATURE:
<223> OTHER INFORMATION: humanised

<400> SEQUENCE: 3

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys
225

<210> SEQ ID NO 4
<211> LENGTH: 219
<212> TYPE: PRT
<213> ORGANISM: Artificial
<220> FEATURE:
<223> OTHER INFORMATION: humanised

<400> SEQUENCE: 4

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 227
<212> TYPE: PRT
<213> ORGANISM: Artificial
<220> FEATURE:
<223> OTHER INFORMATION: humanised

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys
225

<210> SEQ ID NO 6
<211> LENGTH: 219
<212> TYPE: PRT
<213> ORGANISM: Artificial
<220> FEATURE:
<223> OTHER INFORMATION: humanised

<400> SEQUENCE: 6

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 7
<211> LENGTH: 227
<212> TYPE: PRT
<213> ORGANISM: Artificial
<220> FEATURE:
<223> OTHER INFORMATION: humanised

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Tyr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

-continued

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys
225

<210> SEQ ID NO 8
<211> LENGTH: 219
<212> TYPE: PRT
<213> ORGANISM: Artificial
<220> FEATURE:
<223> OTHER INFORMATION: humanised

<400> SEQUENCE: 8

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Leu Gln Arg Pro Gly Glu Ser
            35                  40                  45

Pro Lys Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 224
<212> TYPE: PRT
<213> ORGANISM: Artificial
<220> FEATURE:
<223> OTHER INFORMATION: chimer

```
<400> SEQUENCE: 9

Gln Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Ile Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Asp Thr Asn Leu Asn Glu Lys Phe
    50                  55                  60

Lys Ser Lys Ala Thr Leu Thr Val Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Thr Arg Trp Asp Arg Phe Asp Gly Phe Val Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

<210> SEQ ID NO 10
<211> LENGTH: 214
<212> TYPE: PRT
<213> ORGANISM: Artificial
<220> FEATURE:
<223> OTHER INFORMATION: chimer

<400> SEQUENCE: 10

Glu Thr Thr Val Thr Gln Ser Pro Ala Ser Leu Ser Met Ala Ile Gly
 1               5                  10                  15

Gly Lys Val Thr Ile Arg Cys Ile Ile Ser Thr Asn Ile Asp Asp Asp
            20                  25                  30

Ile Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asp Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130                135                140
Lys Val Gln Trp Lys Val Asp Asn Ala Leu Gln Ser Gly Asn Ser Gln
145                150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
                180                185                190

Ala Cys Glu Val Thr His Gln Gly Leu Ser Ser Pro Val Thr Lys Ser
                195                200                205

Phe Asn Arg Gly Glu Cys
    210

<210> SEQ ID NO 11
<211> LENGTH: 117
<212> TYPE: PRT
<213> ORGANISM: Artificial
<220> FEATURE:
<223> OTHER INFORMATION: chimer

<400> SEQUENCE: 11

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Pro Met Asn Trp Val Arg Gln Ser His Gly Lys Asn Leu Glu Trp Ile
            35                  40                  45

Gly Leu Ile Asn Pro Tyr Asn Gly Asp Thr Thr Phe Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Thr Tyr Glu Tyr Val Asp Tyr Trp Gly Gln Gly Thr Thr
                100                 105                 110

Leu Thr Val Ser Ser
        115

<210> SEQ ID NO 12
<211> LENGTH: 107
<212> TYPE: PRT
<213> ORGANISM: Artificial
<220> FEATURE:
<223> OTHER INFORMATION: chimer

<400> SEQUENCE: 12

Gln Ile Val Leu Thr Gln Ser Pro Thr Ile Met Ser Ala Ser Pro Gly
1               5                   10                  15

Glu Arg Val Thr Met Thr Cys Ser Ala Ser Ser Ser Val Phe Tyr Met
                20                  25                  30

His Trp Tyr Gln Gln Lys Pro Gly Ser Ser Pro Arg Leu Leu Ile Tyr
            35                  40                  45

Asp Thr Ser Ile Leu Ser Ser Gly Val Pro Val Arg Phe Ser Gly Ser
        50                  55                  60

Gly Ser Gly Thr Ser Tyr Ser Leu Thr Ile Arg Arg Met Glu Ala Glu
65                  70                  75                  80

Asp Ala Ala Thr Tyr Tyr Cys Gln Gln Trp Ser Ser Tyr Pro Leu Thr
                85                  90                  95
```

```
Phe Gly Ala Gly Thr Lys Leu Glu Leu Lys Arg
            100                 105
```

<210> SEQ ID NO 13
<211> LENGTH: 122
<212> TYPE: PRT
<213> ORGANISM: Artificial
<220> FEATURE:
<223> OTHER INFORMATION: chimer

<400> SEQUENCE: 13

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Thr Tyr
            20                  25                  30

Trp Ile His Trp Val Lys Gln Arg Pro Gly Gln Gly Leu Glu Trp Ile
        35                  40                  45

Gly Ala Ile Asp Pro Gly Asn Ser Asp Ala Thr Tyr Ser Gln Lys Phe
    50                  55                  60

Lys Asp Lys Ala Lys Leu Thr Ala Val Thr Ser Ala Ser Thr Ala Phe
65                  70                  75                  80

Met Glu Leu Asn Ser Leu Thr Asn Asp Asp Ser Ala Val Tyr Tyr Cys
                85                  90                  95

Ser Arg Glu Val Tyr Tyr Gly Tyr Asp Gly Asp Tyr Phe Asp Tyr Trp
            100                 105                 110

Gly Gln Gly Thr Thr Leu Thr Val Ser Ser
        115                 120
```

<210> SEQ ID NO 14
<211> LENGTH: 112
<212> TYPE: PRT
<213> ORGANISM: Artificial
<220> FEATURE:
<223> OTHER INFORMATION: chimer

<400> SEQUENCE: 14

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Val His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Lys Leu Glu Ser Gly Val Pro Ala
    50                  55                  60

Arg Phe Ser Gly Ser Gly Ser Glu Thr Asp Phe Thr Leu Asn Ile His
65                  70                  75                  80

Pro Val Glu Glu Glu Asp Ala Ala Thr Tyr Phe Cys Gln Gln Ser Ile
                85                  90                  95

Gly Asp Pro Trp Thr Phe Gly Gly Thr Lys Leu Glu Ile Lys Arg
            100                 105                 110
```

<210> SEQ ID NO 15
<211> LENGTH: 117
<212> TYPE: PRT
<213> ORGANISM: Mus musculus

<400> SEQUENCE: 15

```
Glu Val Gln Leu Gln Gln Ser Gly Pro Glu Val Val Lys Thr Gly Gly
1               5                   10                  15
```

Ser Ala Lys Val Ser Cys Lys Ala Ser Gly Tyr Ser Phe Thr Gly Tyr
             20                  25                  30

Phe Met His Trp Val Lys Gln Ser His Gly Gln Ser Leu Glu Trp Ile
         35                  40                  45

Gly Tyr Ile Asn Cys Tyr Asn Gly Thr Ile Tyr Tyr Asn Gln Lys Phe
     50                  55                  60

Lys Gly Lys Ala Thr Phe Thr Val Asp Thr Ser Ser Thr Ala Ser
65                  70                  75                  80

Met Gln Phe Asn Ser Leu Thr Ser Glu Asp Ser Gly Val Tyr Tyr Cys
                 85                  90                  95

Ala Arg Gly Gly Asp Ser Ala Met Asp Tyr Trp Gly Gln Gly Thr Ser
            100                 105                 110

Val Thr Val Ser Ser
        115

<210> SEQ ID NO 16
<211> LENGTH: 108
<212> TYPE: PRT
<213> ORGANISM: Mus musculus

<400> SEQUENCE: 16

Asp Ile Val Met Thr Gln Ser Pro Ala Thr Leu Ser Val Thr Pro Gly
1               5                   10                  15

Asp Ser Ala Ser Leu Ser Cys Arg Ala Ser Gln Ser Ile Ser Asp Leu
             20                  25                  30

Leu His Trp Tyr Gln Gln Arg Ser His Glu Ser Pro Arg Leu Leu Ile
         35                  40                  45

Lys Tyr Ala Ser His Ser Ile Ser Gly Ile Pro Ser Arg Phe Ser Gly
     50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                 85                  90                  95

Thr Phe Gly Thr Gly Thr Lys Leu Glu Leu Lys Arg
            100                 105

<210> SEQ ID NO 17
<211> LENGTH: 32
<212> TYPE: DNA
<213> ORGANISM: Artificial
<220> FEATURE:
<223> OTHER INFORMATION: primer

<400> SEQUENCE: 17
cttgccattg agccagtcct ggtgcatgat gg                                   32

<210> SEQ ID NO 18
<211> LENGTH: 23
<212> TYPE: DNA
<213> ORGANISM: Artificial
<220> FEATURE:
<223> OTHER INFORMATION: primer

<400> SEQUENCE: 18
gttgttcaag aagcacacga ctg                                             23

<210> SEQ ID NO 19
<211> LENGTH: 36
<212> TYPE: DNA
<213> ORGANISM: Artificial

```
<220> FEATURE:
<223> OTHER INFORMATION: primer

<400> SEQUENCE: 19
gctctagact aacactcatt cctgttgaag ctcttg                             36

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
cccttgacca ggcatcccag                                               20

<210> SEQ ID NO 21
<211> LENGTH: 36
<212> TYPE: DNA
<213> ORGANISM: Artificial
<220> FEATURE:
<223> OTHER INFORMATION: primer

<400> SEQUENCE: 21
gctctagact aacactcatt cctgttgaag ctcttg                             36

<210> SEQ ID NO 22
<211> LENGTH: 115
<212> TYPE: PRT
<213> ORGANISM: Mus musculus

<400> SEQUENCE: 22
```

Asp Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Trp Ala Tyr Asp Gly Pro Trp Gly Gln Gly Thr Leu Val Thr
            100                 105                 110

Val Ser Ala
    115

```
<210> SEQ ID NO 23
<211> LENGTH: 107
<212> TYPE: PRT
<213> ORGANISM: Mus musculus

<400> SEQUENCE: 23
```

Gln Ile Val Leu Ser Gln Ser Pro Ala Leu Leu Ser Ala Ser Pro Gly
1               5                   10                  15

Glu Lys Val Thr Met Thr Cys Arg Ala Ser Ser Ser Val Ser His Met
            20                  25                  30

His Trp Tyr Gln Gln Lys Pro Gly Ser Ser Pro Lys Pro Trp Ile Tyr
        35                  40                  45

-continued

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Thr Arg Val Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys Arg
            100                 105

<210> SEQ ID NO 24
<211> LENGTH: 121
<212> TYPE: PRT
<213> ORGANISM: Mus musculus

<400> SEQUENCE: 24

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Ser Tyr
                20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Phe Asn Ala Ala Phe Met
    50                  55                  60

Ser Arg Val Ser Phe Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 25
<211> LENGTH: 107
<212> TYPE: PRT
<213> ORGANISM: Mus musculus

<400> SEQUENCE: 25

Asp Ile Val Met Thr Gln Ser Gln Lys Phe Met Ser Thr Thr Val Gly
1               5                   10                  15

Asp Lys Val Ser Ile Pro Cys Lys Ala Ser Glu Asn Val Gly Ala Ala
                20                  25                  30

Val Ala Trp Tyr Gln Gln Lys Pro Gly Gln Ser Pro Thr Leu Leu Ile
            35                  40                  45

Tyr Ser Ala Ser Asn Arg Tyr Thr Gly Ile Pro Asp Arg Phe Thr Gly
    50                  55                  60

Ser Gly Ser Gly Thr Asp Phe Thr Leu Thr Ile Arg Thr Val Gln Ser
65                  70                  75                  80

Glu Asp Leu Ala Asp Tyr Phe Cys Gln Gln Tyr Thr Asn Tyr Pro Thr
                85                  90                  95

Phe Gly Gly Gly Thr Lys Leu Glu Ile Lys Arg
            100                 105

<210> SEQ ID NO 26
<211> LENGTH: 121
<212> TYPE: PRT
<213> ORGANISM: Mus musculus

<400> SEQUENCE: 26

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 27
<211> LENGTH: 107
<212> TYPE: PRT
<213> ORGANISM: Mus musculus

<400> SEQUENCE: 27

Gly Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Pro Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Ala Asp Phe Thr Leu Thr Ile Ser Asn Leu His Ser
65                  70                  75                  80

Glu Asp Leu Ala Asp Tyr Phe Cys Gln Gln Tyr Thr Ser Tyr Pro Thr
                85                  90                  95

Phe Gly Gly Gly Thr Lys Leu Glu Ile Lys Arg
            100                 105

<210> SEQ ID NO 28
<211> LENGTH: 116
<212> TYPE: PRT
<213> ORGANISM: Mus musculus

<400> SEQUENCE: 28

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asn Thr Ile Phe Asp Pro Lys Phe
    50                  55                  60

Gln Gly Arg Ala Ser Ile Thr Ala Asp Thr Ser Ser Asn Thr Ala Tyr
65                  70                  75                  80

```
Leu Gln Leu Ser Ser Leu Thr Ser Glu Asp Thr Ala Val Tyr Tyr Cys
                85                  90                  95

Ala Gly Arg Trp Tyr Ala Met Asp Tyr Trp Gly Gln Gly Thr Ser Val
            100                 105                 110

Thr Val Ser Ser
        115

<210> SEQ ID NO 29
<211> LENGTH: 113
<212> TYPE: PRT
<213> ORGANISM: Mus musculus

<400> SEQUENCE: 29

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Thr His Phe Pro Trp Thr Phe Gly Gly Gly Thr Lys Leu Glu Ile Lys
            100                 105                 110

Arg

<210> SEQ ID NO 30
<211> LENGTH: 121
<212> TYPE: PRT
<213> ORGANISM: Mus musculus

<400> SEQUENCE: 30

Gln Val Gln Leu Lys Gln Ser Gly Pro Gly Leu Val Gln Pro Ser Gln
1               5                   10                  15

Ser Leu Ser Ile Ser Cys Thr Val Ser Gly Phe Ser Leu Thr Gly Tyr
            20                  25                  30

Gly Val His Trp Ile Arg Gln Ser Pro Gly Lys Gly Leu Glu Trp Leu
        35                  40                  45

Gly Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 31
<211> LENGTH: 107
<212> TYPE: PRT
<213> ORGANISM: Mus musculus

<400> SEQUENCE: 31
```

```
Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Glu Leu Leu Ile
        35                  40                  45

Tyr Ser Ala Ser Asn Arg Tyr Thr Arg Val Pro Asp Arg Phe Thr Gly
50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Thr Ser Tyr Pro Thr
            85                  90                  95

Phe Gly Gly Gly Thr Lys Leu Glu Ile Lys Arg
            100                 105
```

<210> SEQ ID NO 32
<211> LENGTH: 121
<212> TYPE: PRT
<213> ORGANISM: Artificial
<220> FEATURE:
<223> OTHER INFORMATION: Humanized

<400> SEQUENCE: 32

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser
            115                 120
```

<210> SEQ ID NO 33
<211> LENGTH: 113
<212> TYPE: PRT
<213> ORGANISM: Artificial
<220> FEATURE:
<223> OTHER INFORMATION: Humanized

<400> SEQUENCE: 33

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
```

65                  70                  75                  80
Ser Arg Val Glu Ala Glu Asp Val Gly Val Tyr Tyr Cys Leu Gln Ala
                    85                  90                  95

Thr His Phe Pro Gln Thr Phe Gly Gly Gly Thr Lys Val Glu Ile Lys
                100                 105                 110

Arg

<210> SEQ ID NO 34
<211> LENGTH: 121
<212> TYPE: PRT
<213> ORGANISM: Artificial
<220> FEATURE:
<223> OTHER INFORMATION: Humanized

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ser Thr Ile Ser Arg Ser Gly Ser Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
                100                 105                 110

Gln Gly Thr Thr Val Thr Val Ser Ser
115                 120

<210> SEQ ID NO 35
<211> LENGTH: 113
<212> TYPE: PRT
<213> ORGANISM: Artificial
<220> FEATURE:
<223> OTHER INFORMATION: Humanized

<400> SEQUENCE: 35

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
                20                  25                  30

Asp Gly Lys Thr Tyr Leu Asn Trp Tyr Leu Gln Lys Pro Gly Gln Ser
            35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
                100                 105                 110

Arg

<210> SEQ ID NO 36

```
<211> LENGTH: 121
<212> TYPE: PRT
<213> ORGANISM: Artificial
<220> FEATURE:
<223> OTHER INFORMATION: Humanized

<400> SEQUENCE: 36

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Ser Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser
        115                 120

<210> SEQ ID NO 37
<211> LENGTH: 113
<212> TYPE: PRT
<213> ORGANISM: Artificial
<220> FEATURE:
<223> OTHER INFORMATION: Humanized

<400> SEQUENCE: 37

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Leu Gln Arg Pro Gly Glu Ser
        35                  40                  45

Pro Lys Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg

<210> SEQ ID NO 38
<211> LENGTH: 118
<212> TYPE: PRT
<213> ORGANISM: Mus musculus

<400> SEQUENCE: 38

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30
```

```
Tyr Met Tyr Trp Val Lys Gln Arg Pro Gly Gln Gly Leu Glu Trp Ile
            35                  40                  45

Gly Glu Ile Asn Pro Ser Asn Gly Asp Thr Asn Leu Asn Glu Lys Phe
 50                      55                  60

Lys Ser Lys Ala Thr Leu Thr Val Asp Lys Ser Ser Ser Thr Val Tyr
 65                  70                  75                  80

Met Gln Leu Ser Ser Leu Thr Ser Glu Asp Ser Ala Val Tyr Tyr Cys
                 85                  90                  95

Thr Arg Trp Asp Arg Phe Asp Gly Phe Val Tyr Trp Gly Gln Gly Thr
            100                 105                 110

Leu Val Thr Val Ser Ala
        115
```

<210> SEQ ID NO 39
<211> LENGTH: 108
<212> TYPE: PRT
<213> ORGANISM: Mus musculus

<400> SEQUENCE: 39

```
Glu Thr Thr Val Thr Gln Ser Pro Ala Ser Leu Ser Met Ala Ile Gly
 1               5                  10                  15

Gly Lys Val Thr Ile Arg Cys Ile Ile Ser Thr Asn Ile Asp Asp Asp
            20                  25                  30

Ile Asn Trp Tyr Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
 50                      55                  60

Ser Gly Tyr Gly Thr Asp Phe Val Phe Thr Ile Glu Asn Met Leu Ser
 65                  70                  75                  80

Glu Asp Val Ala Asp Tyr Tyr Cys Leu Gln Ser Asp Asn Leu Pro Tyr
                 85                  90                  95

Thr Phe Gly Gly Gly Thr Lys Leu Glu Ile Lys Arg
            100                 105
```

<210> SEQ ID NO 40
<211> LENGTH: 227
<212> TYPE: PRT
<213> ORGANISM: Artificial
<220> FEATURE:
<223> OTHER INFORMATION: chimer

<400> SEQUENCE: 40

```
Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
            35                  40                  45

Ala Val Ile Trp Arg Gly Gly Ser Ile Asp Tyr Asn Ala Ala Phe Met
 50                      55                  60

Ser Arg Leu Ser Ile Thr Lys Asp Asn Ser Lys Ser Gln Val Phe Phe
 65                  70                  75                  80

Lys Met Asn Ser Leu Gln Ala Asp Asp Thr Ala Ile Tyr Tyr Cys Ala
                 85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser Ala Ser Thr Lys Gly Pro Ser
```

```
                    115                 120                 125
Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
    210                 215                 220

Pro Pro Cys
225

<210> SEQ ID NO 41
<211> LENGTH: 213
<212> TYPE: PRT
<213> ORGANISM: Artificial
<220> FEATURE:
<223> OTHER INFORMATION: Chimer

<400> SEQUENCE: 41

Gly Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Pro Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Ala Asp Phe Thr Leu Thr Ile Ser Asn Leu His Ser
65                  70                  75                  80

Glu Asp Leu Ala Asp Tyr Phe Cys Gln Gln Tyr Thr Ser Tyr Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 42
<211> LENGTH: 116
<212> TYPE: PRT
```

```
<213> ORGANISM: Mus musculus

<400> SEQUENCE: 42

Gln Val Gln Leu Gln Gln Ser Gly Ala Glu Leu Ala Arg Pro Gly Ala
1               5                   10                  15

Ser Val Lys Leu Ser Ala Arg Leu Leu Ala Ser Pro Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Gly Gly Ala Lys Thr Phe Tyr Ser Glu Lys Phe
    50                  55                  60

Lys Gly Lys Ala Thr Leu Thr Ala Asp Ile Ser Ser Thr Ala Tyr
65                  70                  75                  80

Met Gln Leu Ser Ser Leu Thr Ser Glu Asp Ser Ala Val Tyr Phe Cys
                85                  90                  95

Ala Gly Tyr Tyr Tyr Gly Phe Asp Phe Trp Gly Gln Gly Thr Thr Leu
                100                 105                 110

Thr Val Ser Ser
        115

<210> SEQ ID NO 43
<211> LENGTH: 112
<212> TYPE: PRT
<213> ORGANISM: Mus musculus

<400> SEQUENCE: 43

Asp Ile Val Leu Thr Gln Ser Pro Pro Ser Leu Ala Val Ser Leu Gly
1               5                   10                  15

Gln Arg Ala Ile Ile Ser Cys Arg Ala Ser Gln Ser Ile Ser Phe Ala
            20                  25                  30

Gly Thr Ser Leu Val His Trp Tyr Gln Gln Lys Pro Gly Gln Gln Pro
        35                  40                  45

Lys Leu Leu Ile Tyr Arg Ala Ser Thr Leu Glu Ala Gly Val Pro Thr
    50                  55                  60

Arg Phe Ser Gly Ser Gly Ser Gly Thr Asp Phe Thr Leu Asn Ile His
65                  70                  75                  80

Pro Val Glu Glu Asp Asp Ala Thr Thr Tyr Tyr Cys Gln Gln Thr Arg
                85                  90                  95

Glu Phe Pro Phe Thr Phe Gly Ser Gly Thr Lys Leu Glu Ile Lys Arg
                100                 105                 110

<210> SEQ ID NO 44
<211> LENGTH: 120
<212> TYPE: PRT
<213> ORGANISM: Mus musculus

<400> SEQUENCE: 44

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Ser Gly Gly Thr Ser Tyr Asn Gln Lys Phe
    50                  55                  60

Lys Gly Glu Ala Thr Leu Thr Val Asp Lys Ser Ser Ser Thr Ala Phe
65                  70                  75                  80
```

-continued

```
Met His Leu Asn Ser Leu Thr Ser Glu Asp Ser Ala Val Tyr Tyr Cys
                 85                  90                  95

Val Arg Glu Gly Asn Arg Tyr Asp Glu Arg Phe Thr Tyr Trp Gly Gln
            100                 105                 110

Gly Thr Leu Val Thr Val Ser Ala
        115                 120

<210> SEQ ID NO 45
<211> LENGTH: 108
<212> TYPE: PRT
<213> ORGANISM: Mus musculus

<400> SEQUENCE: 45

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Ser Ser Trp Pro Leu
                85                  90                  95

Thr Phe Gly Ala Gly Thr Lys Leu Glu Leu Lys Arg
            100                 105

<210> SEQ ID NO 46
<211> LENGTH: 117
<212> TYPE: PRT
<213> ORGANISM: Mus musculus

<400> SEQUENCE: 46

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Val Glu Trp
        35                  40                  45

Met Ala Tyr Ile His Tyr Ser Gly Ser Thr Arg Tyr Asn Pro Ser Leu
50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ser Ala Thr Tyr Tyr Cys
                85                  90                  95

Gly Arg Arg Ala Trp Thr Trp Phe Asp Tyr Trp Gly Gln Gly Thr Leu
            100                 105                 110

Val Thr Val Ser Ala
115

<210> SEQ ID NO 47
<211> LENGTH: 112
<212> TYPE: PRT
<213> ORGANISM: Mus musculus

<400> SEQUENCE: 47
```

```
Asp Ile Val Leu Thr Gln Ser Pro Gly Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asn Ser Phe Met Asn Trp Tyr Gln Gln Arg Pro Gly Gln Pro Pro
        35                  40                  45

Lys Leu Leu Ile Tyr Glu Ala Ser Asn Leu Glu Ser Gly Ile Pro Val
    50                  55                  60

Arg Phe Ser Gly Ser Gly Ser Gly Thr Asp Phe Thr Leu Asn Ile His
65                  70                  75                  80

Pro Val Glu Glu Asp Val Ala Thr Tyr Tyr Cys Gln Gln Ser Lys
                85                  90                  95

Glu Asp Pro Trp Thr Phe Gly Gly Gly Thr Lys Leu Glu Ile Lys Arg
            100                 105                 110
```

<210> SEQ ID NO 48
<211> LENGTH: 445
<212> TYPE: PRT
<213> ORGANISM: Artificial
<220> FEATURE:
<223> OTHER INFORMATION: chimer

<400> SEQUENCE: 48

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Asp Thr Asn Leu Asn Glu Lys Phe
    50                  55                  60

Lys Ser Lys Ala Thr Leu Thr Val Asp Lys Ser Ser Thr Val Tyr
65                  70                  75                  80

Met Gln Leu Ser Ser Leu Thr Ser Glu Asp Ser Ala Val Tyr Tyr Cys
                85                  90                  95

Thr Arg Trp Asp Arg Phe Asp Gly Phe Val Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 49
<211> LENGTH: 214
<212> TYPE: PRT
<213> ORGANISM: Artificial
<220> FEATURE:
<223> OTHER INFORMATION: chimer

<400> SEQUENCE: 49

Glu Thr Thr Val Thr Gln Ser Pro Ala Ser Leu Ser Met Ala Ile Gly
1               5                   10                  15

Gly Lys Val Thr Ile Arg Cys Ile Ile Ser Thr Asn Ile Asp Asp Asp
            20                  25                  30

Ile Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asp Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 50
<211> LENGTH: 448
<212> TYPE: PRT
<213> ORGANISM: Artificial
<220> FEATURE:
<223> OTHER INFORMATION: Humanized

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 51
<211> LENGTH: 219
<212> TYPE: PRT
<213> ORGANISM: Artificial
<220> FEATURE:
<223> OTHER INFORMATION: Humanized

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 52
<211> LENGTH: 222
```

```
<212> TYPE: PRT
<213> ORGANISM: Artificial
<220> FEATURE:
<223> OTHER INFORMATION: Chimer

<400> SEQUENCE: 52
```

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys
    210                 215                 220

```
<210> SEQ ID NO 53
<211> LENGTH: 213
<212> TYPE: PRT
<213> ORGANISM: Artificial
<220> FEATURE:
<223> OTHER INFORMATION: chimer

<400> SEQUENCE: 53
```

Gly Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Pro Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Ala Asp Phe Thr Leu Thr Ile Ser Asn Leu His Ser
65                  70                  75                  80

Glu Asp Leu Ala Asp Tyr Phe Cys Gln Gln Tyr Thr Ser Tyr Pro Thr
                85                  90                  95

Phe Gly Gly Gly Thr Lys Leu Glu Ile Lys Arg Thr Val Ala Ala Pro
            100                 105                 110

```
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 54
<211> LENGTH: 448
<212> TYPE: PRT
<213> ORGANISM: Artificial
<220> FEATURE:
<223> OTHER INFORMATION: Humanized

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 55
<211> LENGTH: 219
<212> TYPE: PRT
<213> ORGANISM: Artificial
<220> FEATURE:
<223> OTHER INFORMATION: Humanized

<400> SEQUENCE: 55

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
            210                 215
```

<210> SEQ ID NO 56
<211> LENGTH: 448
<212> TYPE: PRT
<213> ORGANISM: Artificial
<220> FEATURE:
<223> OTHER INFORMATION: Humanized

<400> SEQUENCE: 56

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ser Thr Ile Ser Arg Ser Gly Ser Tyr Ser Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Leu Gly Gly Tyr Asp Glu Gly Asp Ala Met Asp Ser Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 57
<211> LENGTH: 219
<212> TYPE: PRT
<213> ORGANISM: Artificial
<220> FEATURE:
<223> OTHER INFORMATION: Humanized

<400> SEQUENCE: 57

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
                20                  25                  30

Asp Gly Lys Thr Tyr Leu Asn Trp Leu Leu Gln Arg Pro Gly Glu Ser
                35                  40                  45

Pro Lys Leu Leu Ile Tyr Leu Val Ser Ile Leu Asp Ser Gly Val Pro
                50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 58
```

```
<211> LENGTH: 227
<212> TYPE: PRT
<213> ORGANISM: Artificial
<220> FEATURE:
<223> OTHER INFORMATION: Humanized

<400> SEQUENCE: 58

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Ser Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys
225

<210> SEQ ID NO 59
<211> LENGTH: 219
<212> TYPE: PRT
<213> ORGANISM: Artificial
<220> FEATURE:
<223> OTHER INFORMATION: Humanized

<400> SEQUENCE: 59

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
```

```
                    85                  90                  95
Thr His Phe Pro Gln Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215
```

<210> SEQ ID NO 60
<211> LENGTH: 118
<212> TYPE: PRT
<213> ORGANISM: Mus musculus

<400> SEQUENCE: 60

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Lys Phe Ser Asn Tyr
                20                  25                  30

Trp Met Asn Trp Val Lys Gln Arg Pro Gly Gln Gly Leu Glu Trp Ile
            35                  40                  45

Gly Leu Ile Tyr Pro Gly Asp Gly Asn Thr Lys Tyr Asn Gly Glu Phe
        50                  55                  60

Lys Val Lys Ala Thr Leu Thr Ala Asp Lys Ser Ser Thr Thr Ala Tyr
65                  70                  75                  80

Leu Gln Leu Asn Ser Leu Thr Ser Glu Asp Ser Ala Val Tyr Phe Cys
                85                  90                  95

Ala Arg Gly Gly Asn Ala Val Val Gly Asp Tyr Trp Gly Gln Gly Thr
                100                 105                 110

Thr Leu Thr Val Ser Ser
        115
```

<210> SEQ ID NO 61
<211> LENGTH: 108
<212> TYPE: PRT
<213> ORGANISM: Mus musculus

<400> SEQUENCE: 61

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ile Ile Ser Asp Tyr
                20                  25                  30

Leu His Trp Tyr Gln Gln Lys Ser His Glu Ser Pro Arg Leu Leu Ile
            35                  40                  45

Lys Phe Ala Ser Gln Pro Ile Ser Gly Ile Pro Ser Arg Phe Arg Gly
        50                  55                  60

Ser Gly Ser Gly Ser Asp Phe Thr Leu Ser Ile Asn Ser Val Glu Pro
```

```
                65                  70                  75                  80
Glu Asp Val Gly Val Tyr Tyr Cys Gln Asn Gly His Ser Phe Pro Phe
                    85                  90                  95

Thr Phe Gly Ser Gly Thr Lys Leu Glu Ile Lys Arg
                   100                 105

<210> SEQ ID NO 62
<211> LENGTH: 86
<212> TYPE: PRT
<213> ORGANISM: Artificial
<220> FEATURE:
<223> OTHER INFORMATION: Tagged

<400> SEQUENCE: 62

Gly Ser Ser Gly Ser Ser Gly Asp Ser Glu Glu Asp Glu His Thr
1               5                   10                  15

Ile Ile Thr Asp Thr Glu Leu Pro Pro Leu Lys Leu Met His Ser Phe
                20                  25                  30

Cys Ala Phe Lys Ala Asp Asp Gly Pro Cys Lys Ala Ile Met Lys Arg
            35                  40                  45

Phe Phe Phe Asn Ile Phe Thr Arg Gln Cys Glu Glu Phe Ile Tyr Gly
        50                  55                  60

Gly Cys Glu Gly Asn Gln Asn Arg Phe Glu Ser Leu Glu Glu Cys Lys
65                  70                  75                  80

Lys Met Cys Thr Arg Asp
                85

<210> SEQ ID NO 63
<211> LENGTH: 451
<212> TYPE: PRT
<213> ORGANISM: Artificial
<220> FEATURE:
<223> OTHER INFORMATION: Humanized

<400> SEQUENCE: 63

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Thr Pro Glu Lys Arg Leu Glu Trp Val
            35                  40                  45

Ala Thr Ile Ser Arg Ser Gly Ser Tyr Ser Tyr Phe Pro Asp Ser Val
        50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 64
<211> LENGTH: 219
<212> TYPE: PRT
<213> ORGANISM: Artificial
<220> FEATURE:
<223> OTHER INFORMATION: Humanized

<400> SEQUENCE: 64

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Leu Gln Ala
            85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 65
<211> LENGTH: 448
<212> TYPE: PRT
<213> ORGANISM: Artificial
<220> FEATURE:
<223> OTHER INFORMATION: chimer

<400> SEQUENCE: 65

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Tyr Met Tyr Trp Val Lys Gln Arg Pro Gly Gln Gly Leu Glu Trp Ile
            35                  40                  45

Gly Glu Ile Asn Pro Ser Asn Gly Asp Thr Asn Leu Asn Glu Lys Phe
50                  55                  60

Lys Ser Lys Ala Thr Leu Thr Val Asp Lys Ser Ser Ser Thr Val Tyr
65                  70                  75                  80

Met Gln Leu Ser Ser Leu Thr Ser Glu Asp Ser Ala Val Tyr Tyr Cys
            85                  90                  95

Thr Arg Trp Asp Arg Phe Asp Gly Phe Val Tyr Trp Gly Gln Gly Thr
            100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

-continued

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 66
<211> LENGTH: 214
<212> TYPE: PRT
<213> ORGANISM: Artificial
<220> FEATURE:
<223> OTHER INFORMATION: chimer

<400> SEQUENCE: 66

Glu Thr Thr Val Thr Gln Ser Pro Ala Ser Leu Ser Met Ala Ile Gly
1               5                   10                  15

Gly Lys Val Thr Ile Arg Cys Ile Ile Ser Thr Asn Ile Asp Asp Asp
            20                  25                  30

Ile Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asp Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 67
<211> LENGTH: 451
<212> TYPE: PRT
<213> ORGANISM: Artificial
<220> FEATURE:
<223> OTHER INFORMATION: Humanized

<400> SEQUENCE: 67

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 68
<211> LENGTH: 219
<212> TYPE: PRT
<213> ORGANISM: Artificial
<220> FEATURE:
<223> OTHER INFORMATION: Humanized

<400> SEQUENCE: 68

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

```
Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 69
<211> LENGTH: 448
<212> TYPE: PRT
<213> ORGANISM: Artificial
<220> FEATURE:
<223> OTHER INFORMATION: mod heavy chain

<400> SEQUENCE: 69

Gln Val Gln Leu Gln Gln Ser Gly Ala Glu Leu Val Lys Pro Gly Ala
 1                   5                  10                  15

Ser Val Lys Leu Ser Cys Lys Ala Ser Gly Tyr Thr Phe Ile Ser Tyr
                20                  25                  30

Tyr Met Tyr Trp Val Lys Gln Arg Pro Gly Gln Gly Leu Glu Trp Ile
            35                  40                  45

Gly Glu Ile Asn Pro Ser Asn Gly Asp Thr Asn Leu Asn Glu Lys Phe
    50                  55                  60

Lys Ser Lys Ala Thr Leu Thr Val Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Thr Arg Trp Asp Arg Phe Asp Gly Phe Val Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 70
<211> LENGTH: 214
<212> TYPE: PRT
<213> ORGANISM: Mus musculus

<400> SEQUENCE: 70

Glu Thr Thr Val Thr Gln Ser Pro Ala Ser Leu Ser Met Ala Ile Gly
1               5                   10                  15

Gly Lys Val Thr Ile Arg Cys Ile Ile Ser Thr Asn Ile Asp Asp Asp
            20                  25                  30

Ile Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```